United States Patent
Fett et al.

(10) Patent No.: US 8,546,391 B2
(45) Date of Patent: Oct. 1, 2013

(54) THIADIAZOLE AND OXADIAZOLE DERIVATIVES, PREPARATION THEREOF AND THERAPEUTIC USE THEREOF

(75) Inventors: Eykmar Fett, Paris (FR); Patrick Mougenot, Paris (FR); Claudie Namane, Paris (FR); Eric Nicolai, Paris (FR); Christophe Philippo, Paris (FR)

(73) Assignee: Sanofi, Paris (FR)

( * ) Notice: Subject to any disclaimer, the term of this patent is extended or adjusted under 35 U.S.C. 154(b) by 10 days.

(21) Appl. No.: 13/145,665

(22) PCT Filed: Jan. 27, 2010

(86) PCT No.: PCT/FR2010/050124
§ 371 (c)(1),
(2), (4) Date: Oct. 11, 2011

(87) PCT Pub. No.: WO2010/086551
PCT Pub. Date: Aug. 5, 2010

(65) Prior Publication Data
US 2012/0040984 A1 Feb. 16, 2012

(30) Foreign Application Priority Data

Jan. 28, 2009 (FR) .................................. 09 00359
Sep. 1, 2009 (FR) .................................. 09 04137

(51) Int. Cl.
| | | |
|---|---|---|
| *A61K 31/5377* | (2006.01) | |
| *A61K 31/433* | (2006.01) | |
| *A61K 31/4439* | (2006.01) | |
| *A61K 31/4245* | (2006.01) | |
| *C07D 417/06* | (2006.01) | |
| *C07D 417/12* | (2006.01) | |
| *C07D 271/113* | (2006.01) | |
| *C07D 285/135* | (2006.01) | |

(52) U.S. Cl.
USPC ........ 514/236.2; 514/363; 514/364; 514/342; 546/268.7; 546/269.1; 548/139

(58) Field of Classification Search
USPC ................. 514/363, 364, 342; 548/143, 139; 546/268.7, 269.1
See application file for complete search history.

(56) References Cited

U.S. PATENT DOCUMENTS

| 6,100,077 A | 8/2000 | Sturley et al. |
| 7,453,010 B2 | 11/2008 | Bovy et al. |
| 2004/0063700 A1 | 4/2004 | Cheng et al. |
| 2005/0143384 A1 | 6/2005 | Sartori et al. |

FOREIGN PATENT DOCUMENTS

| WO | WO 03/099772 | 12/2003 |
| WO | WO2005/065683 A1 | 7/2005 |
| WO | WO2006/134317 A1 | 12/2006 |
| WO | WO2007/115935 A1 | 10/2007 |

OTHER PUBLICATIONS

Schafer et al. Drug Discovery Today, 2008, 13 (21/22), 913-916.*
Horig et al. Journal of Translational Medicine 2004, 2(44), p. 1-8.*
U.S. Appl. No. 13/747,862, filed Jan. 23, 2013, Fett, et al.
Reasner, Reducing Cardiovascular Complications of Type 2 Diabetes by Targeting Multiple Risk Factors, J. Cardiovasc Pharmacol, vol. 52, No. 2, (2008), pp. 136-144.
King, The Role of Inflammatory Cytokines in Diabetes and its Complications, J Periodontal, (2008), (Suppl.) vol. 79, pp. 1527-1534.
Ginsberg, et al., Metabolic Syndrome: Focus on Dsylipidemia, Obesity, vol. 14, Supplement, (2006), 41S-49S.
Adiels, et al., Diabetic Dyslipidaemia, Current Opinion in Lipidology, (2006), vol. 17, pp. 238-246.
Adiels, et al., Over Production of Very Low-Density Lipoproteins is the Hallmark of the Dyslipidernia in the Metabolic Syndrome, Arteriosclerosis, Thrombosis, and Vascular Biology, (2008), vol. 28, pp. 1225-1236.
Eschwege, et al., The dysmetabolic syndrome, insulin resistance and increased cardiovascular (CV) morbidity and mortality in type 2 diabetes: aetiological factors in the development of CV complications, Diabetes Metab., (2003), vol. 29, (4 Pt 2):6519-27, (Abstract).
Parekh, et al., Abnormal Lipid and Glucose Metabolism in Obesity: Implications for Nonalcoholic Fatty Liver Disease, Gastroenterology, (2007), vol. 132, pp. 2191-2207.
Lewis, et al., Disordered Fat Storage and Mobilization in the Pathogenesis of Insulin Resistance and Type 2 Diabetes, Endocrine Reviews, vol. 23, No. 2, pp. 201-229, (2002).
McBride, Triglycerides and Risk for Coronary Artery Disease, Current Atherosclerosis Reports, (2008), vol. 10, 386-390.
Chen, et al., Leptin Modulates the Effects of Acyl CoA:Diacylglycerol Acyltransferase Deficiency on Murine Fur and Sebaceous Glands, The Journal of Clinicial Investigation, (2002), vol. 109, No. 2, pp. 175-181.
Yosipovitch, et al., Obesity and the Skin: Skin Physiology and Skin Manifestations of Obesity, J. Am. Acad. Dermatol., vol. 56, pp. 901-916, (2007).
Pahan, Biomedicine & Diseases: Review Lipid-Lowering Drugs, Cell. Mol. Life Sci., vol. 63, (2006), pp. 1165-1178.

(Continued)

*Primary Examiner* — Yong Chu
(74) *Attorney, Agent, or Firm* — Janann Y. Ali

(57) ABSTRACT

The invention relates to compounds of the formula (I) either (i) in the state of a base or an acid addition salt, or (ii) in the state of an acid or a base addition salt, as well as to a method for preparing same and to the therapeutic applications thereof.

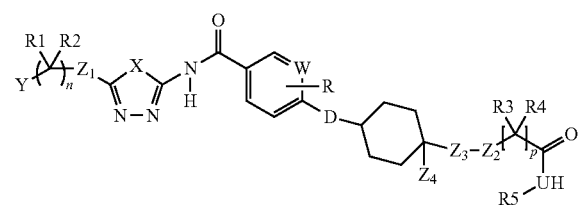

25 Claims, No Drawings

(56) References Cited

OTHER PUBLICATIONS

Unger, Minireview: Weapons of Lean Body Mass Destruction: The Role of Ectopic Lipids in the Metabolic Syndrome, Endocrinology, vol. 144, No. 12, pp. 5159-5165 (2003).

Caputo, et al., Synthesis and Ionization of Meta- and Para-Substituted cis-3-Phenylcyclobutanecarboxylic. Acids, J. Org. Chem., (1968), pp. 1959-1962.

Gillis, et al., The Reaction of Ethyl Azodicarboxylate with Conjugated Dienes, J. Org. Chem., (1962). pp. 1947-1951.

Krane, et al., Dyslipidaemia in Chronic Kidney Disease, Minerva Urol Nefrol, (2007), vol. 59, pp. 299-316.

Ridker, et al., Inflammation, C-Reactive Protein, and Atherothrombosis, J. Periodontol vol. 79, pp. 1544-1551 (2008).

Kotler, HIV and Antiretroviral Therapy: Lipid Abnormalities and Associated Cardiovascular Risk in HIV-Infected Patients, J. Acquired Immune Defic. Syndr., vol. 49, pp. S79-S85, (2008).

Schaffler, et al., Mechanisms of Disease: Adipocytokines and Visceral Adipose Tissue—Emerging Role in Intestinal and Mesentric Diseases, Nat. Clin. Pract. Gastroenterol. Hepatol., vol. 2, pp. 103-111, (2005).

Grundy, Metabolic Complications of Obesity, Endocrine, vol. 13, No. 2, pp. 155-165, (2000).

Chen, et al., Inhibition of Triglyceride Synthesis as a Treatment Strategy for Obesity, Arterioscler Thromb Vasc. Biol., (2005), vol. 25, pp. 482-486.

Cases, et al., Identification of a Gene Encoding an Acyl CoA:Diacylglycercill Acyltransferase, a Key Enzyme in Triacylglycerol Synthesis, Proc. Natl. Acad. Sci. USA, vol. 95, pp. 13018-13023, (1998).

Cases, et al., Cloning of DGAT2, a second Mammalian Diacylglycerol Acyltransferase, and Related Family Members, The Journal of Biological Chemistry, vol. 276, No. 42, (2001), pp. 38870-38876.

Chen, et al., Increased Insulin and Leptin Sensitivity in Mice Lacking Acyl CoA:Diacylglyceroi Acyitransferase 1, The Journal of Clinical Investigation, (2002), vol. 109, No. 8, pp. 1049-1055.

Buhman, et al., DGAT1 Is Not Essential for Intestinal Triacylglycerol Absorption or Chylomicron Synthesis, The Journal of Biological Chemistry, vol. 277, No. 28, (2002), pp. 25474-25479.

Sato, et al., A Citrus Polymethoxy Flavonoid, Nobiletin Inhibits Sebum Production and Sebocyte Proliferation, and Augments Sebum Excretion in Hamsters, Journal of Investigative Dermatology, vol. 127. pp. 2740-2748, (2007).

Herker, et al., Efficient Hepatitis C Virus Particle Formation Requires Diacylglycerol Acyltransferase-1, Nature Medicine, vol. 16, No. 11, (2010), pp. 1295-1298.

Villanueva, et al., Specific Role for Acyl CoA: Diacylglycerol Acyltransferase 1 (Dgat1) in Hepatic Steatosis Due to Exogenous Fatty Acids, Hepatology, vol. 50, No. 2, pp. 434-442, (2009).

Smith, et al., Obesity Resistance and Multiple Mechanisms of Triglyceride Synthesis in Mice Lacking Dgat, Nature Genetics, vol. 25, (2000), pp. 87-90.

\* cited by examiner

THIADIAZOLE AND OXADIAZOLE DERIVATIVES, PREPARATION THEREOF AND THERAPEUTIC USE THEREOF

The present invention relates to thiadiazole and oxadiazole derivatives, to their preparation and to their therapeutic use.

Triacylglycerides represent the main form of energy storage in eukaryotes, and may also be the cause of disorders or imbalances in the metabolism of triglycerides, involved in the pathogenesis and the increase of risk of several pathologies such as obesity, insulin resistance, type 2 diabetes (Reasner C. A., J. Cardiovasc. Pharmacol. 52:136-44, 2008) and complications arising from this pathology (Krane and Wanner, Minerva Urol. Nefrol. 59(3):299-316, 2007; King G. L., J. Periodontol. 79:1527-34, 2008), dyslipidaemia, which is characterized by high levels of plasmatic triglycerides, low levels of high-density lipoprotein (HDL) and the appearance of small dense low-density lipoprotein (sdLDL) and excessive postprandial lipidaemia (Ginsberg et al., Obesity (Silver Spring). 14: 41S-49S, 2006, Adiels et al., Curr. Opin. Lipidol. 17: 238-246, 2006, Adiels et al., ATVB 28:1225-1236, 2008), impaired fasting glucose conditions, metabolic acidosis, ketosis, metabolic syndrome (Eschwège E. Diabetes Metab. 29:6 S19-27, 2003), hepatic steatosis (Parekh and Anania. Gastroenterology 132:2191-2207, 2007), coronary diseases (Lewis, et al., Endocrine Review 23:701, 2002; Ridker and Silvertown, J. Periodontol., 79:1544-51, 2008; McBride P. Curr. Atheroscler. Rep. 10:386-90, 2008), skin diseases (Chen et al., J. Clin. Invest., 109:175-81, 2002; Yosipovitch et al., J. Am. Acad. Dermatol., 56:901-16, 2007), Alzheimer's disease, various immunomodulatory diseases (Pahan K., Cell Mol. Life. Sci., 63:1165-78, 2006), infection with HIV (Kotler D. P., J. Acquired Immune Defic. Syndr., 49:S79-85, 2008), irritable bowel syndrome (Schäffler et al., Nat. Clin. Pract. Gastroenterol. Hepatol., 2:103-11, 2005). Excessive storage of triacylglycerides in lean tissues, such as the liver, the muscles and other peripheral tissues, leads to dysfunction in these tissues; whereas reducing the accumulation of these fats in these peripheral tissues appears to be beneficial in treating lipotoxicity (Unger, Endocrinology, 144: 5 159-5 165, 2003). Excessive accumulation of triacylglycerides in adipose tissue (WAT) leads to obesity, a condition that is associated with a reduction in lifespan, type II diabetes, coronary diseases, hypertension, strokes, and the development of certain cancers (Grundy, Endocrine 13 (2): 155-165, 2000).

Document WO 2006/134 317 describes compounds which inhibit the activity of diacylglycerol acyltransferase (DGAT1) and which are thus useful in the treatment of disorders or imbalances in triglyceride metabolism.

Diacylglycerol acyltransferase (DGAT1) catalyses the formation of triglycerides from diacylglycerol and acyl-CoA in animal or human cells, triglycerides representing the main form of energy storage.

Obesity, type 2 diabetes and complications thereof are pathologies that are very widespread in modern society, and the pharmacological treatment options are currently limited, hence the need to develop pharmaceutical treatment agents, for preventing, retarding or treating disorders associated with obesity or with type 2 diabetes and complications thereof, which are safe and effective.

The compounds of the invention inhibit the biosynthesis of triglycerides and are useful for treating pathologies in which such an inhibition is beneficial, for instance in the case of obesity, dyslipidaemia, hepatic steatosis, type 2 diabetes, metabolic syndrome and coronary diseases.

One subject of the present invention is compounds corresponding to formula (I)

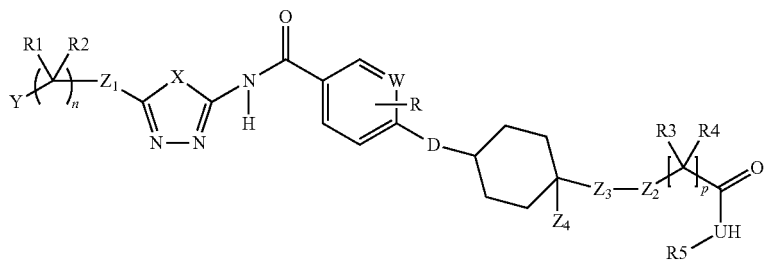

in which

U represents an oxygen atom or a nitrogen atom, given that when U represents an oxygen atom, then R5 is absent;

n is equal to 0, 1, 2 or 3;

p is equal to 0, 1 or 2;

D represents an oxygen atom, a group —NH— or a bond;

W represents a carbon or nitrogen atom;

X represents a heteroatom chosen from an oxygen atom and a sulfur atom;

R2, R3 and R4 represent, independently of each other,
a hydrogen atom,
a group —(C1-C6)alkyl, or alternatively,
(i) R1 and R2 may form, with the carbon atom to which they are attached, a group —(C3-C10)cycloalkyl- and/or (ii) R3 and R4 may form, with the carbon atom to which they are attached, a group —(C3-C10)cycloalkyl-;

Y represents a hydrogen atom, a group —(C1-C6)alkyl, —(C3-C10)cycloalkyl-, (C3-C10)cycloalkyloxy-, (C3-C10) cycloalkyl-(C1-C6)alkyloxy-, heterocycloalkyl-(C1-C6) alkyloxy-, a group —COOR1, aryl, arylalkyl, heteroaryl, heterocycloalkyl, aryloxy, —C(O)-heterocycloalkyl, —C(O) aryl, —CH(OH)aryl or —NH-cycloalkyl, the said groups being optionally substituted with one or more substituents chosen from a halogen atom, a hydroxyl group, a group (C1-C6)alkyl, (C1-C6)alkoxy or heterocycloalkyl or an aryloxy group;

R represents a hydrogen or halogen atom;

Z1 is absent or represents a sulfur atom, a function —NH— or —NHC(O)—, a group —S(O)—CH$_2$—, —SCH$_2$—, methylene or an ethylene group;

Z2 is absent or represents a methylene group, a group

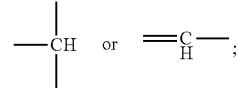

Z3 is absent or represents an oxygen atom or a methylene group, a group

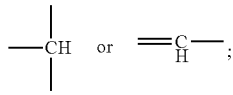

Given that Z2 represents a group

only when Z3 is present and that it represents a group

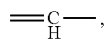

and vice versa, Z2 and Z3 thus forming a double bond;

Given that Z2 and Z3, when they are present, may be included in a cycloalkyl group;

Z4 is
 a hydrogen atom,
 a carbon atom optionally forming with Z3 a group —(C3-C10)cycloalkyl- when Z3 is a group

or
 is absent, Z3 then being a group

forming a double bond with the cyclohexyl carbon adjacent thereto;

R5 represents a hydrogen atom or an alkyl group optionally substituted with at least one hydroxyl, heterocycloalkyl(C1-C6)alkyl, amine or alkyloxy group, in the form of the acid or the base or of an addition salt with an acid or with a base.

The compounds of formula (I) may comprise one or more asymmetric carbon atoms. They may thus exist in the form of enantiomers or diastereoisomers. These enantiomers and diastereoisomers, and mixtures thereof, including racemic mixtures, form part of the invention.

In the compounds of formula (I), the substituents borne by the cyclohexyl group may be in the cis or trans position. The compounds of formula (I) may thus exist in the form of positional isomers as defined previously. These positional isomers, and also a mixture thereof, form part of the invention.

The compounds of formula (I) may exist in the form of bases or acids or salified with acids or bases, especially pharmaceutically acceptable acids or bases. Such addition salts form part of the invention.

The term "pharmaceutically acceptable base" means, for example, sodium hydroxide, potassium hydroxide, choline, lysine or arginine.

The term "pharmaceutically acceptable acid" means, for example, hydrochloric acid or sulfuric acid.

These salts are advantageously prepared with pharmaceutically acceptable bases, but the salts of other bases that are useful, for example, for purifying or isolating the compounds of formula (I) also form part of the invention.

In the context of the present invention, and unless otherwise mentioned in the text, the following definitions apply:

a halogen atom: a fluorine, chlorine, bromine or iodine atom;

an alkyl group: a saturated, linear or branched aliphatic group, possibly containing 1, 2, 3, 4, 5 or 6 carbon atoms (abbreviated as —(C1-C6)alkyl). Examples that may be mentioned include, as (i) group —C1alkyl, the methyl group, as (ii) group —C2alkyl, the ethyl group, as (iii) group —C3alkyl, the propyl or isopropyl group, as (iv) group —C4alkyl, the butyl, isobutyl or tert-butyl group, as (v) group —C5alkyl, the pentyl or isopentyl group, as (vi) group —C6alkyl, the hexyl group;

an alkylene group: a saturated, linear or branched divalent alkyl group as defined previously, possibly containing 1, 2, 3, 4, 5 or 6 carbon atoms (abbreviated as —(C1-C6) alkylene-). Examples that may be mentioned include methylene (or —CH$_2$—), ethylene (or —CH$_2$—CH$_2$—) and propylene (—CH$_2$—CH$_2$—CH$_2$—) radicals;

a cycloalkyl group: a cyclic alkyl group possibly containing 3, 4, 5, 6, 7, 8, 9 or 10 carbon atoms, also abbreviated as —(C3-C10)cycloalkyl. Examples that may be mentioned include cyclopropyl, methylcyclopropyl, cyclobutyl, cyclopentyl, cyclohexyl, adamantyl and pentalene groups;

a cycloalkyloxy group: a radical of formula —O-cycloalkyl, in which the cycloalkyl group is as defined previously;

an alkoxy or alkyloxy group: a radical —O-alkyl in which the alkyl group is as defined previously. Examples that may be mentioned include —O—(C1-C5)alkyl or —(C1-C5)alkoxy groups, and in particular, as (i) group —O—C1 alkyl, the group -Omethyl, as (ii) group —O—C2alkyl, the group -Oethyl, as (iii) group —O—C3alkyl, the group -Opropyl or -Oisopropyl, as (iv) group —O—C4alkyl, the group -Obutyl, -Oisobutyl or -Otert-butyl, as (v) group —O—C5alkyl the group -Opentyl or -Oisopentyl;

cycloalkyl-alkoxy or cycloalkyl-alkyloxy group: a radical of formula cycloalkyl-alkylene-O—, in which the cycloalkyl and alkylene groups are as defined previously;

heterocycloalkyl-alkoxy or heterocycloalkyl-alkyloxy group: a radical of formula heterocycloalkyl-alkylene-O—, in which the heterocycloalkyl and alkylene groups are as defined hereinabove and hereinbelow;

a heterocycloalkyl-alkyl: a heterocycloalkyl-alkylene-group, in which the heterocycloalkyl and alkylene groups are as defined hereinabove and hereinbelow;

an alkoxy-alkyl group: a radical of formula -alkylene-O-alkyl, in which the alkyl and alkylene groups, comprising the same number of carbons or not comprising the same number of carbons, are as defined previously. Examples that may be mentioned include the groups —(C1-C6)alkylene-O—(C1-C6)alkyl, with —(C1-C6) alkylene and —(C1-C6)alkyl as defined hereinabove;

a haloalkyl group: an alkyl group as defined above substituted with 1, 2, 3, 4 or 5 halogen atoms, as defined previously. Examples that will be mentioned include the groups -halo(C1-C5)alkyl, with (C1-C5)alkyl as defined above, and in particular the trifluoromethyl group (abbreviated as —CF$_3$);

an aryl group; a cyclic aromatic group containing 6, 7, 8, 9 or 10 carbon atoms. Examples of aryl groups that may be mentioned include the phenyl group (abbreviated as Ph) or the naphthyl group;

an arylalkyl group: an aryl group, as defined above, substituted with at least one alkyl group, as defined above. Advantageously, it is an -alkylene-aryl radical. An example that may be mentioned is the benzyl radical, i.e. the radical —CH$_2$-Ph;

an aryloxy group: a radical of formula —O-aryl, in which the aryl group is as defined previously;

a heteroaryl group: a cyclic aromatic group containing 2, 3, 4 or 5 carbon atoms and comprising 1 to 3 heteroatoms, which may be chosen from nitrogen, oxygen and sulfur atoms, independently of each other, an as to be identical or different, when there are 2 of them, or independently of each other, so as to be identical or different, when there are 3 of them. Mention may be made of pyridyl, pyrrolyl and furyl groups;

a heterocycloalkyl: an optionally bridged cyclic alkyl group, containing 5, 6 or 7 carbon atoms and comprising 1, 2 or 3 heteroatoms that may be chosen, independently of each other, so as to be identical or different, when there are 2 of them, or independently of each other, on as to be identical or different, when there are 3 of them, from a nitrogen atom, an oxygen atom and a sulfur atom. Mention may be made especially of piperidyl, piperazinyl, pyrrolidinyl, hexamethyleneimino, tetrahydrofuryl, morpholinyl and 1,1-dioxydotetrahydrothienyl groups;

the letters $\alpha$, $\beta$, $\gamma$ and $\delta$: the positions of the various carbon atoms around pyridine, when W represents a nitrogen atom in the compounds of formula (I). These letters make it possible to identify the positions of the various carbon atoms.

protecting group, such as a group R' or R" in the text hereinbelow, a group that makes it possible, firstly, to protect a reactive function such as a hydroxyl or an amine during a synthesis, and, secondly, to regenerate the intact reactive function at the end of the synthesis. Examples of protecting groups and of protection and deprotection methods are given in "Protective Groups in Organic Synthesis", Greene et al., 3$^{rd}$ Edition (John Wiley & Sons, Inc., New York). Protecting groups that may be mentioned include groups (C1-C6)alkyl, for example a benzyl, methyl, ethyl or tert-butyl group.

leaving group, in the text hereinbelow, a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a mesyl, tosyl, triflate, acetyl, etc. Examples of leaving groups and references for preparing them are given in "Advances in Organic Chemistry", J. March, 3$^{rd}$ Edition, Wiley Interscience, pp. 310-316.

Among the compounds of formula (I) that are subjects of the invention, mention may be made of a group in which:

U represents an oxygen atom or a nitrogen atom, given that when U represents an oxygen atom, then R5 is absent;
and/or
n is equal to 0, 1, 2 or 3;
and/or
p is equal to 0, 1 or 2;
and/or
D represents an oxygen atom, a group —NH— or a bond;
and/or
W represents a carbon or nitrogen atom;
and/or
X represents a heteroatom chosen from an oxygen atom and a sulfur atom;
and/or
R1, R2, R3 and R4 represent, independently of each other, a hydrogen atom,
a group —(C1-C6)alkyl, or alternatively,
(i) R1 and R2 may form, with the carbon atom to which they are attached, a group —(C3-C10)cycloalkyl- and/or (ii) R3 and R4 may form, with the carbon atom to which they are attached, a group —(C3-C10)cycloalkyl-;
and/or
Y represents a hydrogen atom, a group —(C1-C6)alkyl, —(C3-C10)cycloalkyl-, (C3-C10)cycloalkyloxy-, (C3-C10)cycloalkyl-(C1-C6)alkyloxy-, heterocycloalkyl-(C1-C6)alkyloxy-, a group —COOR1, aryl, arylalkyl, heteroaryl, heterocycloalkyl, aryloxy, —C(O)-heterocycloalkyl, —C(O)aryl, —CH(OH)aryl or —NH-cycloalkyl, the said groups being optionally substituted with one or more substituents chosen from a halogen atom, a hydroxyl group, a group (C1-C6)alkyl, (C1-C6)alkoxy or heterocycloalkyl or an aryloxy group;
and/or
R represents a hydrogen or halogen atom;
and/or
Z1 is absent or represents a sulfur atom, a function —NH—, —NHC(O)—, a group —S(O)—CH$_2$—, —SCH$_2$—, methylene or an ethylene group;
and/or
Z2 is absent or represents a methylene group, a group

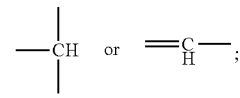

and/or
Z3 is absent or represents an oxygen atom or a methylene group, a group

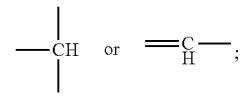

and/or
Z2 and Z3 are present and may each represent a group

and thus form a double bond;
and/or
Z2 and Z3 are present and may be included in a cycloalkyl group;
and/or
Z4 is
a hydrogen atom,
a carbon atom optionally forming with Z3 a group —(C3-C10)cycloalkyl- when Z3 is a group

—CH, or
is absent, Z3 then being a group

=C—
 H forming a double bond with the cyclohexyl carbon adjacent thereto;
and/or
R5 represents a hydrogen atom or an alkyl group optionally substituted with at least one hydroxyl, heterocycloalkyl(C1-C6)alkyl, amine or alkyloxy group,
and/or
the said compound (I) is in the form of the acid or the base or of an addition salt with an acid or with a base.

Among the compounds of formula (I) that are subjects of the invention, mention may be made of a group of compounds formed by the compounds corresponding to formula (I') below:

(I')

in which Y, R1, R2, n, Z1, X, W, R, D, Z4, Z3, Z2, R3, R4 and p are as defined above.

Among the compounds of formula (I) that are subjects of the invention, mention may be made of another group of compounds formed by the compounds corresponding to formula (I'') below:

(I'')

in which Y, R1, R2, n, Z1, X, W, R, D, Z4, Z3, Z2, R3, R4, p and R5 are as defined above.

Among the compounds of formula (I) that are subjects of the invention, mention may be made of another group of compounds in which:
D represents a bond or an oxygen atom;
and/or
p is equal to 0;
and/or
Z3 and Z2 each represent a methylene, or
Z3 represents a methylene and Z2 is absent, or
Z3 and Z2 are absent, or
Z3 and Z2 are included in a cycloalkyl group, advantageously a cyclopropyl, or
Z3 and Z2 together form a double bond;
and/or
W represents a carbon atom or a nitrogen atom;
and/or
X represents a sulfur atom.

Among the compounds of formula (I) that are subjects of the invention, mention may be made of another group of compounds in which D represents an NH group.

Among the compounds of formula (I) that are subjects of the invention, mention may be made of another group of compounds in which X represents an oxygen atom.

Among the compounds of formula (I) that are subjects of the invention, mention may be made of another group of compounds in which R1, R2, R3 and R4 represent, independently of each other, a hydrogen atom.

Among the compounds of formula (I) that are subjects of the invention, mention may be made of another group of compounds in which R1 and R2 and/or R3 and R4 form a cycloalkyl group. Advantageously. R1 and R2 and/or R3 and R4 form a cyclopropyl or cyclobutyl group.

Among the compounds of formula (I) that are subjects of the invention, mention may be made of another group of compounds in which Y is an aryl group. Advantageously, Y represents a phenyl group.

Among the compounds of formula (I) that are subjects of the invention, mention may be made of another group of compounds in which Y is a heteroaryl group. Advantageously, Y represents a pyridyl group.

Among the compounds of formula (I) that are subjects of the invention, mention may be made of another group of compounds in which Y is an aryloxy group. Advantageously, Y represents a phenoxy group.

Among the compounds of formula (I) that are subjects of the invention, mention may be made of another group of compounds in which Y is a cycloalkyl group. Advantageously, Y represents a cyclopentyl, adamantyl or pentalene group.

Among the compounds of formula (I) that are subjects of the invention, mention may be made of another group of compounds in which D is a bond and p is equal to 1.

Among the compounds of formula (I) that are subjects of the invention, mention may be made of another group of compounds in which D is an oxygen atom and p is equal to 0.

Among the compounds of formula (I) that are subjects of the invention, mention may be made of another group of compounds in which D is an NH group and p is equal to 0.

Among the compounds of formula (I) that are subjects of the invention, mention may be made of another group of compounds in which D is a bond and p is equal to 2.

Among the compounds of formula (I) that are subjects of the invention, mention may be made of another group of compounds in which Z1 is a sulfur atom.

Among the compounds of formula (I) that are subjects of the invention, mention may be made of another group of compounds in which Z3 is an oxygen atom.

Among the compounds of formula (I) that are subjects of the invention, mention may be made especially of the following compounds:

{4-[4-(5-benzyl[1,3,4]thiadiazol-2-ylcarbamoyl)phenyl]cyclohexyl}acetic acid (4-{4-[5-(4-methylbenzyl)[1,3,4]thiadiazol-2-ylcarbamoyl]phenyl}cyclohexyl)acetic acid (4-{4-[5-(2-fluorobenzyl)[1,3,4]thiadiazol-2-ylcarbamoyl]phenyl}cyclohexyl)acetic acid (4-{4-[5-(3-fluorobenzyl)[1,3,4]thiadiazol-2-ylcarbamoyl]phenyl}cyclohexyl)acetic acid (4-{4-[5-(4-fluorobenzyl)[1,3,4]thiadiazol-2-ylcarbamoyl]phenyl}cyclohexyl)acetic acid (4-{4-[5-(2,4,5-trifluorobenzyl)[1,3,4]thiadiazol-2-ylcarbamoyl]phenyl}cyclohexyl)acetic acid

[4-(4-{5-[1-(phenyl)cyclopropyl][1,3,4]thiadiazol-2-ylcarbamoyl}phenyl)cyclohexyl]-acetic acid

[4-(4-{5-[1-(4-fluorophenyl)cyclopropyl][1,3,4]thiadiazol-2-ylcarbamoyl}phenyl)cyclohexyl]acetic acid

[4-(4-{5-[1-(3-fluorophenyl)cyclobutyl][1,3,4]thiadiazol-2-ylcarbamoyl}phenyl)cyclohexyl]acetic acid (4-{4-[5-(4-chlorobenzyl)[1,3,4]thiadiazol-2-ylcarbamoyl]phenyl}cyclohexyl)acetic acid (4-{4-[5-(3-chlorobenzyl)[1,3,4]thiadiazol-2-ylcarbamoyl]phenyl}cyclohexyl)acetic acid (4-{4-[5-(2-chlorobenzyl)[1,3,4]thiadiazol-2-ylcarbamoyl]phenyl}cyclohexyl)acetic acid (4-{4-[5-(4-methoxybenzyl)[1,3,4]thiadiazol-2-ylcarbamoyl]phenyl}cyclohexyl)acetic acid {4-[4-(5-tert-butyl[1,3,4]thiadiazol-2-ylcarbamoyl)phenyl]cyclohexyl}acetic acid {4-[4-(5-adamantan-1-yl[1,3,4]thiadiazol-2-ylcarbamoyl)phenyl]cyclohexyl}acetic acid {4-[4-(5-cyclopentyl[1,3,4]thiadiazol-2-ylcarbamoyl)phenyl]cyclohexyl}acetic acid {4-[4-(5-cyclopentylmethyl[1,3,4]thiadiazol-2-ylcarbamoyl)phenyl]cyclohexyl}acetic acid (4-{4-[5-(2-cyclopentylethyl)[1,3,4]thiadiazol-2-ylcarbamoyl]phenyl}cyclohexyl)acetic acid {4-[4-(5-isobutyl[1,3,4]thiadiazol-2-ylcarbamoyl)phenyl]cyclohexyl}acetic acid {4-[4-(5-phenethyl[1,3,4]thiadiazol-2-ylcarbamoyl)phenyl]cyclohexyl}acetic acid

[4-(4-{5-[2-(4-fluorophenyl)ethyl][1,3,4]thiadiazol-2-ylcarbamoyl}phenyl)cyclohexyl]-acetic acid {4-[4-(5-phenoxymethyl[1,3,4]thiadiazol-2-ylcarbamoyl)phenyl]cyclohexyl}acetic acid

[4-(4-{5-[3-(4-fluorophenyl)propyl][1,3,4]thiadiazol-2-ylcarbamoyl}phenyl)cyclohexyl]-acetic acid (4-{4-[5-(4-fluorophenoxymethyl)[1,3,4]thiadiazol-2-ylcarbamoyl]phenyl}cyclohexyl)-acetic acid {4-[4-(5-phenyl[1,3,4]thiadiazol-2-ylcarbamoyl)phenyl]cyclohexyl}acetic acid (4-{4-[5-(3-phenoxyphenyl)[1,3,4]thiadiazol-2-ylcarbamoyl]phenyl}cyclohexyl)acetic acid {4-[4-(5-pyridin-4-yl[1,3,4]thiadiazol-2-ylcarbamoyl)phenyl]cyclohexyl}acetic acid (4-{4-[5-(3-chlorophenyl)[1,3,4]thiadiazol-2-ylcarbamoyl]phenyl}cyclohexyl)acetic acid (4-{4-[5-(3-fluorophenyl)[1,3,4]thiadiazol-2-ylcarbamoyl]phenyl}cyclohexyl)acetic acid (4-{4-[5-(4-fluorophenyl)[1,3,4]thiadiazol-2-ylcarbamoyl]phenyl}cyclohexyl)acetic acid (4-{4-[5-(4-methoxyphenyl)[1,3,4]thiadiazol-2-ylcarbamoyl]phenyl}cyclohexyl)acetic acid (4-{4-[5-(benzyl)[1,3,4]oxadiazol-2-ylcarbamoyl]phenyl}cyclohexyl)acetic acid (4-{4-[5-(4-fluorobenzyl)[1,3,4]oxadiazol-2-ylcarbamoyl]phenyl}cyclohexyl)acetic acid cis-4-[4-(5-benzyl[1,3,4]thiadiazol-2-ylcarbamoyl)phenoxy]cyclohexanecarboxylic acid trans-4-[4-(5-benzyl[1,3,4]thiadiazol-2-ylcarbamoyl)phenoxy]cyclohexanecarboxylic acid trans-4-[4-(5-phenyl[1,3,4]thiadiazol-2-ylcarbamoyl)phenoxy]cyclohexanecarboxylic acid cis-4-[4-(5-benzyl[1,3,4]thiadiazol-2-ylcarbamoyl)-2-fluorophenoxy]cyclohexanecarboxylic acid cis-4-[4-(5-benzyl[1,3,4]thiadiazol-2-ylcarbamoyl)-2-chlorophenoxy]cyclohexanecarboxylic acid cis-4-{4-[5-(2-cyclopentylethyl)[1,3,4]thiadiazol-2-ylcarbamoyl]phenoxy}cyclohexanecarboxylic acid cis-4-[4-(5-phenyl[1,3,4]thiadiazol-2-ylcarbamoyl)phenoxy]cyclohexanecarboxylic acid cis-4-{4-[5-(3-chlorophenyl)[1,3,4]thiadiazol-2-ylcarbamoyl]phenoxy}cyclohexanecarboxylic acid cis-4-{4-[5-(3-chlorophenyl)[1,3,4]thiadiazol-2-ylcarbamoyl]-2-fluorophenoxy}cyclohexanecarboxylic acid cis-4-[4-([1,3,4]thiadiazol-2-ylcarbamoyl)phenoxy]cyclohexanecarboxylic acid cis-4-[5-(5-benzyl[1,3,4]thiadiazol-2-ylcarbamoyl)pyridin-2-yloxy]cyclohexanecarboxylic acid cis-4-{5-[5-(3-chlorobenzyl)[1,3,4]thiadiazol-2-ylcarbamoyl]pyridin-2-yloxy}cyclohexanecarboxylic acid cis-4-[5-(5-phenethyl[1,3,4]thiadiazol-2-ylcarbamoyl)pyridin-2-yloxy]cyclohexanecarboxylic acid cis-4-[5-(5-phenyl[1,3,4]thiadiazol-2-ylcarbamoyl)pyridin-2-yloxy]cyclohexanecarboxylic acid cis-4-{5-[5-(3-chlorophenyl)[1,3,4]thiadiazol-2-ylcarbamoyl]pyridin-2-yloxy}cyclohexanecarboxylic acid cis-4-[4-(5-benzyl[1,3,4]thiadiazol-2-ylcarbamoyl)phenylamino]cyclohexanecarboxylic acid trans-4-[4-(5-benzyl[1,3,4]thiadiazol-2-ylcarbamoyl)phenylamino]cyclohexanecarboxylic acid trans-{4-[4-(5-benzyl[1,3,4]thiadiazol-2-ylcarbamoyl)phenyl]cyclohexyl}acetic acid
trans-4-[4-(5-benzyl[1,3,4]thiadiazol-2-ylcarbamoyl)phenyl]cyclohexanecarboxylic acid
trans-(4-{4-[5-(3-methoxyphenyl)[1,3,4]thiadiazol-2-ylcarbamoyl]phenyl}cyclohexyl)-acetic acid
trans-(4-{4-[5-(3-hydroxyphenyl)[1,3,4]thiadiazol-2-ylcarbamoyl]phenyl}cyclohexyl)-acetic acid
trans-{4-[4-(5-cyclopentyloxymethyl[1,3,4]thiadiazol-2-ylcarbamoyl)phenyl]cyclohexyl}-acetic acid
trans-[4-(4-{5-[2-(tetrahydrofuran-2-yl)ethyl][1,3,4]thiadiazol-2-ylcarbamoyl}phenyl)-cyclohexyl]acetic acid
trans-(4-{4-[5-(2-cyclohexylethyl)[1,3,4]thiadiazol-2-ylcarbamoyl]phenyl}cyclohexyl)-acetic acid
trans-{4-[4-(5-cyclopentylmethoxymethyl[1,3,4]thiadiazol-2-ylcarbamoyl)phenyl]cyclohexyl}acetic acid
trans-{4-[4-(5-benzylsulfanyl[1,3,4]thiadiazol-2-ylcarbamoyl)phenyl]cyclohexyl}acetic acid
{4-[4-(5-benzyl[1,3,4]thiadiazol-2-ylcarbamoyl)phenyl]cyclohexylidene}acetic acid
6-[4-(5-benzyl[1,3,4]thiadiazol-2-ylcarbamoyl)phenyl]spiro[2.5]octane-1-carboxylic acid
(E)-3-{4-[4-(5-benzyl[1,3,4]thiadiazol-2-ylcarbamoyl)phenyl]cyclohexyl}acrylic acid
trans-(1R,2S/1S,2R)-2-{4-[4-(5-benzyl[1,3,4]thiadiazol-2-ylcarbamoyl)phenyl]cyclohexyl}cyclopropanecarboxylic acid
trans-3-{4-[4-(5-benzyl[1,3,4]thiadiazol-2-ylcarbamoyl)phenyl]cyclohexyl}propionic acid
(4-{4-[5-((1S,3S/1R,3R)-3-phenoxycyclohexyl)[1,3,4]thiadiazol-2-ylcarbamoyl]phenyl}-cyclohexyl)acetic acid
trans-(4-{4-[(5-{[(3R,6S/3S,6R)-5-ethoxyoctahydropentalen-2-yl]methyl}-1,3,4-thiadiazol-2-yl)carbamoyl]phenyl}cyclohexyl)acetic acid
trans-{4-[4-(5-benzyl[1,3,4]thiadiazol-2-ylcarbamoyl)phenyl]cyclohexyloxy}acetic acid
trans-{4-[4-(5-bromo-[1,3,4]thiadiazol-2-ylcarbamoyl)phenyl]cyclohexyl}acetic acid
trans-(4-{4-[5-(2-morpholin-4-ylethyl)[1,3,4]thiadiazol-2-ylcarbamoyl]phenyl}cyclohexyl)acetic acid
trans-{4-[4-(5-morpholin-4-yl[1,3,4]thiadiazol-2-ylcarbamoyl)phenyl]cyclohexyl}acetic acid
trans-5-[4-(4-carboxymethylcyclohexyl)benzoylamino][1,3,4]thiadiazole-2-carboxylic acid
trans-(4-{4-[5-(2-oxo-2-pyrrolidin-1-ylethyl)[1,3,4]thiadiazol-2-ylcarbamoyl]phenyl}-cyclohexyl)acetic acid
cis-4-[4-(5-cyclopentyloxymethyl[1,3,4]thiadiazol-2-ylcarbamoyl)phenoxy]cyclohexanecarboxylic acid.
trans-[4-(4-{5-[2-(tetrahydrofuran-3-yl)ethyl][1,3,4]thiadiazol-2-ylcarbamoyl}phenyl)-cyclohexyl]acetic acid
trans-(4-{4-[5-(3-phenylcyclobutyl)[1,3,4]thiadiazol-2-ylcarbamoyl]phenyl}cyclohexyl)acetic acid
{4-[4-(5-phenylacetylamino[1,3,4]thiadiazol-2-ylcarbamoyl)phenyl]cyclohexyl}acetic acid
trans-{4-[4-(5-cyclopentyloxymethyl[1,3,4]thiadiazol-2-ylcarbamoyl)phenyl]cyclohexyl}-acetic acid
trans-(4-{4-[5-(3,5-difluorobenzyl)[1,3,4]thiadiazol-2-ylcarbamoyl]phenyl}cyclohexyl)-acetic acid
trans-(4-{4-[5-(4-hydroxycyclohexylmethyl)[1,3,4]thiadiazol-2-ylcarbamoyl]phenyl}-cyclohexyl)acetic acid
trans-(4-{4-[5-(tetrahydrofuran-2-ylmethoxymethyl)[1,3,4]thiadiazol-2-ylcarbamoyl]-phenyl}cyclohexyl)acetic acid
trans-{4-[4-(5-benzyl[1,3,4]thiadiazol-2-ylcarbamoyl)phenoxy]cyclohexyl}acetic acid
trans-4-{4-[5-(tetrahydrofuran-2-ylmethoxymethyl)[1,3,4]thiadiazol-2-ylcarbamoyl]-phenoxy}cyclohexanecarboxylic acid
trans-(4-{4-[5-(3-oxo-3-phenylpropyl)[1,3,4]thiadiazol-2-ylcarbamoyl]phenyl}cyclohexyl)acetic acid
trans-(4-{4-[5-(3-hydroxy-3-phenylpropyl)[1,3,4]thiadiazol-2-ylcarbamoyl]phenyl}cyclohexyl)acetic acid
trans-(1S,2R)-2-(4-{4-[5-(3-chlorophenyl)[1,3,4]thiadiazol-2-ylcarbamoyl]phenyl}cyclohexyl)cyclopropanecarboxylic acid
trans-N-(5-benzyl[1,3,4]thiadiazol-2-yl)-4-{4-[(2-hydroxy-2-methylpropylcarbamoyl)-methyl]cyclohexyl}benzamide
trans-N-(5-benzyl[1,3,4]thiadiazol-2-yl)-4-(4-carbamoylmethylcyclohexyl)benzamide
trans-N-(5-benzyl[1,3,4]thiadiazol-2-yl)-4-{4-[(2,3-dihydroxypropylcarbamoyl)methyl]-cyclohexyl}benzamide
trans-N-(5-benzyl[1,3,4]thiadiazol-2-yl)-4-{4-[(2-morpholin-4-ylethylcarbamoyl)methyl]-cyclohexyl}benzamide
trans-N-(5-benzyl[1,3,4]thiadiazol-2-yl)-4-{4-[(2-dimethylaminoethylcarbamoyl)methyl]-cyclohexyl}benzamide
trans-N-(5-benzyl[1,3,4]thiadiazol-2-yl)-4-{4-[(2-methoxyethylcarbamoyl)methyl]cyclohexyl}benzamide
trans-{4-[4-(5-cyclopentylamino[1,3,4]thiadiazol-2-ylcarbamoyl)phenyl]cyclohexyl}-acetic acid
trans-N-(5-benzyl[1,3,4]thiadiazol-2-yl)-4-(4-{[([1,4]dioxan-2-ylmethyl)carbamoyl]-methyl}cyclohexyl)benzamide
trans-4-{4-[5-(3,5-difluorobenzyl)[1,3,4]thiadiazol-2-ylcarbamoyl]phenoxy}cyclohexanecarboxylic acid
trans-{4-[4-(5-phenylmethanesulfinylmethyl[1,3,4]thiadiazol-2-ylcarbamoyl)phenyl]-cyclohexyl}acetic acid
trans-{4-[4-(5-benzylsulfanylmethyl[1,3,4]thiadiazol-2-ylcarbamoyl)phenyl]cyclohexyl}-acetic acid
trans-(4-{4-[5-(3-phenylcyclobutyl)[1,3,4]thiadiazol-2-ylcarbamoyl]phenyl}cyclohexyl)-acetic acid
cis-4-[5-(5-cyclopentyloxymethyl[1,3,4]thiadiazol-2-ylcarbamoyl)pyridin-2-yloxy]cyclohexanecarboxylic acid
trans-(4-{4-[5-(2-cyclopentylaminoethyl)[1,3,4]thiadiazol-2-ylcarbamoyl]phenyl}cyclohexyl)acetic acid
cis-4-(4-{5-[2-(3-morpholin-4-ylcyclopentyl)ethyl][1,3,4]thiadiazol-2-ylcarbamoyl}-phenoxy)cyclohexanecarboxylic acid
cis-4-[4-(5-cyclopentylamino[1,3,4]thiadiazol-2-ylcarbamoyl)phenoxy]cyclohexanecarboxylic acid
cis-4-{4-[5-(3-oxo-3-phenylpropyl)[1,3,4]thiadiazol-2-ylcarbamoyl]phenoxy}cyclohexanecarboxylic acid.

The invention is also directed towards a process for preparing a compound of formula (I) as defined previously, characterized in that the ester function of a compound chosen from (i) a compound of formula (V)

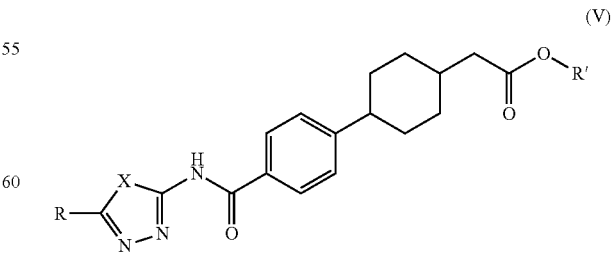

(V)

in which R represents a group —C(R1R2)n-Y and X. Y. R1, R2 and n are as defined previously and R' represents a protecting group; and (ii) a compound of formula (XXIII):

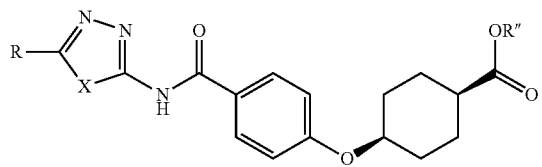

in which R represents a group —C(R1R2)n-Y and X, Y, R1, R2 and n are as defined previously and R" represents a protecting group,
is deproteoted.

According to one embodiment, the production of the compound of formula (V), is performed by reacting (i) a compound of formula (II):

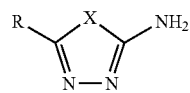

in which R represents a group —C(R1R2)n-Y and X, Y, R1, R2 and n are as defined previously, with (ii) a compound of formula (III)

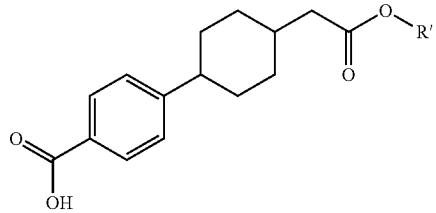

in which R' represents a protecting group.

According to one embodiment, the production of the compound of formula (XXIII), is performed by reacting (i) a compound of formula (II):

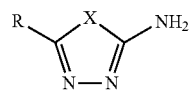

in which R represents a group —C(R1R2)n-Y and X. Y. R1, R2 and n are as defined previously, with (ii) a compound of formula (XXI)

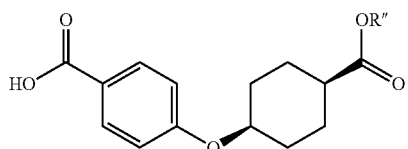

in which R" represents a protecting group.

In Schemes 1 to 21, the starting compounds and the reagents, when their mode of preparation is not described, are commercially available or are described in the literature, or else may be prepared according to methods that are described therein or that are known to those skilled in the art.

In accordance with the invention, the compounds of general formula (I) may be prepared according to the following processes.

The group R used hereinbelow represents a group —Z1-C(R1R2)$_n$—Y with R1, R2, Y, n and Z1 as defined previously.

Scheme 1 describes the synthesis of the compounds of formula (I) in which D is a bond, n=0 and p=1; these compounds will be referred to hereinbelow as compounds of formula (Ia).

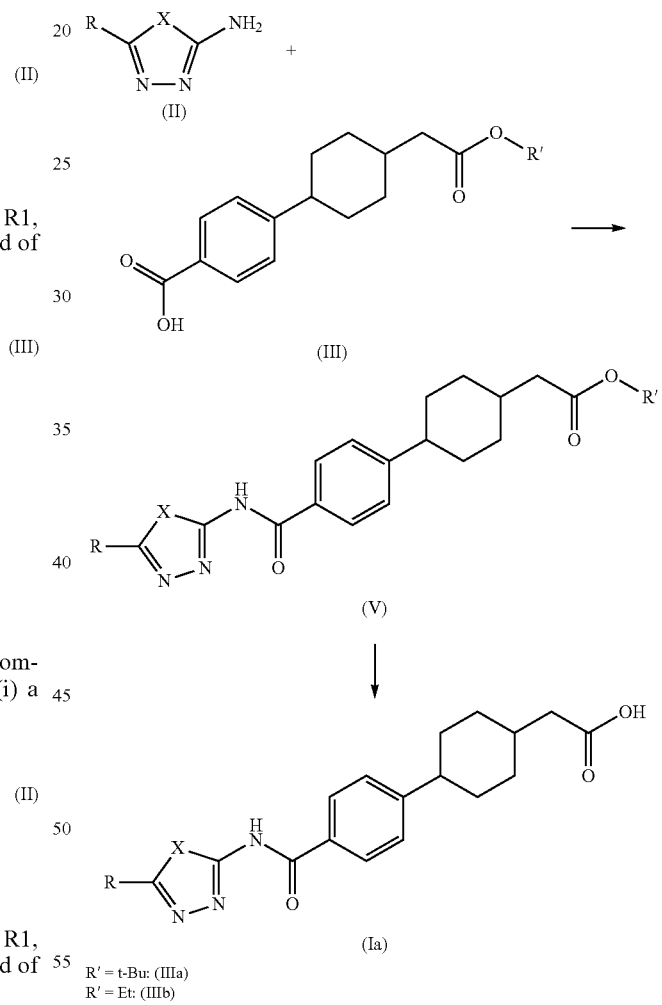

In Scheme 1, the intermediates of formula (V), for which R and X are as defined previously and R' is a protecting group such as a group (C1-C6)alkyl, for example an ethyl or tert-butyl group, are obtained by coupling the acid of formula (III) with the aminothiadiazoles or aminooxadiazoles of formula (II) in the presence of a coupling agent (for example bromo-tris-pyrrolidinophosphonium)hexafluorophosphonate) in a polar solvent such as dimethylformamide or acetonitrile, at between 20 and 100° C. The acids of formula (Ia) are obtained by deprotecting the esters of formula (V) via methods chosen from those known to a person skilled in the art, these methods taking into account the stability of the compound of formula (V) in acidic medium. They include, inter alia, the use of trifluoroacetic acid or hydrochloric acid in a polar solvent such as dichloromethane or dioxane at room temperature for the tert-butyl ester or lithium hydroxide in a mixture of polar solvents such as water, methanol or tetrahydrofuran for the ethyl ester.

Scheme 2 details a synthesis of the compounds of formula (VIII) for which X represents a sulfur atom; these compounds will be referred to hereinbelow as compounds of formula (IIa).

Scheme 2

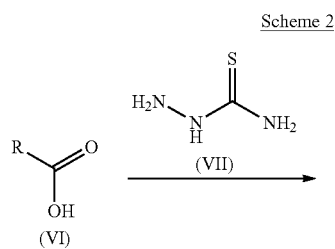

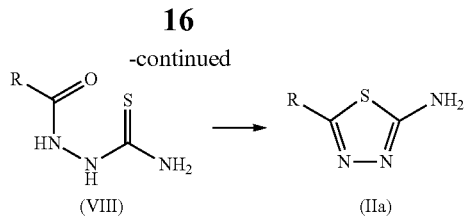

In Scheme 2, the compounds of formula (VIII) may be prepared by reacting a carboxylic acid and thiosemicarbazide in the presence of a coupling agent (for example 1-ethyl-3-(3-dimethylaminopropyl)carbodiimide) in a polar solvent such as dichloromethane or dimethylformamide at room temperature. The derivatives of formula (VIII) are then cyclized in an acid such as sulfuric acid at room temperature to give the aminothiadiazoles of formula (IIa).

It should be noted that certain compounds of general formula (II) for which X represents a sulfur or oxygen atom are commercially available.

Certain compounds of general formula (VI) are described in the literature (J. Org. Chem. 1968, 1959; J. Org. Chem. 1962, 1947).

Scheme 3 details a synthesis of the compounds of formula (III) for which R' represents a tert-butyl group. These compounds will be referred to hereinbelow as compounds of formula (IIIa).

Scheme 3

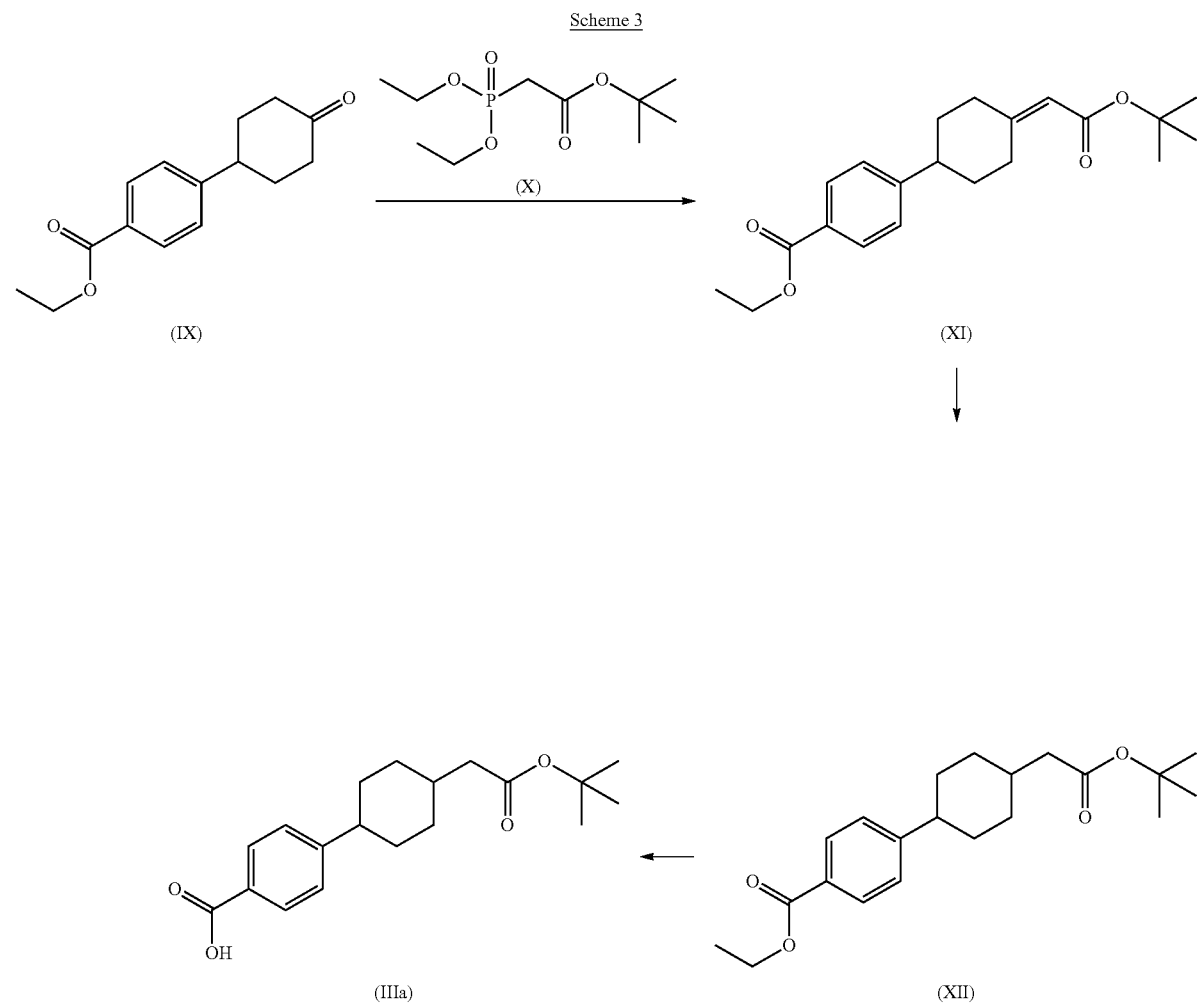

In Scheme 3, the compound of formula (XI) is prepared via a Horner-Wadsworth-Emmons reaction starting with the derivatives of formulae (IX) and (X) in a polar solvent such as dimethylformamide or tetrahydrofuran at room temperature. Compound (XI) is hydrogenated in the presence of a transition metal such as palladium in a polar solvent such as ethanol to give the compound of formula (XII). The acid of formula (IIIa) is obtained by hydrolysis of the ester of formula (XII) in the presence of lithium hydroxide in a mixture of polar solvents such as water, methanol and tetrahydrofuran.

The compound of formula (IX) may be prepared according to a scheme described in the literature (WO 2003/099 772).

Scheme 4 details a synthesis of the compounds for which R' represents an ethyl group. These compounds will be referred to hereinbelow as compounds of formula (IIIb).

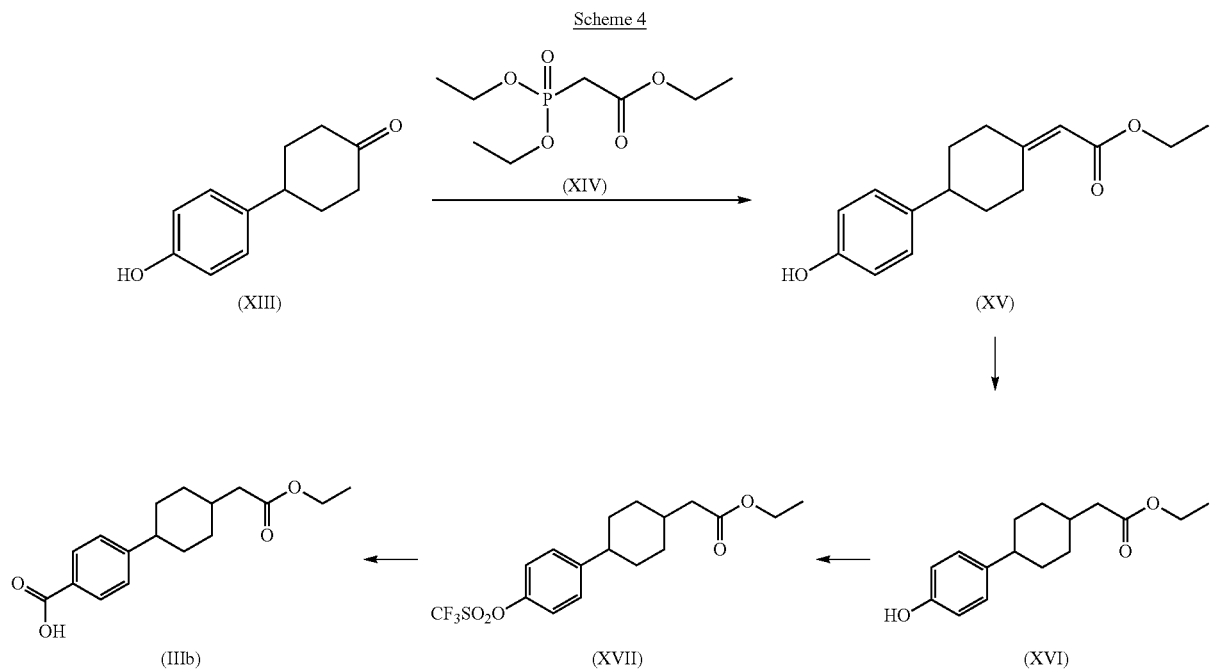

In Scheme 4, the compound of formula (XV) is prepared via a Horner-Wadsworth-Emmons reaction starting with the derivatives of formulae (XIII) and (XIV) in a polar solvent at room temperature. The compound of formula (XV) is hydrogenated in the presence of a transition metal such as palladium in a polar solvent such as ethanol or ethyl acetate to give the compound of formula (XVI). The compound of formula (XVI) is converted into the acid of formula (IIIb) in a polar solvent such as dichloromethane at between 0 and 25° C., followed by hydroxycarbonylation of the intermediate of formula (XVII) in a polar solvent such as dioxane at between 100 and 120° C.

Scheme 5 describes the synthesis of the compounds of formula (I) in which D is an oxygen atom and p=0; these compounds will be referred to hereinbelow as compounds of formula (Ib).

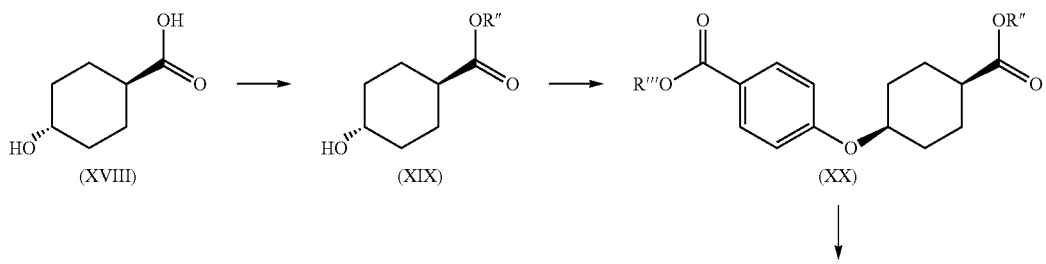

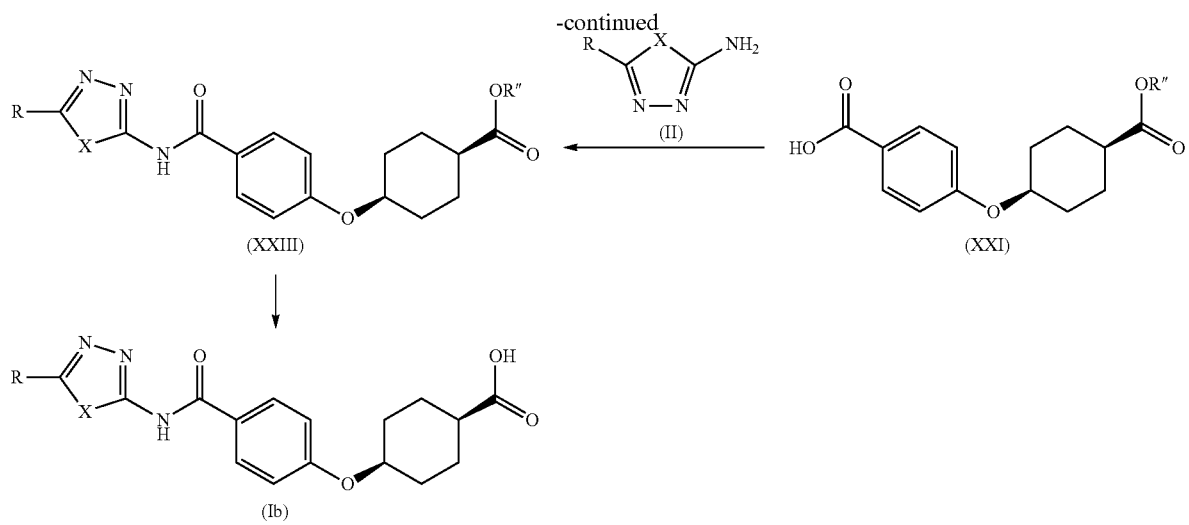

In Scheme 5, the compound of formula (XIX) for which R'" is a protecting group such as a (C1-C6)alkyl group, for example a methyl group, is obtained from the acid of formula (XVIII) by selective reaction with a compound known to those skilled in the art, such as trimethylsilyldiazomethane in a mixture of apolar and polar solvents such as, respectively, toluene and methanol, at room temperature. The alcohol of formula (XIX), in which R" is a (C1-C6)alkyl group such as a tert-butyl group, is employed in a Mitsunobu reaction with an alcohol of the type such as a (C1-C6)alkyl 4-hydroxybenzoate, for example tert-butyl 4-hydroxybenzoate, in a polar solvent such as tetrahydrofuran at room temperature, to give the ether of formula (XX). The acid of formula (XXI) is obtained by deprotecting the ester function —COOR'" of the compound of formula (XX) via methods chosen from those known to a person skilled in the art. They include, inter alia, the use of trifluoroacetic acid or hydrochloric acid in polar solvents such as dichloromethane or dioxane. The intermediates of formula (XXIII) are obtained by coupling the acid of formula (XXI) with the aminothiadiazoles or aminooxadiazoles of formula (II) in the presence of a coupling agent (for example bromotris-pyrrolidinophosphonium hexafluorophosphonate) in a polar solvent such as dimethylformamide or acetonitrile, at room temperature. The acids of formula (Ib) are obtained after deprotecting the ester of formula (XXIII) via methods chosen from those known to a person skilled in the art. They include, inter alia, the use of lithium hydroxide in a mixture of polar solvents such as water and tetrahydrofuran.

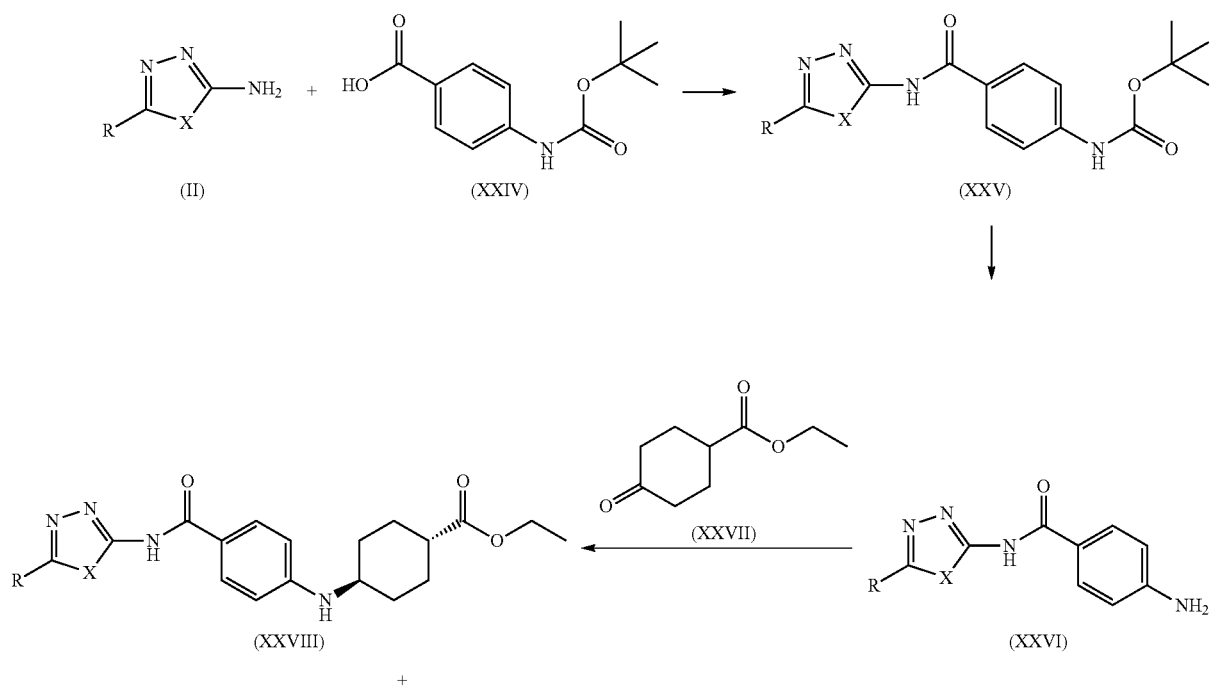

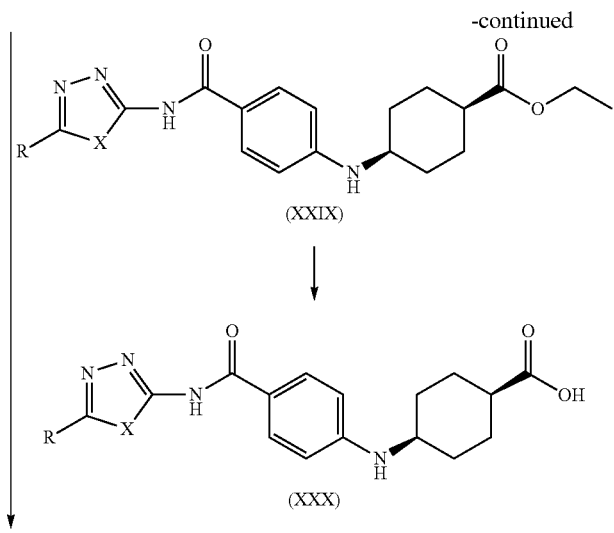

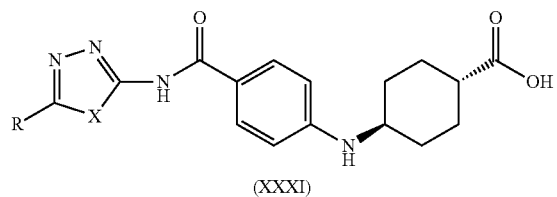

In Scheme 6, the intermediates of formula (XXV) are obtained by coupling the acid of formula (XXIV) with the aminothiadiazoles or aminooxadiazoles of formula (II) in the presence of a coupling agent (for example 1-ethyl-3-(3-dimethylaminopropyl)-carbodiimide) in a polar solvent such as dimethylformamide or acetonitrile at room temperature, via methods chosen from those known to a person skilled in the art. Deprotection of the carbamate of formula (XXV) to the amine of formula (XXVI) is performed via methods chosen from those known to a person skilled in the art. They include, inter alia, the use of trifluoroacetic acid or hydrochloric acid in polar solvents such as dichloromethane or dioxane. The reductive amination of the cyclohexanone (XXVII) with the amine of formula (XXVI) takes place in the presence of a hydride donor such as sodium triacetoxyborohydride in a polar solvent such as dichloromethane, via methods chosen from those known to a person skilled in the art. The aminocyclohexyls (XXVIII) and (XXIX) obtained are separated by chromatography. The acids of formulae (XXX) and (XXXI) are obtained by respective deprotection of the esters of formulae (XXVIII) and (XXIX) using lithium hydroxide in a mixture of polar solvents such as water, methanol or tetrahydrofuran.

Scheme 7

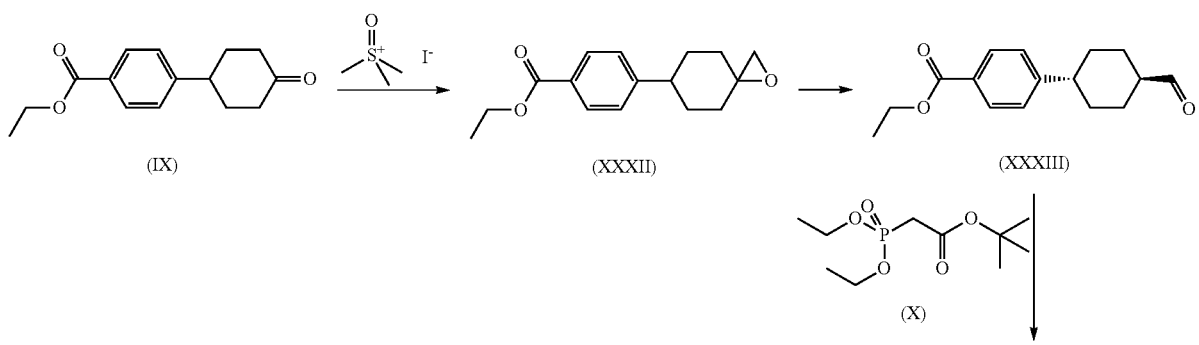

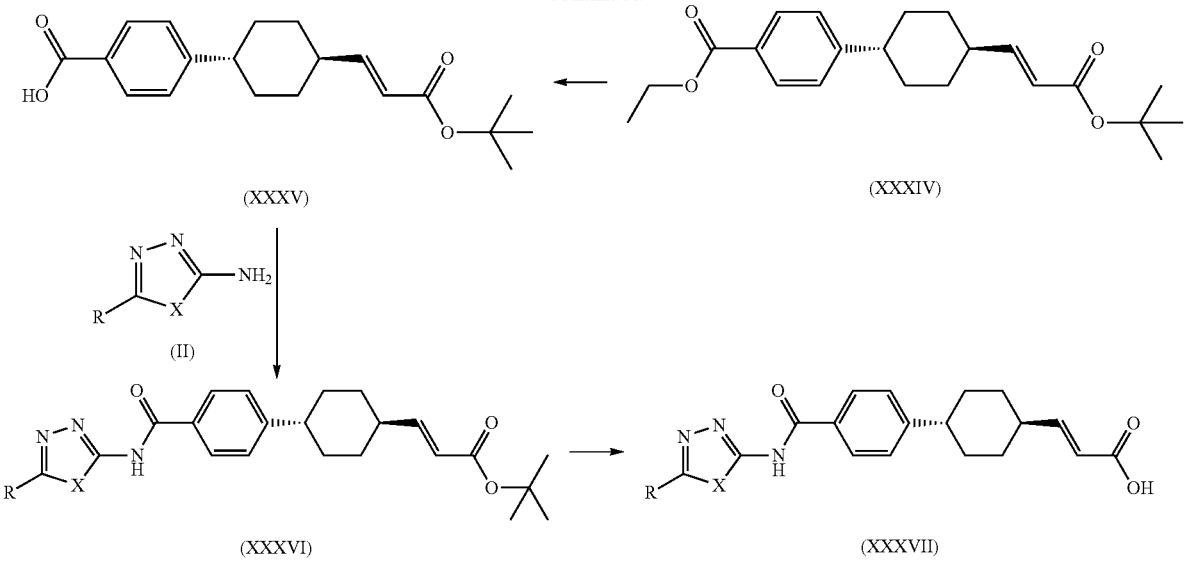

In Scheme 7, compound (XXXII) is prepared from the ketone (IX) via an epoxidation reaction with trimethylsulfoxonium iodide in a polar solvent such as DMSO at temperatures of between room temperature and 50° C. Compound (XXXII) is converted into the aldehyde (XXXIII) via the action of a Lewis acid such as boron trifluoride etherate in a polar solvent such as dichloromethane. The compound of formula (XXXIV) is prepared via a Horner-Wadsworth-Emmons reaction from the derivative (XXXIII) and the phosphonate (X) in a polar solvent such as dimethylformamide or tetrahydrofuran at room temperature in the presence of a base such as sodium hydride. The acids of formula (XXXV) are obtained by deprotection of the esters of formula (XXXIV) with an alkaline base such as lithium hydroxide in a mixture of polar solvents such as water, methanol or tetrahydrofuran. The intermediates of formula (XXXVI) are obtained by coupling the acid of formula (XXXV) with the aminothiadiazoles or aminooxadiazoles of formula (II) in the presence of a coupling agent (for example bromotris-pyrrolidinophosphonium hexafluorophosphonate) in a polar solvent such as dimethylformamide or acetonitrile at room temperature. The acids of formula (XXXVII) are obtained by hydrolysis of the esters of formula (XXXVI) in the presence of trifluoroacetic acid or hydrochloric acid in a polar solvent such as dichloromethane or dioxane at room temperature.

Scheme 8

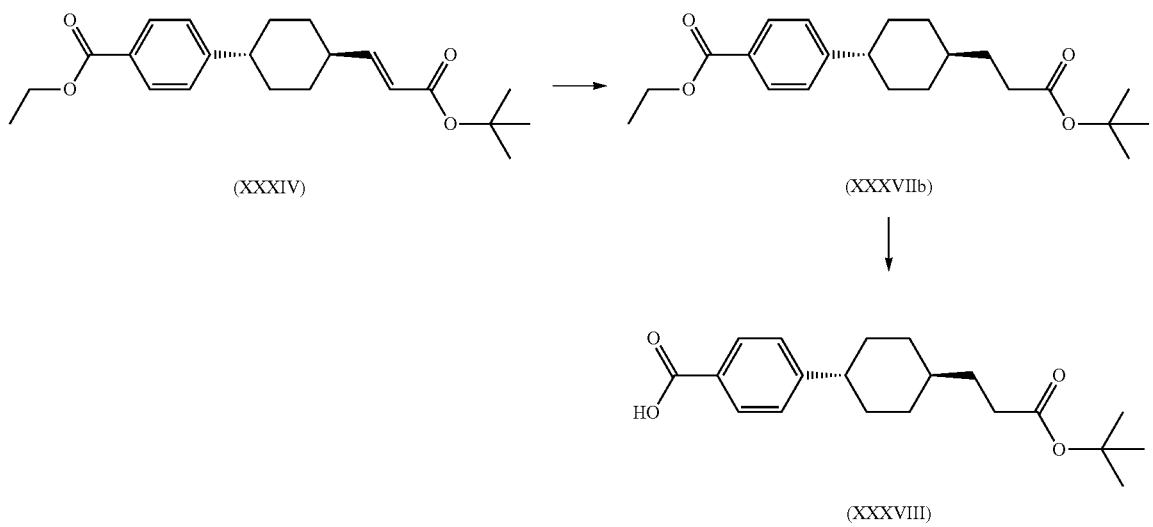

In Scheme 8, compound (XXXIV) is hydrogenated in the presence of a transition metal such as palladium in a polar solvent such as ethanol to give compound (XXXVIIb). The acid (XXXVIII) is obtained by deprotecting the ester (XXXVIIb) with an alkaline base such as lithium hydroxide in a mixture of polar solvents such as water, methanol or tetrahydrofuran, Scheme 9

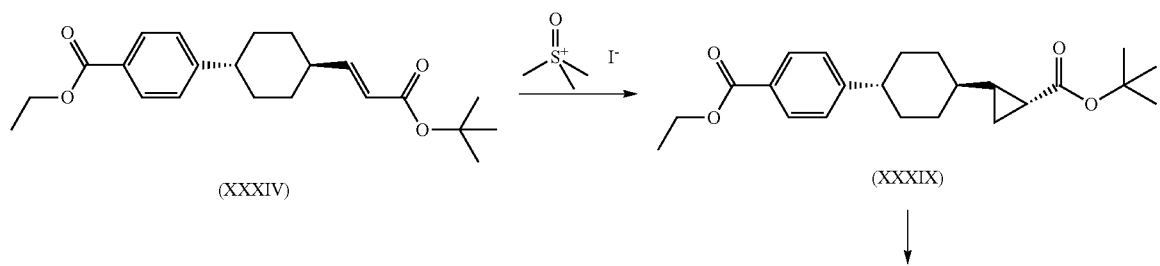

In Scheme 9, compound (XXXIV) is used in a cyclopropanation reaction with trimethylsulfoxonium iodide in a polar solvent such as DMSO at room temperature to give compound (XXXIX). The acid (XL) is obtained by deprotecting the ester (XXXIX) with an alkaline base such as lithium hydroxide in a mixture of polar solvents such as water, methanol or tetrahydrofuran.

Scheme 10

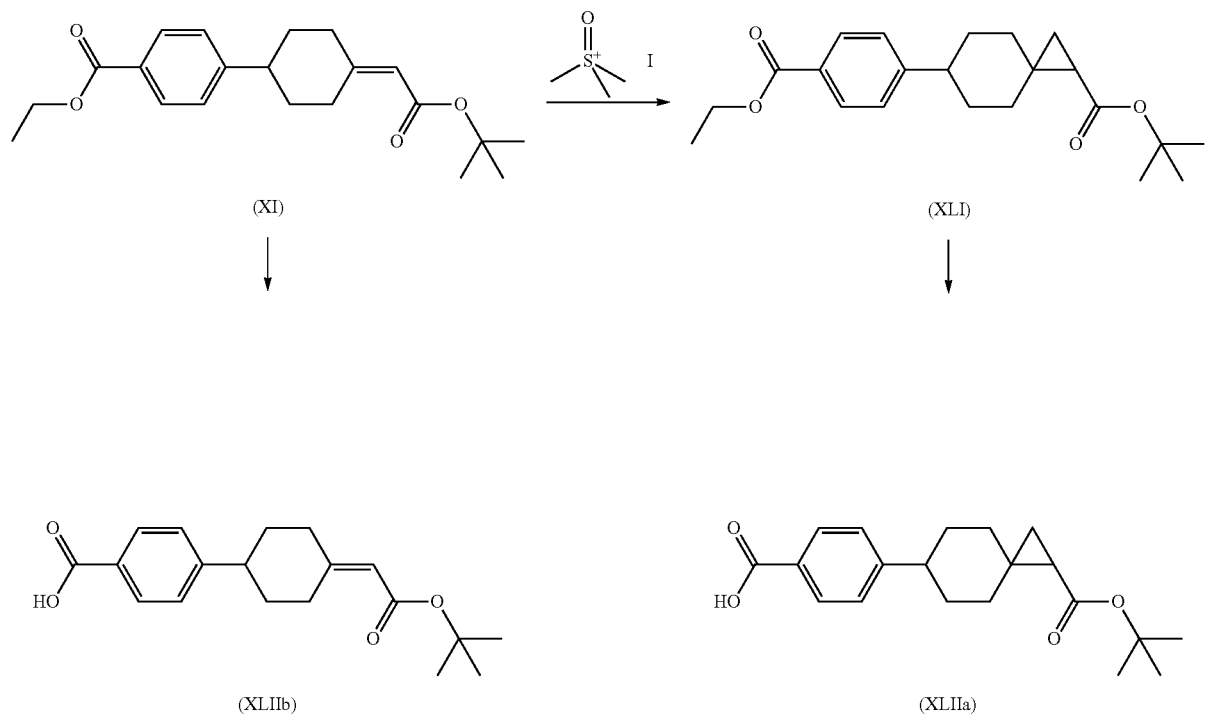

In Scheme 10, compound (XI) is used in a cyclopropanation reaction with trimethylsulfoxonium iodide in a polar solvent such as DMSO at room temperature to give compound (XLI). The acids (XLIIa) and (XLIIb) are obtained, respectively, by deprotection of the esters (XLI) and (XI) with an alkaline base such as lithium hydroxide in a mixture of polar solvents such as water, methanol or tetrahydrofuran.

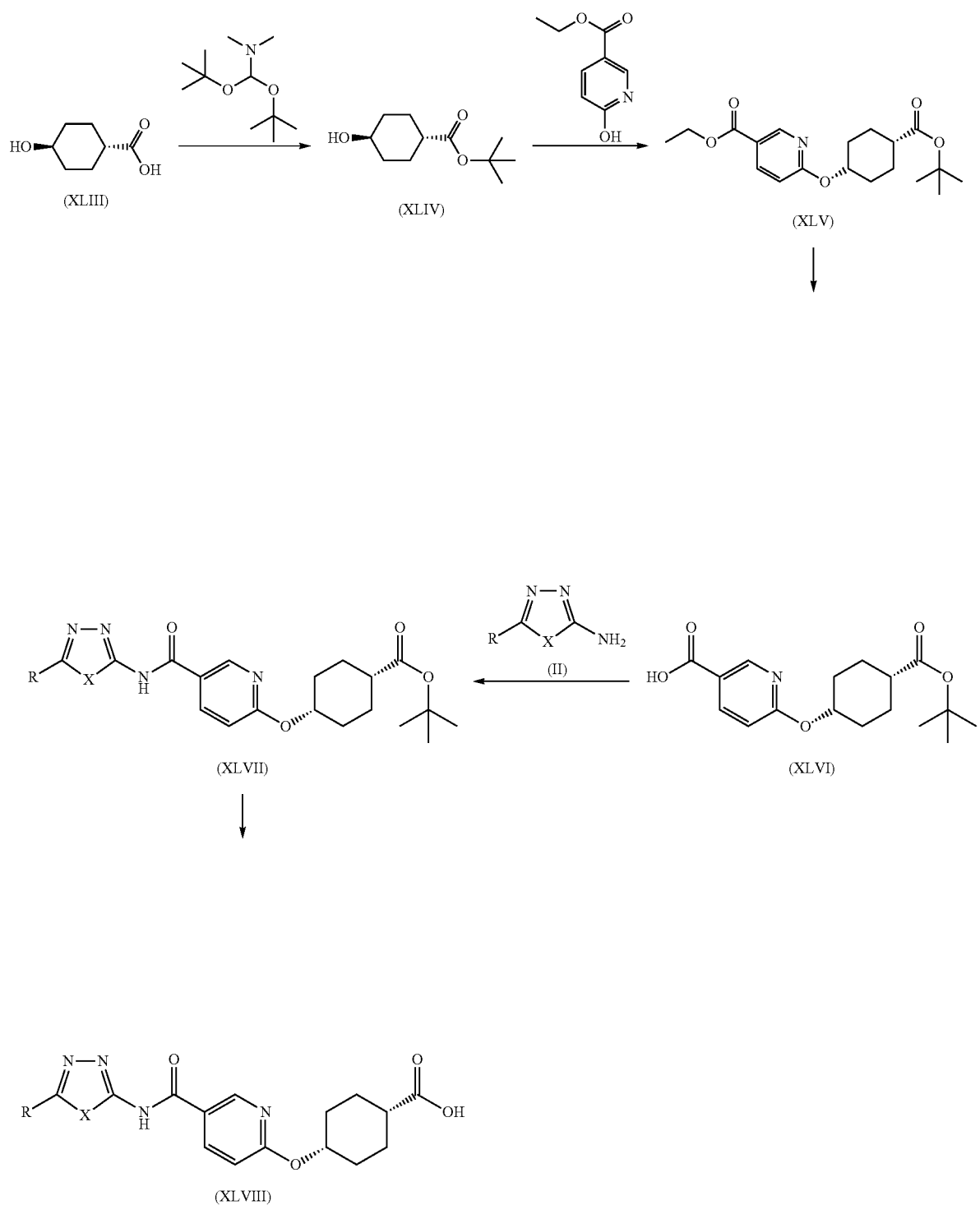

In Scheme 11 the compound of formula (XLIV) is obtained from the acid of formula (XLIII) by selective reaction with a compound known to those skilled in the art, such as bis(di-tert-butoxymethyl)-N,N-dimethylmethylamine in an apolar solvent such as refluxing toluene. The alcohol of formula (XLIV) is employed in a Mitsunobu reaction with an alcohol such as ethyl 6-hydroxynicotinate in a polar solvent such as tetrahydrofuran at room temperature to give the ether of formula (XLV). The acid of formula (XLVI) is obtained by deprotecting the ester (XLV) with an alkaline base such as lithium hydroxide in a mixture of polar solvents such as water, methanol or tetrahydrofuran. The intermediates of formula (XLVII) are obtained by coupling the acid of formula (XLVI) with the aminothiadiazoles or the aminooxadiazoles of formula (II) in the presence of a coupling agent (for example bromotris-pyrroiidinophosphonium hexafluorophosphonate) in a polar solvent such as dimethylformamide or acetonitrile at room temperature. The acids of formula (XLVIII) are obtained by hydrolysis of the esters of formula (XLVII) in the presence of trifluoroacetic acid or hydrochloric acid in a polar solvent such as dichloromethane or dioxane at room temperature.

In Scheme 12, compound (XLIX) is protected with allyl bromide in a polar solvent such as acetone or DMF to give compound (L). Alkylation of compound (L) to the intermediate (LI) is performed with an alkyl haloacetate such as tert-butyl bromoacetate via methods chosen from those known to a person skilled in the art. They include, inter alia, the use of a phase-transfer catalyst such as tetrabutylammonium hydrogen sulfate and the use of a base such as sodium hydroxide in aqueous solution in an apolar solvent such as toluene. The deprotection of the intermediate (LI) to the phenol (LII) is performed via methods chosen from those known to a person skilled in the art. They include, inter alia, the use of a palladium catalyst such as tetrakis(triphenylphosphine)palladium in a polar solvent such as dichloromethane. The phenol (LII) is converted into the triflate (LIII) using a reagent such as triflic anhydride in a polar solvent such as dichloromethane at between 0 and 25° C. in the presence of a base such as triethylamine. The ester (LIV) is obtained by hydroxycarbonylation of the triflate (LIII) in a polar solvent such as dioxane, at between 100 and 120° C., of the intermediate of formula (LIII) via methods chosen from those known to a person skilled in the art. They include, inter alia, the use

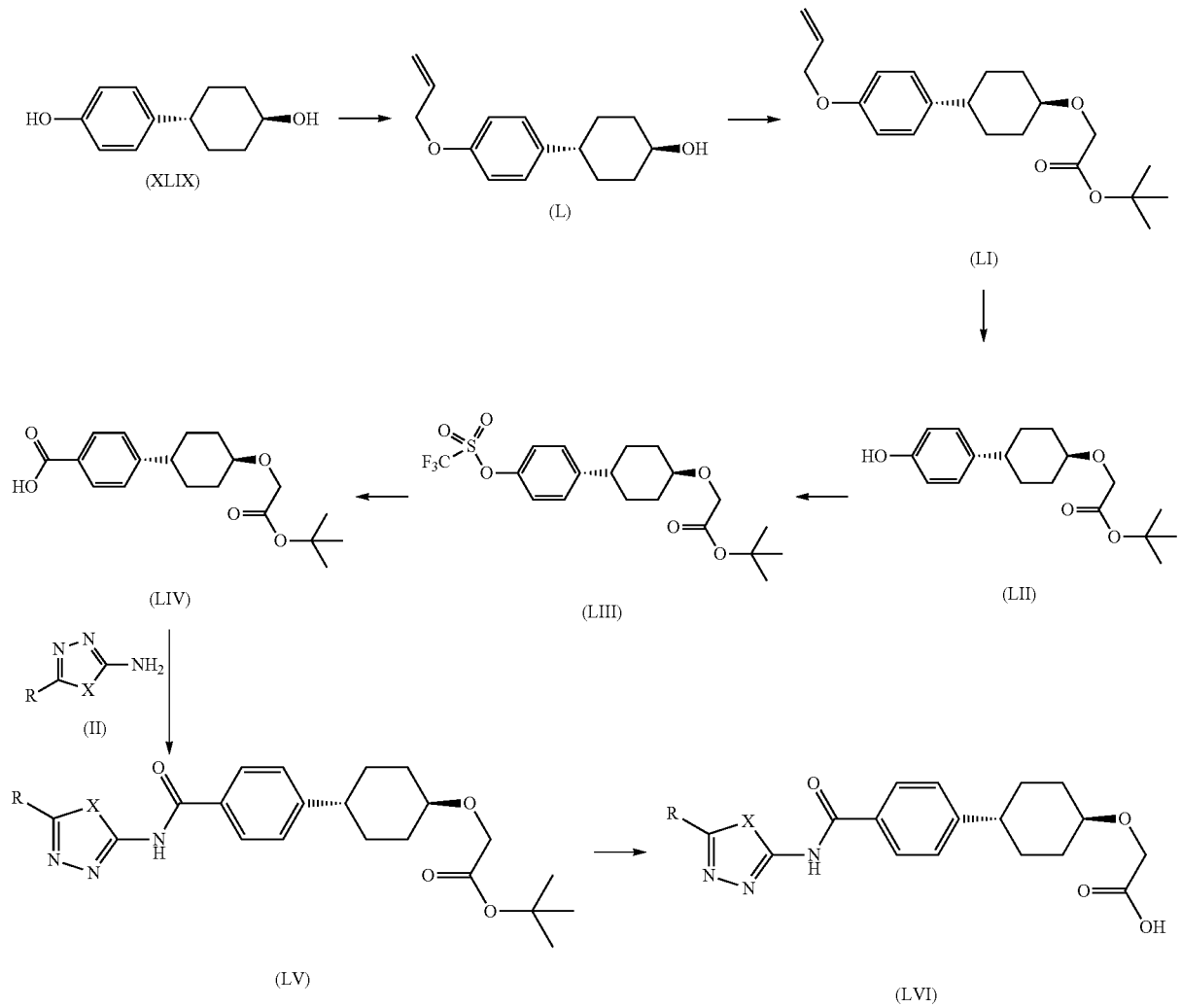

Scheme 12 of a carbonylation reagent such as molybdenum hexacarbonyl and a palladium catalyst such as palladium diacetate in a polar solvent such as dioxane. The intermediates of formula (LV) are obtained by coupling the acid of formula (LIV) with the aminothiadiazoles or aminooxadiazoles of formula (II) in the presence of a coupling agent (for example 1-ethyl-3-(3-dimethylaminopropyl)carbodiimide) in a polar solvent such as dimethylformamide or acetonitrile at room temperature. The acids of formula (LVI) are obtained by hydrolysis of the esters of formula (LV) in the presence of trifluoroacetic acid or hydrochloric acid in a polar solvent such as dichloromethane or dioxane at room temperature.

Scheme 13

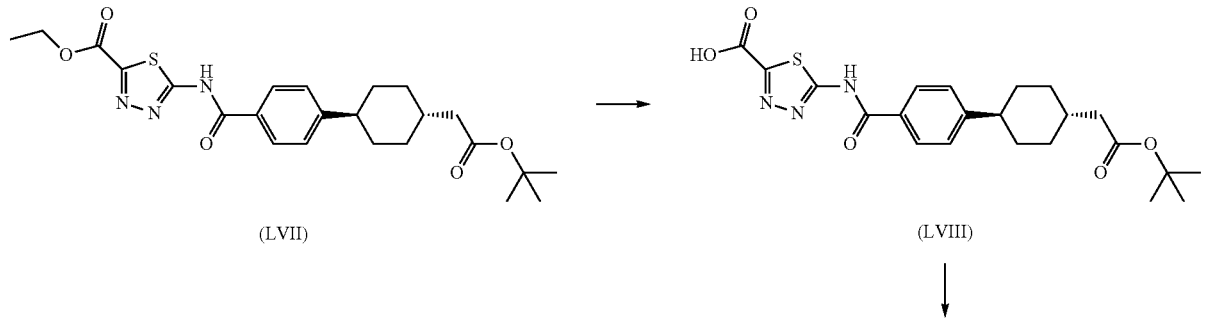

(LVII)    (LVIII)

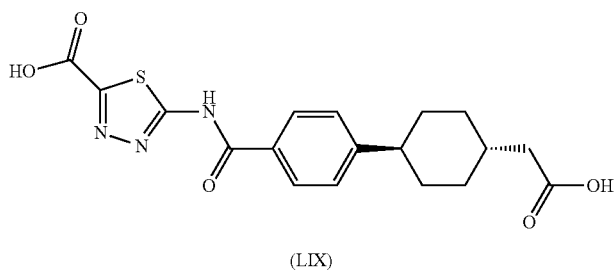

(LIX)

In Scheme 13, compound (LVIII) is obtained by chemoselective hydrolysis of the diester (LVII) with an alkaline base such as lithium hydroxide in a mixture of polar solvents such as water, methanol or tetrahydrofuran. Compound (LIX) is obtained by hydrolysis of the ester of formula (LVIII) in the presence of trifluoroacetic acid or hydrochloric acid in a polar solvent such as dichloromethane or dioxane at room temperature.

Scheme 14

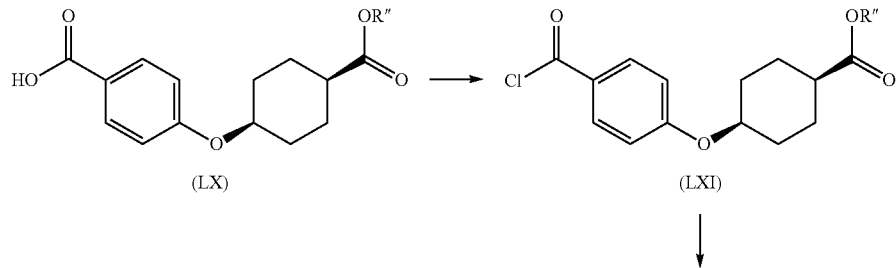

(LX)    (LXI)

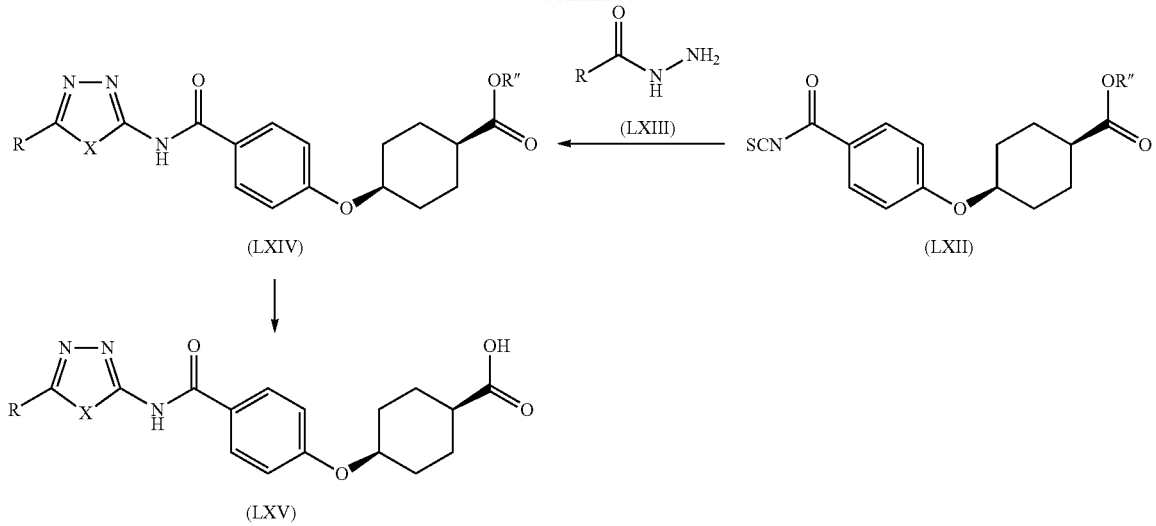

In Scheme 14, the acid chlorides of formula (LXI) are obtained from the carboxylic acids of formula (LX) via the action of a chlorinating agent such as oxalyl chloride in a polar solvent such as dichloromethane in the presence of a catalyst such as DMF. The acid chlorides of formula (LXI) thus obtained react with potassium thioisocyanate in a polar solvent such as acetonitrile or acetone to give the acylthioisocyanate products of formula (LXII). The reaction of the hydrazides of formula (LXIII) with the thioisocyanates of formula (LXII) in a polar solvent such as acetonitrile at between 60 and 80° C. gives the intermediates of formula (LXIV). The acids of formula (LXV) are obtained by hydrolysis of the esters of formula (LXIV) in the presence of trifluoroacetic acid or hydrochloric acid in a polar solvent such as dichloromethane or dioxane at room temperature.

The hydrazides of formula (LXIII) are obtained from the esters or from the corresponding acids via methods chosen from those known to a person skilled in the art. They include, inter alia, the use of a reagent such as hydrazine on the esters in a polar solvent such as refluxing ethanol or of a reagent such as tert-butyl carbazate on the acids in the presence of a coupling agent (for example 1-ethyl-3-(3-dimethylaminopropyl)carbodiimide) in a polar solvent such as dichloromethane at room temperature, followed by a deprotection in the presence of trifluoroacetic acid or hydrochloric acid in a polar solvent such as dichloromethane or dioxane at room temperature.

Scheme 15

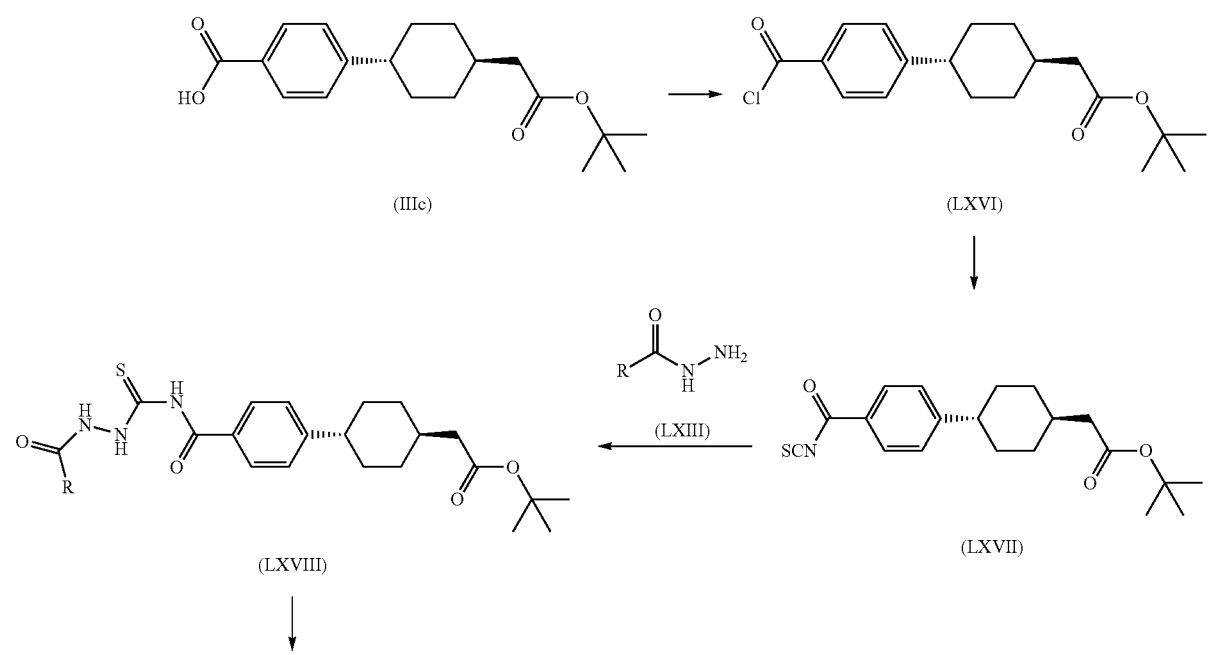

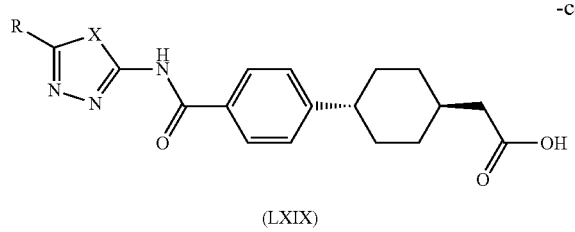

(LXIX)

In Scheme 15, the acid chlorides of formula (LXVI) are obtained from the carboxylic acids of formula (IIIc) via the action of a chlorinating agent such as oxalyl chloride in a polar solvent such as dichloromethane in the presence of a catalyst such as DMF. The acid chlorides of formula (LXVI) thus obtained react with potassium thioisocyanate in a polar solvent such as acetonitrile or acetone to give the acylthioisocyanates of formula (LXVII). The reaction of the hydrazides of formula (LXIII) with the thioisocyanates of formula (LXVII) in a polar solvent such as acetonitrile at between 60 and 80° C. gives the intermediates of formula (LXVIII). The intermediates of formula (LXVIII) cyclize into compounds of formula (LXIX) upon hydrolysis of the ester functions in the presence of trifluoroacetic acid or hydrochloric acid in a polar solvent such as dichloromethane or dioxane at room temperature.

In Scheme 16, the ketone (LXX) is reduced with a hydride such as sodium borohydride in a polar solvent such as methanol to give the alcohol (LXXI). The intermediate of formula (LXXI) is employed in a Mitsunobu reaction with an alcohol such as phenol in a polar solvent such as tetrahydrofuran at room temperature to give the ether of formula (LXXII). The acid of formula (LXXIII) is obtained by deprotection of the ester (LXXII) with an alkaline base such as lithium hydroxide in a mixture of polar solvents such as water, methanol or tetrahydrofuran.

Scheme 16

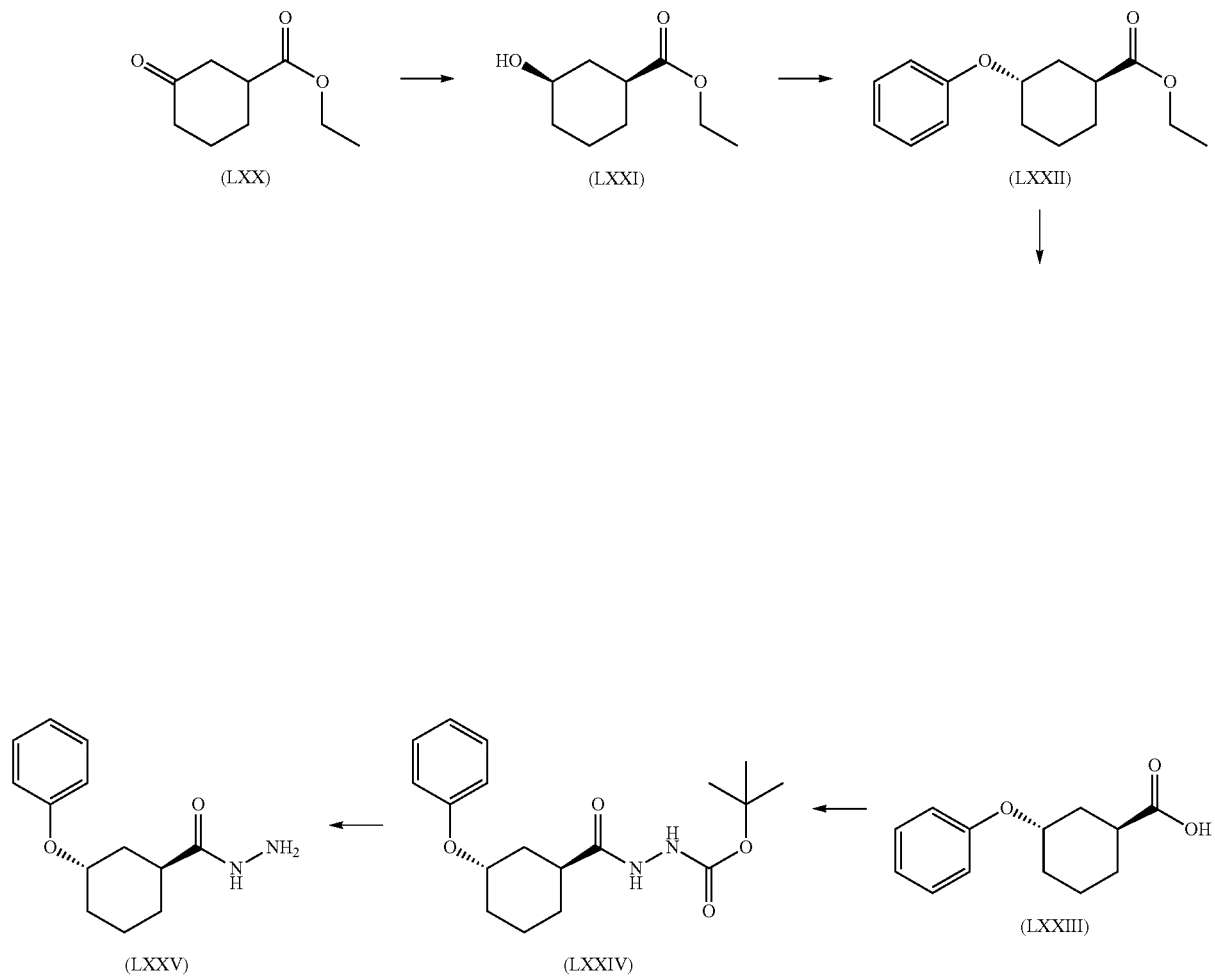

The intermediate of formula (LXXIV) is obtained by coupling the acid of formula (LXXIII) with tert-butyl carbazate in the presence of a coupling agent (for example 1-ethyl-3-(3-dimethylaminopropyl)carbodiimide) in a polar solvent such as dichloromethane at room temperature. Compound (LXXV) is obtained by hydrolysis of the intermediates of formula (LXXIV) in the presence of trifluoroacetic acid or hydrochloric acid in a polar solvent such as dichloromethane or dioxane at room temperature.

in a solvent such as refluxing toluene. The compounds of formula (LXXVIII) are prepared via a Horner-Wadsworth-Emmons reaction from the derivatives of formula (LXXVII) and the phosphonate of formula (XIV) in a polar solvent such as dimethylformamide or tetrahydrofuran at room temperature in the presence of a base such as sodium hydride. The compounds of formula (LXXVIII) are hydrogenated in the presence of a transition metal such as palladium in a polar solvent such as ethanol to give compound (LXXIX). The

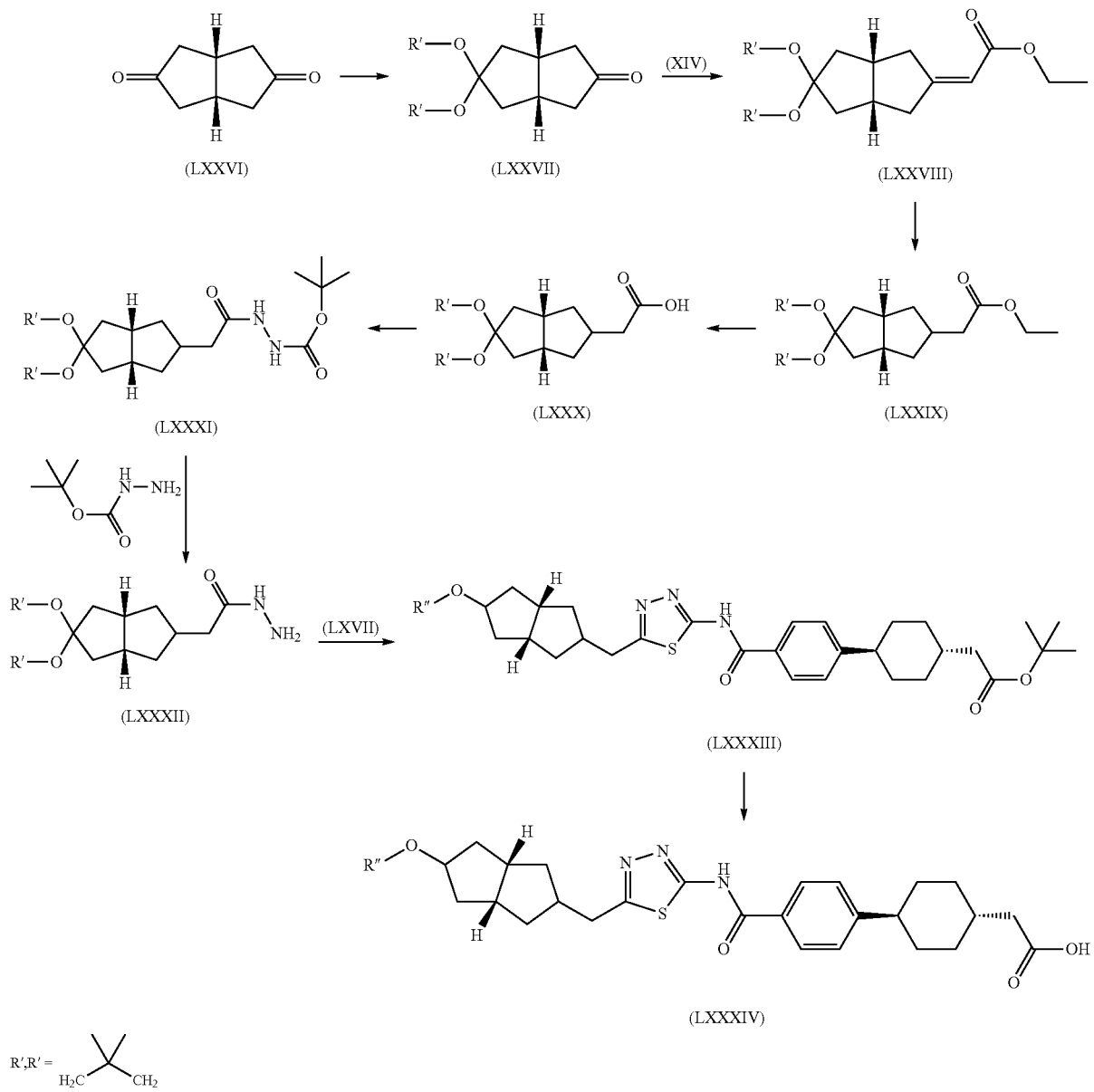

Scheme 17

In Scheme 17, the monoprotection of a ketone function of the compound of formula (LXXVI) with an alcohol of general formula R'OH or of a diol of general formula HOR'—R'OH gives the intermediates of formula (LXXVII) via methods chosen from those known to a person skilled in the art. They include, inter alia, the use of para-toluenesulfonic acid acids of formula (LXXX) are obtained by deprotecting the esters of formula (LXXIX) with an alkaline base such as lithium hydroxide in a mixture of polar solvents such as water, methanol or tetrahydrofuran. The intermediates of formula (LXXXI) are obtained by coupling the acids of formula (LXXX) with tert-butyl carbazate in the presence of a coupling agent (for example 1-ethyl-3-(3-dimethylaminopropyl) carbodiimide) in a polar solvent such as dichloromethane at room temperature. The compounds of formula (LXXXII) are obtained by hydrolysis of the intermediates of formula (LXXXI) in the presence of trifluoroacetic acid or hydrochloric acid in a polar solvent such as dichloromethane or dioxane at room temperature. Reaction of the hydrazides of formula (LXXXII) with the thioisocyanates of formula LXVII) in a polar solvent such as acetonitrile or acetone at between 60 and 80° C. gives the intermediates of formula (LXXXIII). The acids of formula (LXXXIV) are obtained by hydrolysis of the esters of formula (LXXXIII) in the presence of trifluoroacetic acid or hydrochloric acid in a polar solvent such as dichloromethane or dioxane at room temperature.

In Scheme 18, the compound of formula (IX) is converted into the enol triflate (LXXXV) via methods chosen from those known to a person skilled in the art. They include, inter alia, the use of a reagent such as N,N-bistrifluoromethanesulfonimide in the presence of a base such as n-butyllithium in a polar solvent such as tetrahydrofuran at temperatures of between −70° C. and 25° C.

The enol triflate (LXXXV) is converted into the intermediate (LXXXVI) in an alkoxycarbonylation reaction via methods chosen from those known to a person skilled in the art. They include, inter alia, the use of a carbonylation reagent such as molybdenum hexacarbonyl and a palladium catalyst such as palladium diacetate in a polar solvent such as tert-butanol at between 100 and 120° C. Compound (LXXXVI) is hydrogenated in the presence of a transition metal such as palladium in a polar solvent such as ethanol at a temperature of between 25 and 40° C. to give the compound of formula (LXXXVII). The acid of formula (LXXXVIII) is obtained by deprotection of the ester (LXXXVII) with an alkaline base such as lithium hydroxide in a mixture of polar solvents such as water, methanol or tetrahydrofuran. The intermediates of formula (LXXXIX) are obtained by coupling the acid of formula (LXXXVIII) with the aminothiadiazoles or aminooxadiazoles of formula (II) in the presence of a coupling agent (for example bromotris-pyrrolidinophosphonium hexafluorophosphonate) in a polar solvent such as dimethylformamide or acetonitrile at room temperature. The acids of formula (XC) are obtained by hydrolysis of the esters of

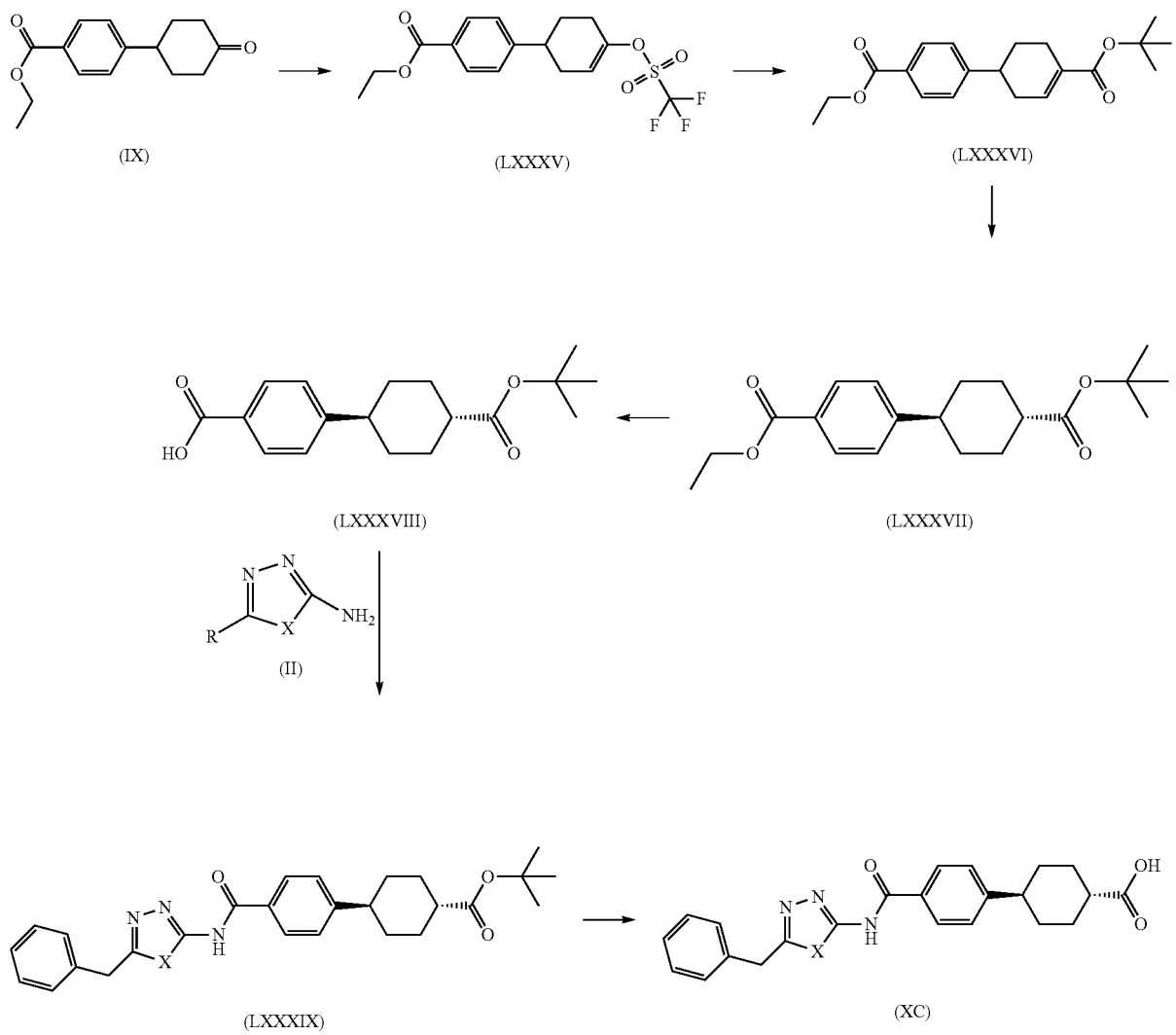

formula (LXXXIX) in the presence of trifluoroacetic acid or hydrochloric acid in a polar solvent such as dichloromethane or dioxane at room temperature.

In Scheme 19, the compound of formula (XCI) is converted into the alcohol (XCII) using a reducing agent such as sodium borohydride in a polar solvent such as DMF. The intermediate (XCII) is treated with an acid such as trifluoroacetic acid in a polar solvent such as dichloromethane to give the acid (XCIII).

Scheme 19

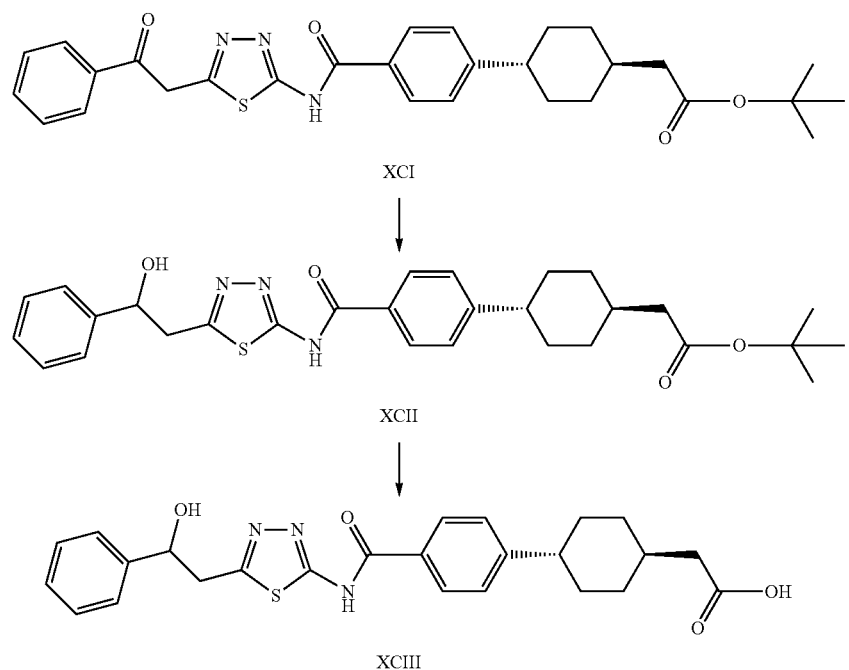

In Scheme 20, the thioether of formula (XCIV) is oxidized to the sulfoxide (XCV) using a peracid such as meta-chloroperbenzoic acid in a polar solvent such as dichloromethane.

Scheme 20

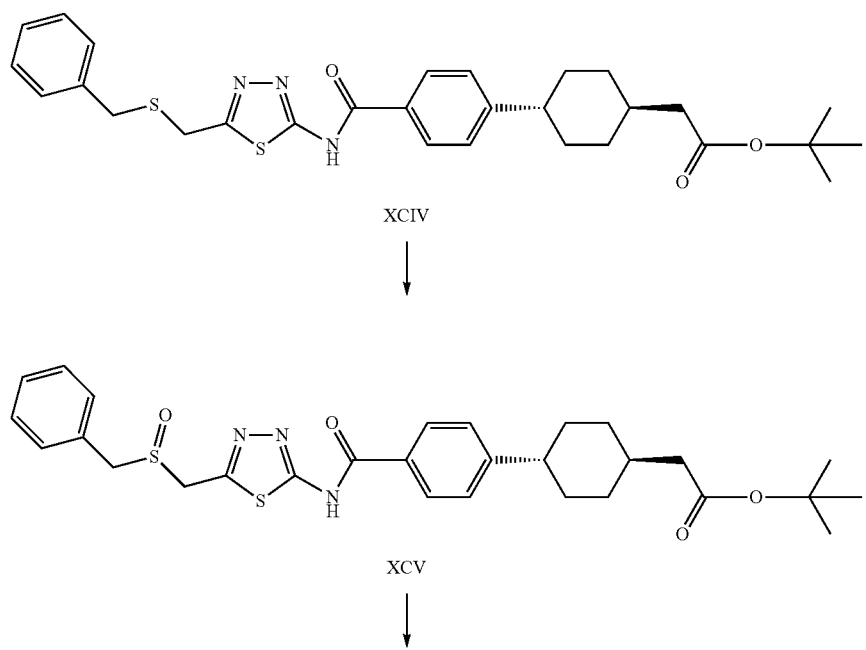

-continued

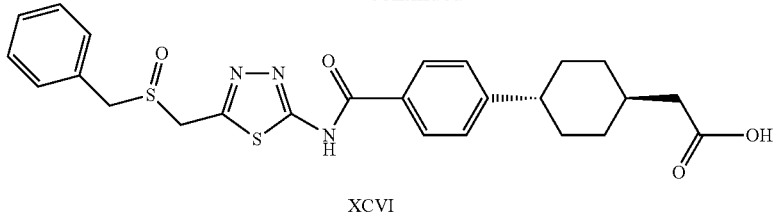

XCVI

The intermediate (XCV) is treated with an acid such as trifluoroacetic acid in a polar solvent such as dichloromethane to give the acid (XCVI).

In Scheme 21, the acids (LXIX) are converted into the amides (XCVII) with ammonia or an amine HNR5 in the presence of a coupling agent (for example bromotris-pyrrolidinophosphonium hexafluorophosphonate) in a polar solvent such as DMF at room temperature. HNR5 is an alkylamine substituted with a hydroxyl, dialkylamine, heterocycloalkyl or alkyloxy group.

Scheme 21

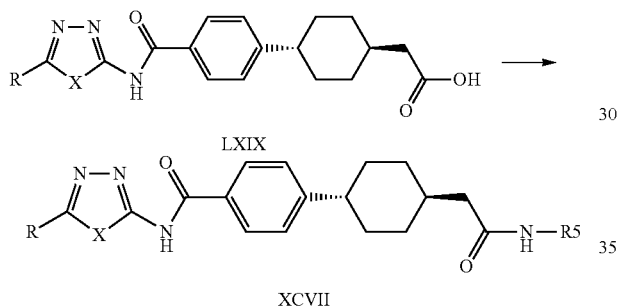

According to another of its aspects, a subject of the invention is also the compounds of formulae (III), (IIIa), (IIIb), (IIIc), (V), (XXI) with the exclusion of the compound 4-(4-ethoxycarbonylcyclohexyloxy)benzoic acid, (XXIII), (XXVIII), (XXIX), (XXX), (XXXV), (XXXVI), (XXXVIII), (XL), (XLIIa), (XLIIb), (XLVI), (XLVII), (LIV), (LV), (LVIII), (LXIV), (LXVIII), (LXXV), (LXXXII), (LXXXIII), (LXXXIX), (XCI), (XCII), (XCIV) and (XCV). These compounds are useful as intermediates for the synthesis of the compounds of formula (I).

The examples that follow describe the preparation of certain compounds in accordance with the invention. These examples are not limiting, and serve merely to illustrate the present invention. The numbers of the compounds given as examples refer to those given in the table hereinbelow, which illustrates the chemical structures and physical properties of a few compounds according to the invention.

The following abbreviations and empirical formulae are used:

| | |
|---|---|
| ACN | acetonitrile |
| BSA | bovine serum albumin |
| ° C. | degrees Celsius |
| LC-MS | liquid chromatography-mass spectrometry |
| $CO_2$ | carbon dioxide |
| $cm^2$ | square centimetres |
| DIEA | diisopropylethylamine |
| dec. | decomposition |
| DMAP | 4-dimethylaminopyridine |
| DMEM | Dulbecco's Minimum Essential Medium Modified |
| DMF | dimethylformamide |
| DPPF | 1,1'-bis(diphenylphosphino)ferrocene |
| EDTA | ethylenediaminetetraacetic acid |
| eq. | equivalent |
| ESI+ | electrospray Ionization |
| g | gram |
| NMR | nuclear magnetic resonance |
| h | hour(s) |
| $H_2O$ | water |
| HPLC | high-performance liquid chromatography |
| Hz | Hertz |
| M | mass |
| MHz | megahertz |
| mg | milligram |
| mL | millilitre |
| mm | millimetre |
| mmol | millimoles |
| M.W. | microwaves |
| N | normal |
| N-Boc- | N-tert-Butyloxycarbonyl |
| nM | nanomolar |
| PBS | phosphate-buffered saline |
| ppm | parts per million |
| psi | pounds per square inch |
| SVF | foetal calf serum |
| $SO_2$ | sulfur dioxide |
| TFA | trifluoroacetic acid |
| THF | tetrahydrofuran |
| UPLC | ultra-high performance liquid chromatography |
| UV | ultraviolet |
| HIV | human immunodeficiency virus |
| µCi | microcuries |
| % | percentage |

The radioactivity measurement is performed using a Flo One C625TR machine (Perkin-Elmer).

The proton magnetic resonance spectra ($^1$H NMR), as described hereinbelow, are recorded at 400 MHz in DMSO-$d_6$, using the peak of DMSO-$d_5$ as the reference. The chemical shifts δ are expressed in parts per million (ppm). The observed signals are expressed as follows: s=singlet; d=doublet; t=triplet; m=multiplet or broad singlet.

The LC/MS column and the examples indicate the peak MH$^+$ identified by mass spectrometry. The compounds are analysed by liquid chromatography (UV detector at 220 nm) coupled to a mass spectrometer with an electrospray ionization detector. The analytical method is detailed below:

UPLC/MS—gradient of 3 min—water/ACN/TFA

T 0 min: 98% A—T 1.6 to T 2.1 min: 100% B—T 2.5 to T 3 min: 98% A

Route A: water+0.05% TFA, route B: ACN+0.035% TFA

Flow rate: 1.0 mL/min—T°=40° C.—injection 2 µL

Acquity BEH C18 column (50*2.1 mm; 1.7*µm)

EXAMPLE 1

5-(4-fluorobenzyl)-1,3,4-thiadiazol-2-amine

1.1 Synthesis of 2-[(4-fluorophenyl)acetyl]hydrazinecarbothioamide 5 g of 4-fluorophenylacetic acid (32.44 mmol, 1 eq.) are placed in 50 mL of dichloromethane with stirring. 3.25 g of thiosemicarbazide (35.68 mmol, 1 eq.), 4.38 g of hydroxybenzotriazole (32.44 mmol, 1 eq.) and 6.22 g of 1-ethyl-3-(3-dimethylaminopropyl)carbodiimide hydrochloride (32.44 mmol, 1.2 eq.) are successively added with continued stirring at room temperature. After 18 hours at room temperature, the dichloromethane is evaporated off. The residue is taken up in ethyl acetate, washed three times with water, once with brine and three times with 1N hydrochloric acid. The organic phase is dried over sodium sulfate and evaporated to give 5 g of 2-[(4-fluorophenyl)acetyl]hydrazinecarbothioamide.
M-isobutene$^+$=228.

1.2 Synthesis of 5-(4-fluorobenzyl)-1,3,4-thiadiazol-2-amine 5 mL of sulfuric acid are placed in a round-bottomed flask, which is cooled to between 0 and −10° C. by placing it in a bath of ice and sodium chloride.
0.38 g of 2-[(4-fluorophenyl)acetyl]hydrazinecarbothioamide (1.67 mmol) is added portionwise with stirring. After stirring for 3 hours between 0 and −10° C., water is added dropwise and the mixture is then returned to basic pH with sodium hydroxide, while maintaining a temperature of between 0 and −10° C. The precipitate is filtered off, washed with water and dried. 0.264 g of 5-(4-fluorobenzyl)-1,3,4-thiadiazol-2-amine is obtained.
M+H$^+$=210.

EXAMPLE 2

4-(4-tert-butoxycarbonylmethylcyclohexyl)benzoic acid

2.1 Synthesis of ethyl 4-(4-tert-butoxycarbonylmethylenecyclohexyl)benzoate 5.63 g of tert-butyl diethylphosphoacetate (20.3 mmol, 1 eq.) are placed in 20 mL of dimethylformamide with stirring. The solution is cooled to a temperature of 4° C. by placing it in an ice bath, and 0.536 g of sodium hydride (22.33 mmol, 1.1 eq.) is then added portionwise. After 30 minutes, 5 g of ethyl 4-(4-oxo-cyclohexyl)benzoate (20.3 mmol, 1 eq.) are added and the ice bath is removed. After stirring for 1 hour, the flask is placed in an ice bath to cool the reaction medium to a temperature of 4° C., and 0.049 g of sodium hydride (2.04 mmol, 0.1 eq.) is added. The ice bath is removed and, after 30 minutes, the mixture is poured into 200 mL of 1N potassium hydrogen sulfate and extracted with 300 mL of ethyl ether. The organic phase is washed 4 times with brine. The organic phase is dried over sodium sulfate and evaporated. The residue is chromatographed on silica gel, eluting with a gradient of methanol in dichloromethane ranging from 0% to 5%. 5.04 g of ethyl 4-(4-tert-butoxycarbonylmethylenecyclohexyl)benzoate are obtained.
M+H$^+$=345.

2.2 Synthesis of ethyl 4-(4-tert-butoxycarbonylmethylcyclohexyl)benzoate 5.04 g of ethyl 4-(4-tert-butoxycarbonylmethylenecyclohexyl)benzoate (14.63 mmol, 1 eq.) and 15 mL of ethanol are placed in a Parr bottle. 0.31 g of 10% palladium-on-charcoal (0.29 mmol, 0.02 eq.) is added and the reaction medium is placed under 50 psi of hydrogen for 3 hours at a temperature of 25° C. The reaction medium is filtered and concentrated to give 4.31 g of ethyl 4-(4-tert-butoxycarbonylmethylcyclohexyl)benzoate.
M-isobutene$^+$=291.

2.3 Synthesis of 4-(4-tert-butoxycarbonylmethylcyclohexyl)benzoic acid 3.3 g of ethyl 4-(4-tert-butoxycarbonylmethylcyclohexyl) benzoate (9.52 mmol, 1 eq.) are dissolved in 30 mL of a 2/1 mixture of tetrahydrofuran/methanol, followed by addition of 1.60 g of lithium hydroxide hydrate (38.10 mmol, 4 eq. dissolved in 10 mL of water). The reaction medium is stirred for 4 hours at room temperature. The solvents are evaporated off and an aqueous solution of $SO_2$ is added. The solid obtained is filtered off, washed with water and dried to give 2 g of 4-(4-tert-butoxycarbonyl-methylcyclohexyl)benzoic acid.

2.4. Synthesis of trans-4'(4-tert-butoxycarbonylmethylcyclohexyl)benzoic acid 0.5 g of 4-(4-tert-butoxycarbonylmethylcyclohexyl)benzoic acid is recrystallized from ethyl acetate at the reflux point of the solution. After filtration and drying, 0.17 g of trans-4-(4-tert-butoxycarbonylmethylcyclohexyl)benzoic acid is obtained.
$^1$H NMR (400 MHz, DMSO-d6) δ ppm 12.77 (m, 1H), 7.87 (m, J=9 Hz, 2H), 7.36 (m. J=9 Hz, 2H), 2.54 (m, 1H), 2.13 (d, J=7.3 Hz, 2H), 1.87 to 1.68 (m, 5H), 1.49 (m, 2H), 1.43 (s, 9H), 1.14 (m, 2H).

EXAMPLE 3

4-(4-ethylcarbonylmethylcyclohexyl)benzoic acid

3.1 Synthesis of ethyl [4-(4-hydroxyphenyl)cyclohexylidene]acetate 10 g of 4-(4-hydroxyphenyl)cyclohexanone (52.56 mmol, 1 eq.) are placed in 150 mL of tetrahydrofuran in a 250 mL round-bottomed flask under nitrogen. The solution is cooled to 4° C. on an ice bath and 2.523 g of 60% sodium hydride (63.08 mmol, 1.2 eq.) are added portionwise. 14.141 g of ethyl diethylphosphoacetate (63.08 mmol, 1.2 eq.) are placed in 150 mL of tetrahydrofuran in another 250 mL round-bottomed flask under nitrogen. This second solution is cooled on an ice bath and 2.523 g of 60% sodium hydride (63.08 mmol, 1.2 eq.) are added portionwise. The ice baths are removed and the media are stirred at room temperature for 30 minutes. The 4-(4-hydroxyphenyl)-cyclohexanone solution is added to the ethyl diethylphosphoacetate solution. The reaction medium is stirred for 1 hour 30 minutes. Saturated aqueous ammonium chloride solution is added and the reaction medium is extracted three times with ethyl acetate. The organic phase is dried over magnesium sulfate, filtered and evaporated to give 13.5 g of ethyl [4-(4-hydroxyphenyl)cyclohexylidene]acetate. M+H$^+$=261.

3.2 Synthesis of ethyl [4-(4-hydroxyphenyl)cyclohexyl]acetate 6.646 g of ethyl [4-(4-hydroxyphenyl)cyclohexylidene]acetate (26.53 mmol, 1 eq.) are placed in 150 mL of ethyl acetate in a Parr bottle under nitrogen. 0.77 g of 10% palladium-on-charcoal (0.72 mmol, 0.03 eq.) is added and the reaction medium is placed under 50 psi of hydrogen for 3 hours at 25° C. The reaction medium is filtered and concentrated to give 6.27 g of ethyl [4-(4-hydroxyphenyl)cyclohexyl]acetate.

M+CH$_3$CN$^+$=304.

3.3 Synthesis of ethyl [4-(4-trifluoromethanesulfonyloxyphenyl)cyclohexyl]acetate 6.27 g of ethyl [4-(4-hydroxyphenyl)cyclohexyl]acetate (23.90 mmol, 1 eq.) are placed in 100 mL of dichloromethane. The solution is cooled on an ice bath, and 6.3 mL of diisopropylethylamine (35.85 mmol, 1.5 eq.) and 4.4 mL of triflic anhydride (26.29 mmol, 1.1 eq.) are successively added. The ice bath is removed and the reaction medium is stirred for 16 hours. The medium is poured into ice-water and extracted with 250 mL of dichloromethane. The organic phase is dried over magnesium sulfate, filtered and evaporated. The residue is chromatographed on silica gel, eluting with a gradient of ethyl acetate in heptane ranging from 5% to 10%. 5.76 g of ethyl [4-(4-trifluoromethanesulfonyloxyphenyl)cyclohexyl]acetate are obtained.

M+CH$_3$CN$^+$=436.

3.4 Synthesis of 4-(4-ethoxycarbonylmethylcyclohexyl)benzoic acid

One third of the 3 g of ethyl [4-(4-trifluoromethanesulfonyloxyphenyl)cyclohexyl]acetate (3 g, 7.61 mmol, 1 eq.) is placed, respectively, in one third of the 18 mL of dioxane in three 20 mL microwave tubes. One third of each amount of the reagents molybdenum hexacarbonyl (1 g, 3.80 mmol, 0.5 eq.), 0.171 g of palladium acetate (II) (0.76 mmol, 0.1 eq.), 0.422 g of 1,1'-bis(diphenylphosphino)ferrocene (0.76 mmol, 0.1 eq.), 1.859 g of 4-dimethylaminopyridine (15.21 mmol, 2 eq.), 3.1 mL of diisopropylethylamine (17.49 mmol, 2.3 eq.) and 2.74 mL of water is successively and respectively added to each tube. The tubes are heated at 120° C. for 20 minutes in a Biotage microwave machine. The reaction media are filtered through Celite. The filtrate is diluted with 200 mL of dichloromethane and washed with twice 100 mL of saturated sodium carbonate solution. 10 mL of ethyl ether are added. After separation of the phases by settling, the aqueous phase is acidified to pH=1 with 5N hydrochloric acid solution and extracted with twice 200 mL of dichloromethane. The organic phase is concentrated to dryness to give 0.560 g of 4-(4-ethoxycarbonylmethylcyclohexyl)benzoic acid.

M+CH$_3$CN$^+$=332.

EXAMPLE 4

(4-{4-[5-(4-fluorobenzyl)[1.3.4]oxadiazol-2-ylcarbamoyl]phenyl}cyclohexyl)acetic acid (compound 33 of Table I)

4.1 Synthesis of ethyl (4-{4-[5-(4-fluorobenzyl)[1.3.4]oxadiazol-2-ylcarbamoyl]-phenyl}-cyclohexyl)acetate 0.183 g of 5-(4-fluorobenzyl)[1.3.4]oxadiazol-2-ylamine (0.95 mmol, 1.1 eq.) is placed in 5 mL of acetonitrile at room temperature with stirring. 0.25 g of 4-(4-ethoxycarbonylmethylcyclohexyl)benzoic acid (0.86 mmol, 1 eq.), 0.128 g of hydroxybenzotriazole (0.95 mmol, 1.1 eq.) and 0.182 g of 1-ethyl-3-(3-dimethylaminopropyl)carbodiimide hydrochloride (0.95 mmol, 1.1 eq.) are successively added with stirring.

After 18 hours, the dichloromethane is evaporated off. The residue is chromatographed on silica gel, eluting with a gradient of ethyl acetate in heptane. 0.37 g of activated ester is obtained, which product is placed in a 20 mL microwave tube with 5-(4-fluorobenzyl)[1.3.4]oxadiazol-2-ylamine (0.183 g, 0.95 mmol, 1.1 eq.) and 5 mL of dimethylformamide. The tube is heated at 100° C. for 30 minutes and at 120° C. for 30 minutes in a Biotage microwave machine. The reaction medium is diluted with ethyl acetate, washed three times with water and finally with brine. The organic phase is dried over magnesium sulfate, filtered and evaporated. The residue is chromatographed on silica gel, eluting with a gradient of ethyl acetate in heptane ranging from 20% to 33%. 0.1 g of ethyl (4-{4-[5-(4-fluorobenzyl)[1.3.4]oxadiazol-2-ylcarbamoyl]phenyl}cyclohexyl)acetate is obtained.

M+H$^+$=466.

4.2 Synthesis of (4-{4-[5-(4-fluorobenzyl)[1,3,4]oxadiazol-2-ylcarbamoyl]phenyl}cyclohexyl)acetic acid 0.1 g of ethyl (4-{4-[5-(4-fluorobenzyl)[1,3,4]oxadiazol-2-ylcarbamoyl]phenyl}cyclohexyl)acetate (0.21 mmol, 1 eq.) and 0.036 g of lithium hydroxide hydrate (0.86 mmol, 4 eq.) are dissolved in 4 mL of a 2/1/1 mixture of tetrahydrofuran/methanol/water cooled to 4° C. using an ice bath. The reaction medium is stirred for 4 hours at room temperature. The solvents are evaporated off and an aqueous solution of SO$_2$ is added. The solid obtained is filtered off, washed with water and dried to give 0.05 g of (4-{4-[5-(4-fluorobenzyl)[1.3.4]oxadiazol-2-ylcarbamoyl]phenyl}cyclohexyl)acetic acid.

M+H$^+$=438.

$^1$H NMR (400 MHz, DMSO-d6) δ ppm 11.9 (m, 2H), 7.92 (d, J=8.4 Hz, 1H), 7.41 (m, 4H), 7.21 (m, J=8.8 Hz, 2H), 4.28 (s, 2H), 2.63-2.12 (m, 3H), 1.90-1.43 (m, 7H), 1.14 (m, 2H).

EXAMPLE 5

(4-{4-[5-(4-fluorobenzyl)[1.3.4]thiadiazol-2-ylcarbamoyl]phenyl}cyclohexyl)acetic acid (Compound 5 of Table I)

5.1 Synthesis of tert-butyl (4-{4-[5-(4-fluorobenzyl)[1.3.4]thiadiazol-2-ylcarbamoyl]-phenyl}cyclohexyl)acetate 0.3 g of 4-(4-tert-butoxycarbonylmethylcyclohexyl)benzoic acid (0.94 mmol, 1 eq.) is placed in a mixture of 5 mL of dichloromethane and 2 mL of dimethylformamide at room temperature. 0.394 g of 5-(4-fluorobenzyl)-1,3,4-thiadiazol-2-amine (1.88 mmol, 2 eq.), 1.054 g of bromotris-pyrrolidinophosphonium hexafluorophosphonate (2.26 mmol, 2.4 eq.) and 0.66 mL of diisopropylethylamine (3.76 mmol, 4 eq.) are successively added. The reaction mixture is stirred for 6 days at room temperature, diluted in ethyl acetate, washed with saturated aqueous ammonium chloride solution, and washed twice with water and once with brine. The organic phase is concentrated and the residue is chromatographed on silica gel, eluting with a gradient of ethyl acetate in heptane ranging from 10% to 33%. 0.35 g of tert-butyl (4-{4-[5-(4-fluorobenzyl)[1.3.4]thiadiazol-2-ylcarbamoyl]phenyl}cyclohexyl)acetate is obtained.

M+H$^+$=510

5.2 Synthesis of (4-{4-[5-(4-fluorobenzyl)[1.3.4] thiadiazol-2-ylcarbamoyl]phenyl}cyclohexyl)acetic acid 0.35 g of tert-butyl (4-{4-[5-(4-fluorobenzyl)[1.3.4]thiadiazol-2-ylcarbamoyl]phenyl}cyclohexyl)acetate (0.69 mmol, 1 eq.) is placed in 5 mL of dichloromethane. 1 mL of trifluoroacetic acid (13.46 mmol, 19.6 eq.) is added and the reaction medium is stirred for 18 hours at room temperature. The solvent is evaporated off and the residue is taken up in ethyl acetate, ethanol and methanol to give 117 mg of (4-{4-[5-(4-fluorobenzyl)[1.3.4]thiadiazol-2-ylcarbamoyl]phenyl}cyclohexyl)acetic acid.

M+H$^+$=454

$^1$H NMR (400 MHz, DMSO-d6) δ ppm 13.02 to 11.66 (m, 2H), 8.01 (m, 2H), 7.46 to 7.36 (m, 4H), 7.18 (m, 2H), 4.37 (s, 2H), 2.69 to 2.51 (m, 1H), 2.41 to 2.10 (m, 2H), 1.89 to 1 (m, 9H).

EXAMPLE 6 trans-4-[4-(5-benzyl[1.3.4]thiadiazol-2-ylcarbamoyl) phenoxy]cyclohexanecarboxylic acid (Compound 53 of Table II)

6.1 Synthesis of methyl cis-4-hydroxycyclohexanecarboxylate 2 g of cis-4-hydroxycyclohexanecarboxylic acid (13.87 mmol, 1 eq.) are placed in 50 mL of a 4/1 mixture of toluene/methanol at room temperature. Trimethylsilyl-diazomethane (111 mL, 221.96 mmol, 16 eq.) is poured into the reaction medium with stirring. After 3 hours at room temperature, the reaction medium is evaporated to give 2.6 g of methyl cis-4-hydroxycyclohexanecarboxylate.

6.2 Synthesis of tert-butyl trans-4-(4-methoxycarbonylcyclohexyloxy)benzoate 2.20 g of methyl cis-4-hydroxycyclohexanecarboxylate (13.88 mmol, 1 eq.), 2.70 g of tert-butyl 4-hydroxybenzoate (13.88 mmol, 1 eq.) and 5.46 g of triphenylphosphine (20.82 mmol, 1.5 eq.) are placed in 30 mL of tetrahydrofuran at room temperature. 4.04 mL of diisopropyl azodicarboxylate (20.82 mmol, 1.5 eq.) are added dropwise to the reaction medium with stirring. After 3 hours at room temperature, the medium is concentrated to dryness and taken up in diethyl ether. The triphenylphosphine oxide is filtered off. The organic phase is washed successively with sodium hydroxide solution and then with water, dried over sodium sulfate, filtered and evaporated to give a residue. This residue is chromatographed on silica gel, eluting with a gradient of ethyl acetate in heptane ranging from 10% to 50%. 1.6 g of tert-butyl trans-4-(4-methoxycarbonylcyclohexyloxy)benzoate are obtained.

6.3 Synthesis of trans-4-(4-methoxycarbonylcyclohexyloxy)benzoic acid 1.6 g of tert-butyl trans-4-(4-methoxycarbonylcyclohexyloxy)benzoate (4.78 mmol, 1 eq.) are placed in dichloromethane. The reaction medium is cooled to a temperature of 4° C. with stirring in an ice bath. 3 mL of trifluoroacetic acid (40.39 mmol, 8.44 eq.) are added and the ice bath is removed. After stirring for 17 hours at room temperature, the medium is concentrated, taken up in diethyl ether and filtered to give 1.0 g of trans-4-(4-methoxycarbonylcyclohexyloxy) benzoic acid.

m.p.=162° C.

6.4 Synthesis of methyl trans-4-[4-(5-benzyl[1.3.4] thiadiazol-2-ylcarbamoyl)phenoxy]-cyclohexanecarboxylate 0.301 g of trans-4-(4-methoxycarbonylcyclohexyloxy) benzoic acid (1.08 mmol, 1 eq.) is placed in 5 mL of dichloromethane at room temperature. 0.36 mL of diisopropylethylamine (2.16 mmol, 2 eq.), 0.604 g of bromotris-pyrrolidinophosphonium hexafluorophosphonate (1.30 mmol, 1.2 eq.) and 0.207 g of 5-benzyl-1,3,4-thiadiazol-2-amine (1.08 mmol, 1 eq.) are successively added. 2 mL of DMF are then added. The reaction mixture is stirred for 18 hours at room temperature. 0.1 mL of diisopropylethylamine (0.6 mmol, 0.55 eq.), 0.2 g of bromotris-pyrrolidinophosphonium hexafluorophosphonate (0.43 mmol, 0.4 eq.) and 0.05 g of 5-benzyl-1,3,4-thiadiazol-2-amine (0.26 mmol, 0.24 eq.) are added. The reaction medium is stirred at 50° C. for 6 hours, diluted in dichloromethane, and washed with water and with saturated aqueous sodium bicarbonate solution. The organic phase is dried over magnesium sulfate and concentrated, and the residue is chromatographed on silica gel, eluting with a gradient of ethyl acetate in heptane ranging from 10% to 70%. The fractions of interest are evaporated. The solid obtained is triturated in ethanol to give 0.128 g of methyl trans-4-[4-(5-benzyl[1.3.4]thiadiazol-2-ylcarbamoyl)phenoxy]cyclohexanecarboxylate.

M+H$^+$=452.

6.5 Synthesis of trans-4-[4-(5-benzyl[1.3.4]thiadiazol-2-ylcarbamoyl)phenoxy]cyclohexanecarboxylic acid 0.128 g of methyl 4-[4-(5-benzyl[1.3.4]thiadiazol-2-ylcarbamoyl)phenoxy]cyclohexanecarboxylate (0.28 mmol, 1 eq.) is placed in 2 mL of a mixture of tetrahydrofuran and water at room temperature. 0.024 g of lithium hydroxide monohydrate (0.57 mmol, 2 eq.) in 1 mL of water is added. After stirring for 2 hours at room temperature, the tetrahydrofuran is evaporated off and water is added. The aqueous phase is washed with dichloromethane. The aqueous phase is cooled to a temperature of 4° C. in an ice bath and acidified with 1N hydrochloric acid solution. The solid is filtered off and washed successively with water, with ethanol and then with diethyl ether to give 0.069 g of 4-[4-(5-benzyl[1.3.4] thiadiazol-2-ylcarbamoyl)phenoxy]cyclohexanecarboxylic acid.

M+H$^+$=438.

$^1$H NMR (400 MHz, DMSO-d6) δ ppm: 13.92-11.69 (m, 2H), 8.06 (m, J=9 Hz, 2H), 7.37 (m, 4H), 7.30 (m, 1H), 7.08 (m, J=9 Hz, 2H), 4.48 (m, 1H), 4.38 (s, 2H), 2.28 (m, 1H), 2.09 (m, 2H), 1.96 (m, 2H), 1.56 (m, 2H), 1.43 (m, 2H).

EXAMPLE 7 cis-{4-[4-(5-benzyl[1.3.4]thiadiazol-2-ylcarbamoyl) phenyl]cyclohexyl}-acetic acid (Compound 34 of Table I)

7.1 Synthesis of tert-butyl {4-[4-(5-benzyl[1.3.4] thiadiazol-2-ylcarbamoyl)phenyl]cyclohexyl}acetate 0.45 g of 4-(4-tert-butoxycarbonylmethylcyclohexyl)benzoic acid (1.41 mmol, 1 eq.) is placed in a mixture of 5 mL of dimethylformamide at room temperature. 0.539 g of 5-benzyl-1,3,4-thiadiazol-2-amine (2.82 mmol, 2 eq.), 0.791 g of bromotris-pyrrolidinophosphonium hexafluorophosphonate (1.70 mmol, 1.2 eq.) and 0.49 mL of diisopropylethylamine (2.83 mmol, 2 eq.) are successively added. The reaction mixture is stirred for 16 hours at room temperature, diluted in ethyl acetate and washed three times with water. The organic phase is concentrated. The residue is taken up and washed with ethanol, filtered and dried. 0.236 g of tert-butyl {4-[4-(5-benzyl[1.3.4]thiadiazol-2-ylcarbamoyl)phenyl]cyclohexyl}acetate is obtained.

M+H+=492.

7.2 Synthesis of cis-(4-{4-benzyl[1.3.4]thiadiazol-2-ylcarbamoyl}phenyl}cyclohexyl)acetic acid 0.35 g of tert-butyl {4-[4-(5-benzyl[1.3.4]thiadiazol-2-ylcarbamoyl)phenyl]cyclohexyl}-acetate (0.48 mmol, 1 eq.) is placed in 3 mL of dichloromethane. 1 mL of trifluoroacetic acid (13.46 mmol, 28 eq.) is added and the reaction medium is stirred for 18 hours at room temperature. The solvent is evaporated off and the residue is taken up in ethyl acetate to give, after filtration and drying, 194 mg of (4-{4-[5-(4-fluorobenzyl)[1.3.4]thiadiazol-2-ylcarbamoyl]phenyl}cyclohexyl)acetic acid.

cis-{4-[4-(5-benzyl[1.3.4]thiadiazol-2-ylcarbamoyl)phenyl]cyclohexyl}acetic acid is obtained by chromatographic separation using a Chiralcel OJ-H 250*21 mm (5 µm) stationary phase and a $CO_2$ (MeOH+0.5% of isopropylamine) mobile phase. A first isomer, 27 mg of trans-{4-[4-(5-benzyl[1.3.4]thiadiazol-2-ylcarbamoyl)phenyl]cyclohexyl}acetic acid, is obtained

M+H+=436.

A second isomer, 70 mg of cis-{4-[4-(5-benzyl[1.3.4]thiadiazol-2-ylcarbamoyl)phenyl]-cyclohexyl}acetic acid, is obtained.

M+H+=436.

$^1$H NMR (400 MHz, DMSO-d6) δ ppm 8.01 (m, 2H), 7.37 to 7.21 (m, 9H), 4.21 (s, 2H), 2.59 (m, 1H), 2.34 (m, 2H), 2.18 (m, 1H), 1.63 (m, 8H)

EXAMPLE 8 trans-{4-[4-(5-benzyl[1.3.4]thiadiazol-2-ylcarbamoyl)phenyl]cyclohexyl}acetic acid (Compound 1 of Table I)

8.1 Synthesis of tert-butyl trans-{4-[4-(5-benzyl[1.3.4]thiadiazol-2-ylcarbamoyl)phenyl]-cyclohexyl}acetate 3 g of trans-4-(4-tert-butoxycarbonylmethylcyclohexyl)benzoic acid (9.42 mmol, 1 eq.) are placed in 35 mL of a mixture of dichloromethane and dimethylformamide in a 250 mL round-bottomed flask under a nitrogen atmosphere, at room temperature. 1.528 g of hydroxybenzotriazole (11.1 mmol, 2 eq.), 2.168 g of 1-ethyl-3-(3-dimethylaminopropyl)carbodiimide hydrochloride (11.1 mmol, 2 eq.), 3.11 mL of diisopropylethylamine (18.84 mmol, 2 eq.) and 2.162 g of 5-benzyl-1,3,4-thiadiazol-2-amine (11.1 mmol, 2 eq.) are successively added with stirring. The reaction mixture is stirred for 4 days at room temperature. The reaction medium is evaporated to dryness and diluted in water. The precipitate obtained is filtered off and washed with water. The solid obtained is dissolved in a minimum amount of dichloromethane and chromatographed on silica gel, eluting with a gradient of ethyl acetate in dichloromethane ranging from 2.5% to 25%. 3.13 g of tert-butyl trans-{4-[4-(5-benzyl[1.3.4]thiadiazol-2-ylcarbamoyl)phenyl)cyclohexyl}acetate are obtained.

M+H+=492.

8.2 Synthesis of trans-(4-{4-benzyl[1.3.4]thiadiazol-2-ylcarbamoyl]phenyl}cyclohexyl)acetic acid 2.11 g of tert-butyl {4-[4-(5-benzyl[1.3.4]thiadiazol-2-ylcarbamoyl)phenyl]cyclohexyl}-acetate (4.29 mmol, 1 eq.) are placed in 15 mL of dichloromethane in a 100 mL round-bottomed flask. 2.55 mL of trifluoroacetic acid (34.33 mmol, 8 eq.) are added and the reaction medium is stirred for 18 hours at room temperature. 1 mL of trifluoroacetic acid (13.46 mmol, 3.14 eq.) is added and the reaction medium is stirred for 3 hours. The solvent is evaporated off. The residue is taken up and washed successively with diethyl ether and ethanol to give 1.718 g of trans-(4-{4-benzyl[1.3.4]thiadiazol-2-ylcarbamoyl}-phenyl}cyclohexyl)acetic acid.

M+H+=436.

$^1$H NMR (400 MHz, DMSO-d6) δ ppm 12.46 (m, 2H), 8.02 (d, J=8 Hz, 2H), 7.41 (d, J=8 Hz, 2H), 7.38 (m, 4H), 7.30 (m, 1H), 4.39 (s, 2H), 2.57 (tt, J=12 Hz and 3.4 Hz, 1H), 2.16 (d, J=6.8 Hz, 2H), 1.89 to 1.70 (m, 5H), 1.51 (m, 2H), 1.14 (m, 2H).

EXAMPLE 9 cis- and trans-4-[4-(5-benzyl[1.3.4]thiadiazol-2-ylcarbamoyl)-phenylamino]cyclohexanecarboxylic acid (Compounds 68 and 69 of Table III)

9.1 Synthesis of tert-butyl [4-(5-benzyl[1.3.4]thiadiazol-2-ylcarbamoyl)phenyl]-carbamate 1 g of 4-tert-butoxycarbonylaminobenzoic acid (4.21 mmol, 1 eq.) is placed in 12 mL of a 5/1 mixture of dichloromethane and dimethylformamide with stirring. 0.81 g of 5-benzyl-1,3,4-thiadiazol-2-amine (4.21 mmol, 1 eq.), 0.97 g of 1-ethyl-3-(3-dimethylaminopropyl)carbodiimide hydrochloride (5.05 mmol, 1.2 eq.), 0.97 g of hydroxybenzotriazole (6.32 mmol, 1.5 eq.) and 1.74 mL of diisopropylethylamine (10.52 mmol, 2.5 eq.) are successively added. After 42 hours at room temperature, the medium is heated at 60° C. for 6 hours. 0.40 g of 1-ethyl-3-(3-dimethylaminopropyl)carbodiimide hydrochloride (2.1 mmol, 0.5 eq.) and 0.322 g of hydroxybenzotriazole (3.16 mmol, 0.5 eq.) are added. After 18 hours, the medium is diluted with dichloromethane and water. The organic phase is separated out by settling, washed with water, dried over magnesium sulfate, filtered and evaporated. The residue is chromatographed on silica gel with a gradient of ethyl acetate in heptane ranging from 0% to 50%. The organic phase is evaporated to give 0.2 g of tert-butyl [4-(5-benzyl[1.3.4]thiadiazol-2-ylcarbamoyl)phenyl]carbamate.

M+H$^+$=411.

9.2 Synthesis of 4-amino-N-(5-benzyl[1.3.4]thiadiazol-2-yl)benzamide 0.2 g of tert-butyl [4-(5-benzyl[1.3.4]thiadiazol-2-ylcarbamoyl)phenyl]carbamate (0.49 mmol, 1 eq.) is placed in 5 mL of dichloromethane. 1 mL of trifluoroacetic acid (13.54 mmol, 27.6 eq.) is added and the reaction medium is stirred for 3 days at room temperature. The solvents are evaporated off and the residue is taken up in diethyl ether and pentane to give 0.14 g of 4-amino-N-(5-benzyl[1.3.4]thiadiazol-2-yl)-benzamide acid.

M+H$^+$=311.

9.3 Synthesis of ethyl cis- and trans-4-[4-(5-benzyl[1.3.4]thiadiazol-2-ylcarbamoyl)-phenylamino]cyclohexanecarboxylate 0.14 g of 4-amino-N-(5-benzyl[1.3.4]thiadiazol-2-yl)-benzamide acid (0.4 mmol, 1 eq.) and 1.5 mL of dichloroethane are placed in a microwave tube. 0.134 g of ethyl 4-oxo-cyclohexanecarboxylate (0.79 mmol, 2 eq.), 0.15 g of sodium triacetoxyborohydride (0.99 mmol, 2.5 eq.) and 0.07 mL of acetic acid are successively added with stirring. The tube is sealed and maintained at 140° C. for 20 minutes. The reaction medium is taken up in water and ethyl acetate. After separation of the phases by settling, the organic phase is dried over magnesium sulfate, filtered and evaporated. The residue is chromatographed on silica gel with a gradient of ethyl acetate in heptane ranging from 10% to 50%.

A first fraction of 50 mg of ethyl cis-4-[4-(5-benzyl[1.3.4]thiadiazol-2-ylcarbamoyl)-phenylamino]cyclohexanecarboxylate is obtained.

M+H$^+$=465.

A second fraction of 20 mg of ethyl trans-4-[4-(5-benzyl[1.3.4]thiadiazol-2-ylcarbamoyl)-phenylamino]cyclohexanecarboxylate is obtained.

M+H$^+$=465.

9.4 Synthesis of trans-4-[4-(5-benzyl[1.3.4]thiadiazol-2-ylcarbamoyl)phenylamino]cyclohexanecarboxylic acid 50 mg of ethyl trans-4-[4-(5-benzyl[1.3.4]thiadiazol-2-ylcarbamoyl)phenylamino]cyclohexanecarboxylate (0.11 mmol, 1 eq.) are placed in 1 mL of tetrahydrofuran. 9 mg of lithium hydroxide monohydrate (0.22 mmol, 2 eq.) dissolved in 1 mL are added and stirring is continued for 18 hours. The reaction medium is diluted with water, washed with ethyl acetate and acidified with aqueous 6% sulfur dioxide solution. The solid obtained is filtered off by suction, and washed successively with water, ethanol and diethyl ether. 13 mg of trans-4-[4-(5-benzyl[1.3.4]thiadiazol-2-ylcarbamoyl)phenylamino]cyclohexanecarboxylic acid are obtained.

M+H$^+$=437.

$^1$H NMR (400 MHz, DMSO-d6) δ ppm 12.20 (m, 2H), 7.87 (d, J=9 Hz, 2H), 7.36 (m, 4H), 7.29 (m, 1H), 6.62 (d, J=9 Hz, 2H), 6.41 (d, J=7.8 Hz, 1H), 4.36 (s, 2H), 2.21 (tt, J=12 Hz and 3.4 Hz, 1H), 1.97 (m, 4H), 1.49 (m, 2H), 1.21 (m, 3H).

9.5 Synthesis of cis-4-[4-(5-benzyl[1.3.4]thiadiazol-2-ylcarbamoyl)phenylamino]cyclohexanecarboxylic acid This compound is obtained according to Preparation 9.4, starting with ethyl cis-4-[4-(5-benzyl[1.3.4]thiadiazol-2-ylcarbamoyl)phenylamino]cyclohexanecarboxylate.

M+H$^+$=437.

$^1$H NMR (400 MHz, DMSO-d6) δ ppm 12.23 (m, 2H), 7.88 (d, J=9 Hz, 2H), 7.37 (m, 4H), 7.30 (m, 1H), 6.65 (d, J=9 Hz, 2H), 6.45 (d, J=7.6 Hz, 1H), 4.36 (s, 2H), 3.49 (m, 1H), 2.45 (m, 1H), 1.91 (m, 1H), 1.77 to 1.47 (m, 6H).

EXAMPLE 10

6-[4-(5-benzyl[1.3.4]thiadiazol-2-ylcarbamoyl)phenyl]spiro[2.5]-octane-1-carboxylic acid (intermediate in the synthesis of compound 43 of Table V)

10.1 Synthesis of tert-butyl 6-(4-ethoxycarbonylphenyl)spiro[2.5]octane-1-carboxylate 5.11 g of trimethylsulfonium iodide (23.23 mmol, 4 eq.) are dissolved with stirring in 20 mL of DMSO in a 250 mL three-necked flask under a nitrogen atmosphere. 2.61 g of potassium tert-butoxide (23.23 mmol, 4 eq.) are added and the reaction medium is stirred for 3 hours. 2 g of ethyl 4-(4-tert-butoxycarbonylmethylenecyclohexyl)benzoate dissolved in 5 mL of DMSO are added and stirring is continued for 2 days. 2.56 g of trimethylsulfonium iodide (11.61 mmol, 2 eq.) are dissolved in 20 mL of DMSO in a 25 mL three-necked flask under a nitrogen atmosphere, and 1.0 g of potassium tert-butoxide (11.61 mmol, 2 eq.) is added with stirring. After 3 hours, this reaction medium is added to the 250 mL three-necked flask and stirring is continued for 18 hours. Ethyl acetate is added. The organic phase is washed with saturated aqueous ammonium chloride solution, dried over magnesium sulfate and filtered. The residue is chromatographed on silica gel with a gradient of ethyl acetate in heptane ranging from 10% to 50%. 0.159 g of tert-butyl 6-(4-ethoxycarbonylphenyl)spiro[2.5]octane-1-carboxylate is obtained.

10.2 Synthesis of tert-butyl 6-(4-carboxyphenyl)spiro[2.5]octane-1-carboxylate 0.159 g of tert-butyl 6-(4-ethoxycarbonylphenyl)spiro[2.5]octane-1-carboxylate (0.44 mmol, 1 eq.) is placed in 4 mL of a 3/1 mixture of THF/methanol in a 50 mL round-bottomed flask. 0.075 g of lithium hydroxide monohydrate (1.78 mmol; 4 eq.) dissolved in 1 mL of water is added with stirring. After 16 hours at room temperature, the reaction medium is evaporated and aqueous 6% sulfur dioxide solution is added. The precipitate is filtered off to give 0.122 g of tert-butyl 6-(4-carboxyphenyl)-spiro[2.5]octane-1-carboxylate.

10.3 Synthesis of tert-butyl 6-[4-(5-benzyl[1.3.4]thiadiazol-2-ylcarbamoyl)phenyl]-spiro[2.5]octane-1-carboxylate This compound is obtained according to Preparation 8.1, starting with tert-butyl 6-(4-carboxyphenyl)spiro[2.5]octane-1-carboxylate.

M+H$^+$=504.

10.4 Synthesis of 6-[4-(5-benzyl[1.3.4]thiadiazol-2-ylcarbamoyl)phenyl]spiro[2.5]-octane-1-carboxylic acid This compound is obtained according to Preparation 8.2, starting with tert-butyl 6-[4-(5-benzyl[1.3.4]thiadiazol-2-ylcarbamoyl)phenyl]spiro[2.5]octane-1-carboxylate.

M+H$^+$=448.

$^1$H NMR (400 MHz, DMSO-d6) δ ppm 12.82 (m, 2H), 8.04 (m, 2H), 7.48 to 7.25 (m, 7H), 4.39 (s, 1H), 2.72 (m, 1H), 2.05 to 1.46 (m, 7H), 1.29 (m, 1H), 1.12 to 0.89 (m, 3H).

EXAMPLE 11

(E)-3-{4-[4-(5-benzyl[1.3.4]thiadiazol-2-ylcarbamoyl)phenyl]cyclohexyl}acrylic acid (Compound 71 of Table IV)

11.1 Synthesis of ethyl 4-(1-oxaspiro[2.5]oct-6-yl)benzoate 0.246 g of sodium hydride (9.74 mmol, 2 eq.) is placed in 25 mL of a 1/1.5 mixture of THF/DMSO with stirring at 10° C. 2.14 g of trimethylsulfoxonium iodide (9.74 mmol, 1.2 eq.) are added. After 5 minutes, 10 mL of DMSO are added dropwise. After the evolution of gas has ceased, 2 g of ethyl 4-(4-oxocyclohexyl)benzoate (8.12 mmol, 1 eq.) dissolved in a minimum amount of a 2/1 mixture of DMSO/THF are rapidly added at room temperature. After stirring for 1 hour at room temperature and for 1 hour at 50° C., the reaction medium is diluted with 75 mL of water and extracted with ethyl acetate. The organic phases are successively washed twice with water and with brine, dried over sodium sulfate and evaporated. The residue is chromatographed on silica gel with a gradient of methanol in dichloromethane ranging from 1% to 2%. 1.8 g of ethyl 4-(1-oxaspiro[2.5]oct-6-yl)benzoate are obtained.

11.2 Synthesis of ethyl 4-(4-formylcyclohexyl)benzoate 1.4 g of ethyl 4-(1-oxaspiro[2.5]oct-6-yl)benzoate (5.38 mmol, 1.4 eq.) are placed in 40 mL of dichloromethane at 4° C. 0.229 g of boron trifluoride etherate (1.61 mmol, 0.3 eq.) is added with stirring. After 2 hours, 0.153 g of boron trifluoride etherate (1.07 mmol, 0.2 eq.) is added. After 1 hour, water is added and the reaction medium is extracted three times with dichloromethane. The organic phases are combined and washed successively with saturated aqueous sodium hydrogen carbonate solution and water. The organic phase is dried over sodium sulfate and evaporated. The residue is chromatographed on silica gel with an 88/10/2 mixture of heptane/ethyl acetate/methanol. 0.64 g of ethyl trans-4-(4-formylcyclohexyl)benzoate is obtained.

11.3 Synthesis of ethyl trans-4-[4-(E)-2-tert-butoxycarbonylvinyl)cyclohexyl]benzoate 0.682 g of tert-butyl diethylphosphonoacetate (2.7 mmol, 1.1 eq.) is placed in 5 mL of DMF at 4° C. with stirring, 0.065 g of sodium hydride (2.7 mmol, 1.1 eq.) is added. After stirring for 1 hour, 0.64 g of ethyl trans-4-(4-formylcyclohexyl)benzoate (2.46 mmol, 1 eq.) dissolved in 5 mL of DMF is added dropwise. After stirring for 18 hours, 10% potassium hydrogen sulfate solution is added. The reaction medium is extracted twice with ethyl acetate. The organic phases are combined, washed twice with water, washed with brine, dried over sodium sulfate and evaporated. The residue is chromatographed on silica gel with a gradient of ethyl acetate in heptane ranging from 10% to 20%. 0.71 g of ethyl trans-4-[4-((E)-2-tert-butoxycarbonylvinyl)cyclohexyl]benzoate is obtained.

11.4 Synthesis of trans-4-[4-(E)-2-tert-butoxycarbonylvinyl)cyclohexyl]benzoic acid 0.150 g ethyl trans-4-[4-(E)-2-tert-butoxycarbonylvinyl)cyclohexyl]benzoate (0.42 mmol, 1 eq.) is dissolved in 3 mL of a 2/1 mixture of THF/methanol. At 0° C., 0.07 g of lithium hydroxide monohydrate (1.67 mmol; 4 eq.) is added with stirring. After 3 hours at room temperature, the reaction medium is evaporated and aqueous 6% sulfur dioxide solution is added. The precipitate is filtered off and washed with water to give 0.085 g of trans-4-[4-(E)-2-tert-butoxycarbonylvinyl)cyclohexyl]benzoic acid.

11.5 Synthesis of tert-butyl trans-(E)-3-{4-[4-(5-benzyl[1.3.4]thiadiazol-2-ylcarbamoyl)-phenyl]cyclohexyl}acrylate 0.85 g of trans-4-[4-(E)-2-tert-butoxycarbonylvinyl)cyclohexyl]benzoic acid (0.26 mmol, 1 eq.) is placed in 2 mL of DMF at room temperature. 0.059 g of 5-benzyl-1,3,4-thiadiazol-2-amine (0.31 mmol, 1.2 eq.), 0.144 g of bromotris-pyrrolidinophosphonium hexafluorophosphonate (0.31 mmol, 1.2 eq.) and 0.09 mL of diisopropylethylamine (0.51 mmol, 2 eq.) are successively added. The reaction mixture is stirred for 1 day at room temperature, diluted in ethyl acetate, and washed twice with water and twice with brine. The organic phase is concentrated and dried over sodium sulfate, and the residue is chromatographed on silica gel, eluting with a gradient of ethyl acetate in heptane ranging from 20% to 33%. 0.035 g of tert-butyl trans-(E)-3-{4-[4-(5-benzyl[1.3.4]thiadiazol-2-ylcarbamoyl)phenyl]cyclohexyl}acrylate is obtained.

M+H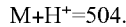=504.

11.6 Synthesis of trans-(E)-3-{4-[4-(5-benzyl[1.3.4]thiadiazol-2-ylcarbamoyl)phenyl]-cyclohexyl}acrylic acid 35 mg of tert-butyl trans-(E)-3-{4-[4-(5-benzyl[1.3.4]thiadiazol-2-ylcarbamoyl)phenyl]-cyclohexyl}acrylate (0.07 mmol, 1 eq.) are placed in 1 mL of dichloromethane. 0.5 mL of trifluoroacetic acid (6.73 mmol, 97 eq.) is added and the reaction medium is stirred for 3 hours at room temperature. The solvent is evaporated off. The resin is triturated in ethyl acetate to give 8 mg of trans-(E)-3-{4-[4-(5-benzyl[1.3.4]thiadiazol-2-ylcarbamoyl)-phenyl]cyclohexyl}acrylic acid.

M+H+=448.

$^1$H NMR (400 MHz, DMSO-d6) δ ppm 12.55 (m, 2H), 8.03 (d, J=8.4 Hz, 2H), 7.42 (d, J=8.4 Hz, 2H), 7.38 (m, 4H), 7.30 (m, 1H), 6.84 (m, 1H), 5.77 (dd, J=15.6 Hz and 3.4 Hz, 1H), 4.39 (s, 2H), 2.61 (m, 1H), 2.26 (m, 1H), 1.88 (m, 4H), 1.57 (m, 2H), 1.32 (m, 2H).

EXAMPLE 12 trans-(1R,2S/1S,2R)-2-{4-[4-(5-benzyl[1.3.4]thiadiazol-2-ylcarbamoyl)phenyl]cyclohexyl}cyclopropanecarboxylic acid (intermediate in the synthesis of compound 72 of Table IV)

12.1 Synthesis of ethyl trans-4-[4-((1S,2R/1R,2S)-2-tert-butoxycarbonylcyclopropyl)-cyclohexyl]benzoate 0.442 g of trimethylsulfoxonium iodide (2.01 mmol, 1.8 eq.) is placed in 3 mL of DMSO. 0.225 g of potassium tert-butoxide (2.01 mmol, 1.8 eq.) is added with stirring. After 3 hours at room temperature, 0.4 g of ethyl trans-4-[4-(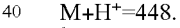-2-tert-butoxycarbonylvinyl)-cyclohexyl]benzoate (1.12 mmol, 1 eq.) dissolved in 2 mL of DMSO is added and stirring is continued for 18 hours. Brine and saturated ammonium chloride solution are successively added. The reaction medium is extracted three times with ethyl acetate. The organic phases are combined, washed successively three times with water, with brine, dried over sodium sulfate and evaporated to give 310 mg of ethyl trans-4-[4-((1S,2R/1R,2S)-2-tert-butoxycarbonylcyclopropyl)cyclohexyl]benzoate.

12.2 Synthesis of trans-4-[4-((1S,2R/1R,2S)-2-tert-butoxycarbonylcyclopropyl)cyclohexyl]-benzoic acid This compound is obtained according to Preparation 11.4, starting with ethyl trans-4-[4-((1S,2R/1R,2S)-2-tert-butoxycarbonylcyclopropyl)cyclohexyl]benzoate.
$^1$H NMR (400 MHz, DMSO-d6) δ ppm 12.76 (m, 1H), 7.86 (d, J=8.8 Hz, 2H), 7.33 (d, J=8.8 Hz, 2H), 2.57 (m, 1H), 1.83 (m, 4H), 1.50 to 1.33 (m, 12H), 1.26 (m, 2H), 1.08 (m, 1H), 0.96 to 0.74 (m, 3H).

12.3 Synthesis of ethyl trans-(1R,2S/1S,2R)-2-{4-[4-(5-benzyl[1.3.4]thiadiazol-2-ylcarbamoyl)phenyl]cyclohexyl}cyclopropanecarboxylate This compound is obtained according to Preparation 11.5 starting with trans acid.
M+H$^+$=518.

12.4 Synthesis of trans-(1R,2S/1S,2R)-2-{4-[4-(5-benzyl[1.3.4]thiadiazol-2-ylcarbamoyl)phenyl]cyclohexyl}cyclopropanecarboxylic acid This compound is obtained according to Preparation 11.6, starting with tert-butyl trans-(1R,2S/1S,2R)-2-{4-[4-(5-benzyl[1.3.4]thiadiazol-2-ylcarbamoyl)phenyl]cyclohexyl}-cyclopropanecarboxylate.
M+H+=462.
$^1$H NMR (400 MHz, DMSO-d6) δ ppm 12.81 (m, 1H), 11.97 (m, 1H), 8.01 (d, J=8 Hz, 2H), 7.38 (m, 6H), 7.30 (m, 1H), 4.39 (s, 2H), 2.59 (tt, J=12 Hz and 3 Hz, 1H), 1.85 (m, 4H), 1.50 to 1.20 (m, 5H), 1.10 (m, 1H), 0.96 (m, 1H), 0.89 to 0.75 (m, 2H).

EXAMPLE 13 trans-3-{4-[4-(5-benzyl[1.3.4]thiadiazol-2-ylcarbamoyl)phenyl]cyclo-hexyl}propionic acid (intermediate in the synthesis of compound 73 of Table IV)

13.1 Synthesis of ethyl trans-4-[4-(2-tert-butoxycarbonylethyl)cyclohexyl]benzoate 0.150 g of ethyl trans-4-[4-((E)-2-tert-butoxycarbonylvinyl)cyclohexyl]benzoate (0.42 mmol, 1 eq.) is dissolved in 15 mL of ethanol in a Parr bottle. 0.044 g of 10% palladium-on-charcoal (0.04 mmol, 0.1 eq.) is added and the medium is subjected to 50 psi of hydrogen for 5 hours. The medium is filtered through Whatman paper, washed with ethanol and evaporated to give 0.19 g of ethyl trans-4-[4-(2-tert-butoxycarbonylethyl)cyclohexyl]benzoate.

13.2 Synthesis of trans-4-[4-(2-tert-butoxycarbonylethyl)cyclohexyl]benzoic acid This compound is obtained according to Preparation 11.4, starting with ethyl trans-4-[4-(2-tert-butoxycarbonylethyl)cyclohexyl]benzoate.

13.3 Synthesis of tert-butyl trans-3-{4-[4-(5-benzyl[1.3.4]thiadiazol-2-ylcarbamoyl)-phenyl]cyclohexyl}propionate This compound is obtained according to Preparation 11.5 with a reaction time of 2 days, 1.7 eq. of bromotris-pyrrolidinophosphonium hexafluorophosphonate and 3 eq. of diisopropylethylamine, starting with trans-4-[4-(2-tert-butoxycarbonylcyclopropyl)-cyclohexyl]benzoic acid.
M+H$^+$=506.

13.4 Synthesis of 3-{4-[4-(5-benzyl[1.3.4]thiadiazol-2-ylcarbamoyl)phenyl]cyclohexyl}-propionic acid This compound is obtained according to Preparation 11.6, starting with tert-butyl trans-3-{4-[4-(5-benzyl[1.3.4]thiadiazol-2-ylcarbamoyl)phenyl]cyclohexyl}propionate.
M+H$^+$=450.
$^1$H NMR (400 MHz, DMSO-d6) δ ppm 12.83 (m, 1H), 12 (m, 1H), 8.02 (d, J=8.4 Hz, 2H), 7.40 (d, J=8.4 Hz, 2H), 7.38 (m, 4H), 7.30 (m, 1H), 4.39 (s, 2H), 2.57 (m, 1H), 2.26 (m, 1H), 1.83 (m, 4H), 1.48 (m, 4H), 1.33 (m, 1H), 1.07 (m, 2H).

EXAMPLE 14 cis-4-{4-[5-(3-chlorophenyl)[1.3.4]thiadiazol-2-ylcarbamoyl]-phenoxy}cyclohexanecarboxylic acid (Compound 59 of Table II)

14.1 Synthesis of methyl trans-4-hydroxycyclohexanecarboxylate 1 g of 4-hydroxycyclohexanecarboxylic acid (6.94 mmol, 1 eq.) is placed in 50 mL of a 4/1 mixture of toluene and methanol. 5.55 mL of trimethylsilyldiazomethane (11.10 mmol, 1.6 eq.) are added dropwise to the reaction medium with stirring. After 16 hours, the solvents are evaporated off to give 1.3 g of methyl trans-4-hydroxycyclohexanecarboxylate.

14.2 Synthesis of tert-butyl cis-4-(4-methoxycarbonylcyclohexyloxy)benzoate 1.1 g of methyl trans-4-hydroxycyclohexanecarboxylate (6.95 mmol, 1.35 eq.), 1 g of tert-butyl 4-hydroxybenzoate (5.15 mmol, 1 eq.) and 2.03 g of triphenylphosphine (7.72 mmol, 1.5 eq.) are placed in 10 mL of tetrahydrofuran at room temperature. 1.5 mL of diisopropyl azodicarboxylate (7.72 mmol, 1.5 eq.) are added dropwise to the reaction medium with stirring. After 18 hours at room temperature, the medium is concentrated to dryness and taken up in diethyl ether. The triphenylphosphine oxide is filtered off. The organic phase is washed with sodium hydroxide solution, dried over sodium sulfate, filtered and evaporated to give a residue. This residue is chromatographed on silica gel, eluting with a gradient of ethyl acetate in heptane ranging from 0% to 50%. 1.23 g of tert-butyl cis-4-(4-methoxycarbonylcyclohexyloxy)-benzoate are obtained.

14.3 Synthesis of cis-4-(4-methoxycarbonylcyclohexyloxy)benzoic acid 0.6 g of tert-butyl cis-4-(4-methoxycarbonylcyclohexyloxy)benzoate (1.79 mmol, 1 eq.) is placed in 2.5 mL of dichloromethane. The reaction medium is cooled to a temperature of 4° C. with stirring in an ice bath. 1 mL of trifluoroacetic acid (13.46 mmol, 7.5 eq.) is added and the ice bath is removed. After stirring for 5 hours at room temperature, the medium is concentrated, taken up in diethyl ether, drained and filtered to give 0.30 g of cis-4-(4-methoxycarbonylcyclohexyloxy)benzoic acid. M+H$^+$=279.

14.4 Synthesis of methyl cis-4-{4-[5-(3-chlorophenyl)[1.3.4]thiadiazol-2-ylcarbamoyl]phenoxy}cyclohexanecarboxylate 0.351 g of cis-4-(4-methoxycarbonylcyclohexyloxy)benzoic acid (1.26 mmol, 1 eq.) is placed in 5 mL of dichloromethane at room temperature. 0.42 mL of diisopropylethylamine (2.52 mmol, 2 eq.), 0.705 g of bromotris-pyrrolidinophosphonium hexafluorophosphonate (1.51 mmol, 1.2 eq.) and 0.267 g of 3-chlorophenyl-1,3,4-thiadiazol-2-amine (1.26 mmol, 1 eq.) are added successively. 2 mL of DMF are added. The reaction mixture is stirred for 1 day at room temperature, diluted in dichloromethane, and water is added. Filtration of this medium gives 0.06 g of methyl cis-4-{4-[5-(3-chlorophenyl)[1.3.4]thiadiazol-2-ylcarbamoyl]phenoxy}cyclohexanecarboxylate. The organic phase is separated out by settling, washed with water, dried over sodium sulfate, filtered and evaporated. The residue is taken up in ethanol, filtered off by suction and washed with diethyl ether. 0.090 g of methyl cis-4-{4-[5-(3-chlorophenyl)[1.3.4]thiadiazol-2-ylcarbamoyl]phenoxy}cyclohexanecarboxylate is obtained.

14.5 Synthesis of cis-4-{4-[5-(3-chlorophenyl)[1.3.4]thiadiazol-2-ylcarbamoyl]phenoxy}-cyclohexanecarboxylic acid 150 mg of methyl cis-4-{4-[5-(3-chlorophenyl)[1.3.4]thiadiazol-2-ylcarbamoyl]phenoxy}-cyclohexanecarboxylate (0.32 mmol, 1 eq.) is placed in 1 mL of tetrahydrofuran. 27 mg of lithium hydroxide monohydrate (0.64 mmol, 2 eq.) dissolved in 1 mL are added and stirring is continued for 18 hours. The reaction medium is diluted with water, washed with ethyl acetate and acidified with aqueous 6% sulfur dioxide solution. The solid obtained is filtered off by suction and washed successively with water, ethanol and diethyl ether. 96 mg of cis-4-{4-[5-(3-chlorophenyl)[1.3.4]thiadiazol-2-ylcarbamoyl]-phenoxy}cyclohexanecarboxylic acid are obtained.

M+H+=458.

$^1$H NMR (400 MHz, DMSO-d6) δ ppm 13.04 (m, 1H), 12.16 (m, 1H), 8.15 (d, J=9 Hz, 2H), 8.04 (m, 1H), 7.94 (m, 1H), 7.61 (m, 2H), 7.13 (d, J=9 Hz, 2H), 4.72 (m, 1H), 2.42 (m, 1H), 1.92 to 1.64 (m, 8H).

EXAMPLE 15 cis-4-{5-[5-(3-chlorobenzyl)[1.3.4]thiadiazol-2-ylcarbamoyl]pyridin-2-yloxy}cyclohexanecarboxylic acid (Compound 63 of Table II)

15.1 Synthesis of tert-butyl trans-4-hydroxycyclohexanecarboxylate 1.5 g of trans-4-hydroxycyclohexanecarboxylic acid (10.40 mmol, 1 eq.) are placed in 15 mL of toluene. The reaction medium is brought to reflux and 7.5 mL of di-tert-butoxymethyldimethylamine (31.32 mmol, 3 eq.) are added dropwise. After refluxing for 16 hours, the reaction medium is diluted with ethyl acetate and washed successively with saturated aqueous sodium hydrogen carbonate solution and brine. The organic phase is dried over magnesium sulfate, filtered and evaporated to give 1.63 g of tert-butyl trans-4-hydroxycyclohexanecarboxylate.

15.2 Synthesis of ethyl cis-6-(4-tert-butoxycarbonylcyclohexyloxy)nicotinate 1.63 g of tert-butyl trans-4-hydroxycyclohexanecarboxylate (8.14 mmol, 1 eq.) and 1.62 g of ethyl 6-hydroxynicotinate (10.58 mmol, 1.3 eq.) are placed in 24 mL of tetrahydrofuran at room temperature. 3.20 g of triphenylphosphine (12.21 mmol, 1.5 eq.) are added, followed by dropwise addition of 2.37 mL of diisopropyl azodicarboxylate (12.21 mmol, 1.5 eq.) to the reaction medium with stirring. After 1 hour at room temperature, the medium is concentrated to dryness and taken up in diethyl ether. The triphenylphosphine oxide is filtered off. The organic phase is washed successively with sodium hydroxide solution and than with water, dried over magnesium sulfate, filtered and evaporated to give a residue. This residue is chromatographed on silica gel, eluting with a gradient of ethyl acetate in heptane ranging from 3% to 30%. 1.3 g of ethyl cis-6-(4-tert-butoxycarbonylcyclohexyloxy)-nicotinate are obtained.

M+H+=336.

15.3 Synthesis of cis-6-(4-tert-butoxycarbonylcyclohexyloxy)nicotinic acid 1.33 g of ethyl cis-6-(4-tert-butoxycarbonylcyclohexyloxy)nicotinate (3.97 mmol, 1 eq.) are dissolved in 60 mL of a 1/1 mixture of THF/methanol. At 0° C., 0.333 g of lithium hydroxide monohydrate (7.93 mmol; 2 eq.) is added with stirring. After stirring for 16 hours at room temperature, the reaction medium is evaporated and aqueous 6% sulfur dioxide solution is added. The precipitate formed is filtered off and washed with water to give 1.25 g of cis-6-(4-tert-butoxycarbonylcyclohexyloxy)nicotinic acid.

M+H+=322.

15.4 Synthesis of tert-butyl cis-4-{5-[5-(3-chlorobenzyl)[1.3.4]thiadiazol-2-ylcarbamoyl]-pyridin-2-yloxy}cyclohexanecarboxylate 0.321 g of cis-6-(4-tert-butoxycarbonylcyclohexyloxy)nicotinic acid (1 mmol, 1 eq.) is placed in 50 mL of acetonitrile at room temperature. 0.33 mL of diisopropylethylamine (2 mmol, 2 eq.), 0.466 g of bromotris-pyrrolidinophosphonium hexafluorophosphonate (1 mmol, 1 eq.) and 0.270 g of 5-(3-chlorobenzyl)[1.3.4]thiadiazol-2-ylamine (1.2 mmol, 1.2 eq.) are successively added with stirring. After 4 days at room temperature, the reaction medium is evaporated and 15 mL of DMF are added. The medium is stirred again for 18 hours, diluted in ethyl acetate, washed three times with brine, dried over magnesium sulfate, filtered and evaporated. The residue is chromatographed on silica gel, eluting with a gradient of ethyl acetate in heptane ranging from 5% to 50%. After evaporating the fractions of interest, the residue is chromatographed on silica gel with a gradient of ethyl acetate in dichloromethane ranging from 2% to 20%. 0.262 g of tert-butyl cis-4-{5-[5-(3-chlorobenzyl)[1.3.4]thiadiazol-2-ylcarbamoyl]pyridin-2-yloxy}cyclohexanecarboxylate is obtained.

15.5 Synthesis of cis-4-{5-[5-(3-chlorobenzyl)[1.3.4]thiadiazol-2-ylcarbamoyl]pyridin-2-yloxy}cyclohexanecarboxylic acid 0.264 g of tert-butyl cis-4-{5-[5-(3-chlorobenzyl)[1.3.4]thiadiazol-2-ylcarbamoyl]pyridin-2-yloxy}cyclohexanecarboxylate (0.5 mmol, 1 eq.) is placed in 5 mL of dichloromethane with stirring. 0.37 mL of trifluoroacetic acid (4.99 mmol, 10 eq.) is added slowly. After stirring for 18 hours at room temperature, the medium is concentrated, taken up and evaporated successively with ethanol and dichloromethane. The residue is triturated with diethyl ether, drained and filtered to give 0.213 g of cis-4-{5-[5-(3-chlorobenzyl)-[1.3.4]thiadiazol-2-ylcarbamoyl]pyridin-2-yloxy}cyclohexanecarboxylic acid.

M+H$^+$=473.

$^1$H NMR (400 MHz, DMSO-d6) δ ppm 12.57 (m, 2H), 8.88 (d, J=2.4 Hz, 1H), 8.32 (dd, J=8.8 Hz and 2.4 Hz, 1H), 7.47 (m, 1H), 7.37 (m, 3H), 6.94 (d, J=9 Hz, 1H), 5.27 (m, 1H), 4.42 (s, 2H), 2.41 (m, 1H), 1.92 to 1.65 (m, 8H).

EXAMPLE 16 trans-{4-[4-(5-benzyl[1.3.4]thiadiazol-2-ylcarbamoyl)phenyl]cyclohexyloxy}acetic acid (Compound 46 of Table V)

16.1 Synthesis of trans-4-(4-allyloxyphenyl)cyclohexanol 10.6 g of trans-4-(4-hydroxycyclohexyl)phenol (55.13 mmol, 14 eq.) are dissolved in 150 mL of a 2/1 mixture of DMF and acetone, to which are added with stirring 4.8 mL of allyl bromide (55.13 mmol, 14 eq.), followed by 11.43 g (82.7, 1.5 eq.) of potassium carbonate. After 3 days, the reaction medium is poured into 300 mL of water, filtered, washed with water and dried to give 12.6 g of trans-4-(4-allyloxyphenyl)cyclohexanol.

16.2 Synthesis of tert-butyl trans-[4-(4-allyloxyphenyl)cyclohexyloxy]acetate 2 g of trans-4-(4-allyloxyphenyl)cyclohexanol (8.61 mmol, 1 eq.) are dissolved in 50 mL of a 1/1 mixture of toluene/aqueous 32% sodium hydroxide solution, to which are added with stirring 3.81 mL (25.83 mmol, 3 eq.) of tert-butyl bromoacetate, followed by addition of 0.292 g of tetrabutylammonium bromide (0.86 mmol, 0.1 eq.). After 18 hours, the reaction medium is diluted with ethyl acetate and washed with water. The aqueous phase is extracted with ethyl acetate. The organic phases are combined, washed with brine, dried over magnesium sulfate, filtered and evaporated. The residue is chromatographed on silica gel, eluting with a gradient of ethyl acetate in heptane ranging from 3% to 30%. 2.9 g of tert-butyl trans-4-(4-allyloxyphenyl)cyclohexyloxy]-acetate are obtained.

16.3 Synthesis of tert-butyl trans-[4-(4-hydroxyphenyl)cyclohexyloxy]acetate 3.6 g of tert-butyl trans-[4-(4-allyloxyphenyl)cyclohexyloxy]acetate are dissolved in 70 mL of dichloromethane, to which are added with stirring 4.87 g of barbituric acid (31.17 mmol, 3 eq.) and then 1.20 g of tetrakis(triphenylphosphine)palladium (1.04 mmol, 0.1 eq.). The reaction medium is refluxed for 3 hours. After 16 hours at room temperature, the reaction medium is diluted with dichloromethane and washed with brine. The aqueous phase is extracted with dichloromethane. The organic phases are combined, washed with brine, dried over magnesium sulfate, filtered and evaporated. The residue is chromatographed on silica gel, eluting with a gradient of ethyl acetate in heptane ranging from 2% to 20%. 3.2 g of tert-butyl trans-[4-(4-hydroxyphenyl)cyclohexyloxy]acetate are obtained.

16.4 Synthesis of tert-butyl trans-4-(4-trifluoromethanesulfonyloxyphenyl)cyclohexyloxy]acetate 3.2 g of tert-butyl trans-[4-(4-hydroxyphenyl)cyclohexyloxy]acetate (10.44 mmol, 1 eq.) are dissolved in 50 mL of dichloromethane and cooled in an ice bath. 4.4 mL of triethylamine (31.33 mmol, 3 eq.) are added, followed by dropwise addition of 2.6 mL of triflic anhydride (15.67 mmol, 1.5 eq.). After stirring for 30 minutes, the ice bath is removed and stirring is continued for 16 hours. The reaction medium is diluted with dichloromethane and washed with saturated aqueous ammonium chloride solution. The aqueous phase is extracted with dichloromethane. The organic phases are combined, washed with saturated aqueous sodium hydrogen carbonate solution, dried over magnesium sulfate, filtered and evaporated. The residue is chromatographed on silica gel, eluting with a gradient of ethyl acetate in heptane ranging from 4% to 40%. 3.3 g of tert-butyl trans-[4-(4-trifluoromethanesulfonyloxyphenyl)cyclohexyloxy]acetate are obtained.

16.5 Synthesis of trans-4-(4-tert-butoxycarbonylmethoxycyclohexyl)benzoic acid 250 mg of tert-butyl trans-[4-(4-trifluoromethanesulfonyloxyphenyl)cyclohexyloxy]-acetate are placed in 1.5 mL of dioxane in a microwave tube. 83 mg of hexacarbonylmolybdenum (0.32 mmol, 0.5 eq.), 14 mg of palladium diacetate (0.06 mmol, 0.1 eq.), 35 mg of DPPF (0.06 mmol, 0.1 eq.), 154 mg of DMAP (1.26 mmol, 2 eq.), 0.25 mL of DIEA (1.45 mmol, 2.3 eq.) and 0.23 mL of water are successively added. The tube is sealed and heated by microwave at 120° C. for 30 minutes. The reaction medium is diluted with dichloromethane and washed three times with saturated aqueous sodium carbonate solution. The reaction medium is diluted with diethyl ether and washed with aqueous 5N HCl solution. The organic phases are combined and evaporated to give 270 mg of trans-4-(4-tert-butoxycarbonylmethoxycyclohexyl)benzoic acid, which is used without further purification in the following step.

M+H$^+$=293.

16.6 Synthesis of tert-butyl trans-{4-[4-(5-benzyl[1.3.4]thiadiazol-2-ylcarbamoyl)phenyl]-cyclohexyloxy}acetate 0.6 g of trans-4-(4-tert-butoxycarbonylmethoxycyclohexyl)benzoic acid (1.79 mmol, 1 eq.) is placed in 8 mL of dichloromethane with stirring. 0.7 mL of diisopropylethylamine (4.49 mmol, 2.5 eq.), 0.275 g of hydroxybenzotriazole (1.79 mmol, 1 eq.) and 0.413 g of 1-ethyl-3-(3-dimethylaminopropyl)carbodiimide hydrochloride (2.15 mmol, 1.2 eq.) are successively added, followed, after 10 minutes, by addition of 0.377 g of 5-benzyl-1,3,4-thiadiazol-2-amine (1.97 mmol, 1.1 eq.). After 16 hours, 0.137 g of hydroxybenzotriazole (0.895 mmol, 0.5 eq.) and 0.172 g of 1-ethyl-3-(3-dimethylaminopropyl)carbodiimide hydrochloride (0.17 mmol, 0.5 eq.) are added. After 18 hours, the medium is evaporated, diluted with ethyl acetate and washed three times with brine. The organic phase is dried over sodium sulfate, filtered and evaporated. The residue is chromatographed on silica gel with a gradient of methanol in dichloromethane ranging from 0% to 2%. 0.09 g of tert-butyl trans-{4-[4-(5-benzyl[1.3.4]thiadiazol-2-ylcarbamoyl)phenyl]cyclohexyloxy}acetate is obtained.

M+H+=508.

16.7 Synthesis of trans-{4-[4-(5-benzyl[1.3.4]thiadiazol-2-ylcarbamoyl)phenyl]cyclohexyloxy}acetic acid 90 mg of tert-butyl trans-{4-[4-(5-benzyl[1.3.4]thiadiazol-2-ylcarbamoyl)phenyl]cyclohexyloxy}acetate (0.18 mmol, 1 eq.) are placed in 1 mL of dichloromethane. 0.13 mL of trifluoroacetic acid (1.77 mmol, 10 eq.) is added and the reaction medium is stirred for 18 hours at room temperature. The solvent is evaporated off. The residue is triturated in ethyl acetate and methanol to give 15 mg of trans-{4-[4-(5-benzyl [1.3.4]thiadiazol-2-ylcarbamoyl)phenyl]cyclohexyloxy}acetic acid.

M+H$^+$=452.

$^1$H NMR (400 MHz, DMSO-d6) δ ppm 12.68 (m, 2H), 8.01 (d, J=8.3 Hz, 2H), 7.41 (d, J=8.3 Hz, 2H), 7.37 (m, 4H), 7.29 (m, 1H), 4.39 (s, 2H), 4.06 (s, 2H), 3.40 (m, 1H), 2.61 (tt, J=12 Hz and 3.4 Hz, 1H), 2.13 (m, 2H), 1.84 (m, 2H), 1.51 (m, 2H), 1.32 (m, 2H).

EXAMPLE 17 trans-5-[4-(4-carboxymethylcyclohexyl)benzoylamino][1.3.4]thiadiazole-2-carboxylic acid (Compound 50 of Table 1)

17.1 Synthesis of ethyl trans-5-[4-(4-tert-butoxycarbonylmethylcyclohexyl)benzoylamino][1.3.4]thiadiazole-2-carboxylate 0.8 g of trans-4-(4-tert-butoxycarbonylmethylcyclohexyl) benzoic acid (2.51 mmol, 1 eq.) is placed in 12 mL of dimethylformamide at room temperature in a microwave tube. 0.769 g of hydroxybenzotriazole (5.02 mmol, 2 eq.), 0.962 g of 1-ethyl-3-(3-dimethylaminopropyl)carbodiimide hydrochloride (5.02 mmol, 2 eq.) and 0.522 g of ethyl 5-amino [1.3.4]thiadiazole-2-carboxylate (3.01 mmol, 1.2 eq.) are successively added with stirring. The tube is sealed and the reaction mixture is heated for 30 minutes at 100° C. The reaction medium is diluted with ethyl acetate, washed three times with brine, dried over sodium sulfate, filtered and evaporated. The residue is chromatographed on silica gel, eluting with a gradient of methanol in dichloromethane ranging from 0% to 2%. The fractions of interest are evaporated and triturated in ethyl acetate. The solid obtained is dried to give 0.28 g of ethyl trans-5-[4-(4-tert-butoxy-carbonylmethylcyclohexyl)benzoylamino][1.3.4]thiadiazole-2-carboxylate,

M+H+=475.

17.2 Synthesis of trans-5-[4-(4-tert-butoxycarbonylmethylcyclohexyl)benzoylamino]-[1.3.4]thiadiazole-2-carboxylic acid This compound is obtained according to Preparation 11.4, starting with ethyl trans-5-[4-(4-tert-butoxycarbonylmethylcyclohexyl)benzoylamino][1.3.4]thiadiazole-2-carboxylate.

17.3 Synthesis of trans-5-[4-(4-carboxymethylcyclohexyl)benzoylamino][1.3.4]thiadiazole-2-carboxylic acid This compound is obtained according to Preparation 11.6, starting with trans-5-[4-(4-tert-butoxycarbonylmethylcyclohexyl)benzoylamino][1.3.4]thiadiazole-2-carboxylic acid.

$^1$H NMR (400 MHz, DMSO-d6) δ ppm 12.83 (m, 1H), 12.11 (m, 1H), 9.23 (s, 1H), 9.07 (m, 2H), 7.46 (m, 2H), 2.76 to 2.45 (m, 1H), 2.45 to 2.11 (m, 2H), 1.94 to 1.45 (m, 7H), 1.17 (m, 1H).

EXAMPLE 18 cis-4-[4-(5-cyclopentyloxymethyl[1.3.4]thiadiazol-2-ylcarbamoyl)-phenoxy]cyclohexanecarboxylic acid (Compound 67 of Table II)

18.1 Synthesis of cyclopentyloxyacetic acid hydrazide 2.60 g of cyclopentyloxyacetic acid (18.03 mmol, 1.0 eq.) are placed in 50 mL of dichloromethane at room temperature with stirring. 2.86 g of tert-butyl hydrazinecarboxylate (21.64 mmol, 1.2 eq.), 2.437 g of hydroxybenzotriazole (18.03 mmol, 1.0 eq.), 4.148 g of 1-ethyl-3-(3-dimethylaminopropyl)carbodiimide hydrochloride (21.64 mmol, 1.2 eq.) and 4.08 mL of diisopropylethylamine (23.44 mmol, 1.3 eq.) are successively added with stirring. After 18 hours, the reaction medium is diluted with dichloromethane and washed twice with water. The organic phase is dried over sodium sulfate, filtered and evaporated. The residue is dissolved in 60 mL of dichloromethane. 15 mL of trifluoroacetic acid (201.93 mmol, 11.20 eq.) are added. The reaction medium is stirred for 2 hours and concentrated under vacuum. The residue is chromatographed on silica gel, eluting with a dichloromethane/methanol/aqueous ammonia gradient ranging from 99/1/0.1 to 95/5/0.5. 2.7 g of cyclopentyloxyacetic acid hydrazide are obtained.

18.2 Synthesis of methyl cis-4-[4-(5-cyclopentyloxymethyl[1.3.4]thiadiazol-2-ylcarbamoyl)phenoxy]cyclohexanecarboxylate 0.4 g of cis-4-(4-methoxycarbonylcyclohexyloxy)benzoic acid is placed in 10 mL of dichloromethane with stirring, at room temperature, under a nitrogen atmosphere. 0.18 mL of oxalyl chloride (2.16 mmol, 1.5 eq.) and 2 drops of dimethylformamide are successively added. The reaction medium is stirred for 2 hours and concentrated under vacuum. The methyl cis-4-(4-chlorocarbonylphenoxy)cyclohexanecarboxylate formed is dissolved in 15 mL of acetonitrile and placed under nitrogen. The mixture is cooled in an ice bath and 0.210 g of potassium thiocyanate (2.16 mmol, 1.5 eq.) is added. The reaction mixture is stirred at room temperature for 1 hour 30 minutes. 0.455 g of cyclopentyloxyacetic acid hydrazide (2.87 mmol, 2 eq.) dissolved in 5 mL of acetonitrile is then added to the methyl cis-4-(4-isothiocyanatocarbonylphenoxy)cyclohexanecarboxylate obtained and the mixture is refluxed for 2 hours 30 minutes and then left to stand at room temperature for 36 hours. The precipitate formed is filtered off and washed with acetonitrile. 0.450 g of methyl cis-4-[4-(5-cyclopentyloxymethyl[1.3.4]thiadiazol-2-ylcarbamoyl)phenoxy]cyclohexanecarboxylate is obtained.

M+H$^+$=460.

18.3 Synthesis of cis-4-[4-(5-cyclopentyloxymethyl[1.3.4]thiadiazol-2-ylcarbamoyl)-phenoxy]cyclohexanecarboxylic acid 0.446 g of methyl cis-4-[4-(5-cyclopentyloxymethyl [1.3.4]thiadiazol-2-ylcarbamoyl)-phenoxy]cyclohexanecarboxylate (0.97 mmol, 1 eq.) is placed in 10 mL of THF with stirring, at room temperature, 0.111 g of lithium hydroxide monohydrate (2.64 mmol, 2.7 eq.) dissolved in 10 mL of water is added and the mixture is stirred for 36 hours and left to stand for 48 hours. Aqueous 1N hydrochloric acid solution is then added to acidic pH. The precipitate formed is filtered off and washed with water and with ethanol. 0.320 g of cis-4-[4-(5-cyclopentyloxymethyl[1.3.4]thiadiazol-2-ylcarbamoyl)phenoxy]-cyclohexanecarboxylic acid is obtained.

M+H⁺=445.

¹H NMR (400 MHz, DMSO-d6) δ ppm 12.48 (m, 2H), 8.09 (d, J=9 Hz, 2H), 7.09 (d, J=9 Hz, 2H), 4.79 (s, 2H), 4.69 (m, 1H), 4.08 (m, 1H), 2.40 (m, 1H), 1.89 to 1.46 (m, 16H).

EXAMPLE 19 trans-{4-[4-(5-cyclopentyloxymethyl[1.3.4]thiadiazol-2-ylcarbamoyl)-phenyl]cyclohexyl}acetic acid (Compound 37 of Table I)

0.330 g of trans-4-(4-tert-butoxycarbonylmethylcyclohexyl)benzoic acid is placed in 10 mL of dichloromethane with stirring, at room temperature, under a nitrogen atmosphere. 0.12 mL of oxalyl chloride (1.42 mmol, 1.4 eq.) and 2 drops of dimethylformamide are successively added. The reaction medium is stirred for 2 hours and concentrated under vacuum. The tert-butyl trans-4-(4-chlorocarbonylphenyl)cyclohexaneacetate formed is dissolved in 8 mL of acetonitrile and placed under nitrogen. The mixture is cooled in an ice bath and 0.17 g of potassium thiocyanate (1.75 mmol, 1.7 eq.) is added. The reaction mixture is stirred at room temperature for 1 hour 30 minutes. 0.380 g of cyclopentyloxyacetic acid hydrazide (2.40 mmol, 2.32 eq.) dissolved in 5 mL of acetonitrile is then added and the mixture is refluxed for 2 hours 30 minutes and then left to stand at room temperature for 36 hours. The precipitate formed is filtered off and washed with acetonitrile. The filtrate is diluted with dichloromethane and washed with water. The organic phase is dried over sodium sulfate and concentrated under vacuum. The residue is dissolved in 5 mL of dichloromethane; 3 mL of trifluoroacetic acid are added and the reaction medium is stirred for 1 hour 30 minutes and concentrated under vacuum. After triturating in methanol, ethanol and ethyl acetate, the residue is chromatographed on silica gel, eluting with a gradient of methanol in dichloromethane ranging from 3% to 5%. After triturating in ethanol, 0.070 g of trans-{4-[4-(5-cyclopentyloxymethyl [1.3.4]thiadiazol-2-ylcarbamoyl)phenyl]cyclohexyl}acetic acid is obtained.

Cyclohexanecarboxylic acid.

M+H⁺=444.

¹H NMR (400 MHz, DMSO-d6) δ ppm 12.90 to 12.00 (m, 1H), 8.06 (m, 2H), 7.43 (m 2H), 4.80 (s, 2H), 4.09 (m, 1H), 2.59 (m, 1H), 2.17 (d, J=6.1 Hz, 2H), 1.92 to 1.45 (m, 15H), 1.15 (m, 2H).

EXAMPLE 20

(1S,3S/1R,3R)-3-phenoxycyclohexanecarboxylic acid hydrazide (intermediate for the synthesis of compound 44 of Table I)

20.1 Synthesis of ethyl (1S,3S/1R,3R)-3-hydroxycyclohexanecarboxylate 3 g of ethyl 3-oxocyclohexanecarboxylate (17.63 mmol, 1 eq.) are placed in 30 mL of methanol. The reaction medium is cooled using an ice bath with stirring and 0.733 g of sodium borohydride (19.39 mmol, 1.1 eq.) is then added portionwise. After 4 hours, the reaction medium is poured into water and extracted three times with dichloromethane. The organic phases are combined, dried over magnesium sulfate, filtered and evaporated to give 2.61 g of ethyl (1S,3S/1R,3R)-3-hydroxycyclohexanecarboxylate.

20.2 Synthesis of ethyl (1S,3S/1R,3R)-3-phenoxycyclohexanecarboxylate 1.88 g of ethyl (1S,3S/1R,3R)-3-hydroxycyclohexanecarboxylate are placed in 33 mL of THF. 1.54 g of phenol (16.35 mmol, 1.5 eq.) and 4.29 g of triphenylphosphine (16.35 mmol, 1.5 eq.) are successively added with stirring. The reaction medium is cooled in an ice bath and 3.31 g of diethyl azodicarboxylate (16.35 mmol, 1.5 eq.) are added dropwise. After stirring for 18 hours, the reaction medium is poured into water and extracted twice with ethyl acetate. The organic phases are combined, dried over magnesium sulfate, filtered and evaporated. The residue is chromatographed on silica gel, eluting with a gradient of dichloromethane in heptane ranging from 40% to 100%. 0.369 g of ethyl (1S,3S/1R,3R)-3-phenoxycyclohexanecarboxylate is obtained.

20.3 Synthesis of (1S,3S/1R,3R)-3-phenoxycyclohexanecarboxylic acid 0.369 g of ethyl (1S,3S/1R,3R)-3-phenoxycyclohexanecarboxylate (1.49 mmol, 1 eq.) is placed in 15 mL a 1/1/1 mixture of THF/methanol/water with stirring. 0.249 g of lithium hydroxide monohydrate (5.94 mmol, 4 eq.) is added. After stirring for 16 hours, the reaction medium is evaporated, taken up in water and aqueous 6% sulfur dioxide solution is added. The aqueous phase is extracted twice with dichloromethane. The organic phases are combined, dried over magnesium sulfate, filtered and evaporated. 0.274 g of (1S,3S/1R,3R)-3-phenoxycyclohexanecarboxylic acid is obtained.

20.4 Synthesis of tert-butyl N'-((1S,3S/1R,3R)-3-phenoxycyclohexanecarbonyl)-hydrazinecarboxylate 0.274 g of (1S,3S/1R,3R)-3-phenoxycyclohexanecarboxylic acid (1.24 mmol, 1.0 eq.) is placed in 3.5 mL of dichloromethane at room temperature with stirring. 0.197 g of tert-butyl hydrazinecarboxylate (1.49 mmol, 1.2 eq.), 0.168 g of hydroxybenzotriazole (1.24 mmol, 1.0 eq.), 0.286 g of 1-ethyl-3-(3-dimethylaminopropyl)carbodiimide hydrochloride (1.49 mmol, 1.2 eq.) and 0.27 mL of diisopropylethylamine (1.62 mmol, 1.3 eq.) are successively added with stirring. After 18 hours, the reaction medium is diluted with dichloromethane and washed successively with water, saturated aqueous sodium hydrogen carbonate solution and water. The organic phase is dried over magnesium sulfate, filtered and evaporated, 0.45 g of tert-butyl N'-((1S,3S/1R,3R)-3-phenoxycyclohexanecarbonyl)hydrazinecarboxylate is obtained.

20.5 Synthesis of (1S,3S/1R,3R)-3-phenoxycyclohexanecarboxylic acid hydrazide 0.45 g of tert-butyl N'-((1S,3S/1R,3R)-3-phenoxycyclohexanecarbonyl)hydrazinecarboxylate is placed in 2 mL of dichloromethane and 1.5 mL of trifluoroacetic acid are added. After stirring for 2 hours 30 minutes, the reaction medium is evaporated to dryness to give 0.35 g of (1S,3S/1R,3R)-3-phenoxycyclohexanecarboxylic acid hydrazide.

M+H⁺=235.

EXAMPLE 21

(trans-4-{4-[(5-{[(3R,6S/3S,6R)-5-ethoxyoctahydropentalen-2-yl]-methyl}-1,3,4-thiadiazol-2-yl)carbamoyl]phenyl}cyclohexyl)acetic acid (Compound 45 of Table I)

21.1 Synthesis of (3R,6S/3S,6R)-5,5-dimethylhydro-1'H-spiro[1,3-dioxane-2,2'-pentalen]-5'(3'H)-one 5 g of hydropentalene-2,5-dione (36.19 mmol, 1 eq.), 377 g of 2,2-dimethyl-1,3-propanediol (36.19 mmol, 1 eq.) and 0.069 g of para-toluenesulfonic acid (0.36 mmol, 0.01 eq.) in 50 mL of toluene are refluxed for 18 h. The medium is diluted in ethyl acetate and washed successively with aqueous 1N sodium hydroxide solution, water and brine. The organic phase is dried over sodium sulfate, filtered and evaporated. The residue is chromatographed on silica gel, eluting with a gradient of ethyl acetate in heptane ranging from 30% to 33%. 3.7 g of (3R,6S/3S,6R)-5,5-dimethylhydro-1'H-spiro[1,3-dioxane-2,2'-pentalen]-5'(3'H)-one are obtained.

21.2 Synthesis of ethyl (2E)[(3R,6S/3S,6R)-5,5-dimethylhydro-1'H-spiro[1,3-dioxane-2,2'-pentalen]-5'(3'H)-ylidene]ethanoate 2.4 g of triethyl phosphonoacetate (10.7 mmol, 1.2 eq.) are placed in 30 mL of THF. This solution is cooled, with stirring, using an ice bath, and 0.428 g of sodium hydride (10.7 mmol, 1.2 eq.) as a 60% dispersion in mineral oil is added. After 30 minutes, 2 g of (3R,6S/3S,6R)-5,5-dimethylhydro-1'H-spiro[1,3-dioxane-2,2'-pentalen]-5'(3'H)-one (8.92 mmol, 1 eq.) dissolved in 20 mL of THF are added. The ice bath is removed and stirring is continued for 16 hours. The reaction medium is neutralized with aqueous ammonium chloride solution and extracted three times with dichloromethane. The organic phases are combined and washed twice with water. The organic phase is dried over sodium sulfate, filtered and evaporated. The residue is chromatographed on silica gel, eluting with a mixture of ethyl acetate and heptane in a 1/2 ratio. 1.7 g of ethyl ($2^E$)-[(3R,6S/3S,6R)-5,5-dimethylhydro-1'H-spiro[1,3-dioxane-2,2'-pentalen]-5'(3'H)-ylidene]ethanoate are obtained.

21.3 Synthesis of ethyl [(3R,6S/3S,6R)-5,5-dimethylhexahydro-1'H-spiro[1,3-dioxane-2,2'-pentalen]-5'-yl]acetate 2.1 g of ethyl ($2^E$)[(3R,6S/3S,6R)-5,5-dimethylhydro-1'H-spiro[1,3-dioxane-2,2'-pentalen]-5'(3'H)-ylidene]ethanoate (7.13 mmol, 1 eq.) are placed in 40 mL of ethanol in a Parr bottle. 0.152 g of 10% palladium-on-charcoal (0.14 mmol, 0.02 eq.) is added and the Parr bottle is subjected to 50 psi of hydrogen for 5 hours. After filtering through Whatman paper and evaporating off the ethanol, 2 g of ethyl [(3R,6S/3S,6R)-5,5-dimethylhexahydro-1'H-spiro[1,3-dioxane-2,2'-pentalen]-5'-yl]acetate are obtained.

21.4 Synthesis of [(3R,6S/3S,6R)-5,5-dimethylhexahydro-1'H-spiro[1,3-dioxane-2,2'-pentalen]-5'-yl]acetic acid This compound is obtained according to Preparation 20.3. 0.637 g of [(3R,6S and 3S,6R)-5,5-dimethylhexahydro-1'H-spiro[1,3-dioxane-2,2'-pentalen]-5'-yl]acetic acid is obtained starting with ethyl [(3R,6S/3S,6R)-5,5-dimethylhexahydro-1'H-spiro[1,3-dioxane-2,2'-pentalen]-5'-yl]acetate.

21.5 Synthesis of tert-butyl 2-{[(3R,6S/3S,6R)-5,5-dimethylhexahydro-1'H-spiro[1,3-dioxane-2,2'-pentalen]-5'-yl]acetyl}hydrazinecarboxylate 0.637 g of [(3R,6S)-5,5-dimethylhexahydro-1'H-spiro[1,3-dioxane-2,2'-pentalen]-5'-yl]acetic acid (2.37 mmol, 1.0 eq.) is placed in 15 mL of dichloromethane at room temperature with stirring. 0.377 g of tert-butyl hydrazinecarboxylate (2.85 mmol, 1.2 eq.), 0.321 g of hydroxybenzotriazole (2.37 mmol, 1.0 eq.), 0.546 g of 1-ethyl-3-(3-dimethylaminopropyl)carbodiimide hydrochloride (2.85 mmol, 1.2 eq.) and 0.51 mL of diisopropylethylamine (3.09 mmol, 1.3 eq.) are successively added with stirring. After 18 hours, the reaction medium is diluted with dichloromethane and washed twice with water. The organic phase is dried over sodium sulfate, filtered and evaporated. 0.910 g of tert-butyl 2-{[(3R,6S/3S,6R)-5,5-dimethylhexahydro-1'H-spiro[1,3-dioxane-2,2'-pentalen]-5'-yl]acetyl}hydrazinecarboxylate is obtained.

21.6 Synthesis of 2-[(3R,6S/3S,6R)-5,5-dimethylhexahydro-1'H-spiro[1,3-dioxane-2,2'-pentalen]-5'-yl]acetohydrazide This compound is obtained according to preparation 20.5. 0.77 g of 2-[(3R,6S/3S,6R)-5,5-dimethylhexahydro-1'H-spiro[1,3-dioxane-2,2'-pentalen]-5-yl]acetohydrazide is obtained starting with tert-butyl 2-{[(3R,6S/3S,6R)-5,5-dimethylhexahydro-1'H-spiro[1,3-dioxane-2,2'-pentalen]-5'-yl]acetyl}hydrazinecarboxylate.

21.7 Synthesis of tert-butyl (trans-4-{4-[(5-{[(3R,6S/3S,6R)-5-ethoxyoctahydropentalen-2-yl]methyl}-1,3,4-thiadiazol-2-yl)carbamoyl]phenyl}cyclohexyl)acetate 0.400 g of trans-4-(4-tert-butoxycarbonylmethylcyclohexyl)benzoic acid (1.26 mmol, 1 eq.) is placed in 8 mL of dichloromethane with stirring, at room temperature, under a nitrogen atmosphere. 0.21 mL of oxalyl chloride (2.51 mmol, 2 eq.) and 2 drops of dimethylformamide are successively added. The reaction medium is stirred for 2 hours and concentrated under vacuum. The tert-butyl trans-4-(4-chlorocarbonylphenyl)cyclohexaneacetate formed is dissolved in 15 mL of acetone and placed under nitrogen. The mixture is cooled in an ice bath and 0.147 g of potassium thiocyanate (1.51 mmol, 1.2 eq.) is added. The reaction mixture is stirred at room temperature for 2 hours. 0.669 g of 2-[(3R,6S/3S,6R)-5,5-dimethylhexahydro-1'H-spiro[1,3-dioxane-2,2'-pentalen]-5'-yl]acetohydrazide (2.37 mmol, 1.89 eq.) dissolved in 10 mL of acetone is then added and the mixture is refluxed for 16 hours. The reaction medium is diluted with dichloromethane and washed three times with water. The organic phase is dried over sodium sulfate and concentrated under vacuum. The residue is chromatographed on silica gel, eluting with a mixture of ethyl acetate and heptane in a 1/2 ratio. After triturating in ethanol, 0.286 g of tert-butyl (trans-4-{4-[(5-{[(3R,6S/3S,6R)-5-ethoxyoctahydropentalen-2-yl]methyl}-1,3,4-thiadiazol-2-yl)carbamoyl]phenyl}cyclohexyl)acetate is obtained.

21.8 Synthesis of (trans-4-{4-[(5-{[(3R,6S/3S,6R)-5-ethoxyoctahydropentalen-2-yl]-methyl}-1,3,4-thiadiazol-2-yl)carbamoyl]phenyl}cyclohexyl)acetic acid 0.286 g of tert-butyl (trans-4-{4-[(5-{[(3R,6S/3S,6R)-5-ethoxyoctahydropentalen-2-yl]-methyl}-1,3,4-thiadiazol-2- yl)carbamoyl]phenyl}cyclohexyl)acetate (0.46 mmol, 1 eq.) is placed in 4 mL of dichloromethane and 1 mL of trifluoroacetic acid (5 mmol, 10.9 eq.) is added. After stirring for 16 hours, the reaction medium is evaporated to dryness and saturated aqueous sodium hydrogen carbonate solution is added. The aqueous phase is extracted three times with dichloromethane. The residue is chromatographed on silica gel, eluting with a dichloromethane/methanol/acetic acid gradient ranging from 97/3/0.3 to 95/5/0.5. After triturating in water, ethanol and methanol 0.024 g of (trans-4-{4-[(5-{[(3R,6S/3S,6R)-5-ethoxyoctahydropentalen-2-yl]methyl}-1,3,4-thiadiazol-2-yl)-carbamoyl]phenyl}cyclohexyl)acetic acid is obtained.

M+H$^+$=511.

$^1$H NMR (400 MHz, DMSO-d6) δ ppm 12.9 to 11.7 (m, 2H), 8.03 (m, 2H), 7.42 (m, 2H), 3.83 (m, 1H), 3.35 (m, 2H), 3.02 (m, 2H), 2.64 to 1.94 (m, 8H), 1.93 to 1.00 (m, 18H).

EXAMPLE 22 trans-4-[4-(5-benzyl[1.3.4]thiadiazol-2-ylcarbamoyl) phenyl]cyclohexanecarboxylic acid (Compound 70 of Table III)

22.1 Synthesis of ethyl 4-(4-trifluoromethanesulfonyloxycyclohex-3-enyl)benzoate At −70° C., 3.3 mL of diisopropylethylamine (23.55 mmol, 1.16 eq.) are placed in 50 mL of THF, and 9.3 mL of n-BuLi (1.14 eq.) as a 2.5 M solution in THF are added with stirring. After 15 minutes, 5 g of ethyl 4-(4-oxocyclohexyl)benzoate (20.30 mmol, 1 eq.) are added dropwise. After stirring for 1 hour 30 minutes, 8.27 g of N-phenyltrifluoromethanesulfonimide dissolved in 50 mL of THF are added dropwise. The cooling bath is removed and stirring is continued for 4 hours. The reaction medium is diluted with water and extracted with diethyl ether. The organic phase is washed twice with water and once with brine. The organic phases are combined and evaporated. The residue is chromatographed on silica gel, eluting with a gradient of ethyl acetate in heptane ranging from 15% to 20%. 2.8 g of ethyl 4-(4-trifluoromethanesulfonyloxycyclohex-3-enyl)benzoate are obtained.

22.2 Synthesis of ethyl 4-(4-tert-butoxycarbonylcyclohex-3-enyl)benzoate 1 g of ethyl 4-(4-trifluoromethanesulfonyloxycyclohex-3-enyl)benzoate is placed in 10 mL of dioxane, which is placed in two microwave tubes. 349 mg of hexacarbonylmolybdenum (1.32 mmol, 0.5 eq.), 59 mg of palladium diacetate (0.26 mmol, 0.1 eq.), 147 mg of DPPF (0.26 mmol, 0.1 eq.), 646 mg of DMAP (5.29 mmol, 2 eq.), 1.06 mL of DIEA (6.08 mmol, 2.3 eq.) and 2.53 mL of tert-butanol (26.43 mmol, 10 eq.), which are placed in two tubes, are successively added. The tubes are sealed and heated by microwave at 120° C. for 10 minutes. The reaction medium is diluted with dichloromethane and washed with aqueous 1N HCl solution. The organic phases are dried over sodium sulfate, filtered and evaporated. The residue is chromatographed on silica gel, eluting with a gradient of ethyl acetate in heptane ranging from 15% to 20%. 0.66 g of ethyl 4-(4-tert-butoxycarbonylcyclohex-3-enyl)-benzoate is obtained.

22.3 Synthesis of ethyl 4-(4-tert-butoxycarbonylcyclohexyl)benzoate

This compound is obtained according to Preparation 13.1 with a heating temperature of 40° C. 0.4 g of ethyl 4-(4-tert-butoxycarbonylcyclohexyl)benzoate is isolated starting with ethyl 4-(4-tert-butoxycarbonylcyclohex-3-enyl)benzoate.

22.4 Synthesis of 4-(4-tert-butoxycarbonylcyclohexyl)benzoic acid 400 mg of ethyl 4-(4-tert-butoxycarbonylcyclohexyl)benzoate (1.2 mmol, 1 eq) are placed in 6 mL of a 2/1 mixture of tetrahydrofuran and methanol. The reaction medium is cooled using an ice bath, and 202 mg of lithium hydroxide monohydrate (4.81 mmol, 4 eq.) dissolved in 2 mL are added and stirring is continued for 18 hours. The reaction medium is evaporated and acidified with aqueous 6% sulfur dioxide solution. After stirring for 1 hour, the solid obtained is filtered off by suction, and washed successively with water, ethanol and ethyl acetate. The residue is chromatographed on silica gel, eluting with a gradient of methanol in dichloromethane ranging from 3% to 5%. 125 mg of 4-(4-tert-butoxycarbonylcyclohexyl)benzoic acid are obtained.

22.5 Synthesis of tert-butyl 4-[4-(5-benzyl[1.3.4] thiadiazol-2-ylcarbamoyl)phenyl]cyclohexanecarboxylate This compound is obtained according to Preparation 11.5. 85 mg of tert-butyl 4-[4-(5-benzyl[1.3.4]thiadiazol-2-ylcarbamoyl)phenyl]cyclohexanecarboxylate are obtained from 4-(4-tert-butoxycarbonylcyclohexyl)benzoic acid and 5-benzyl-1,3,4-thiadiazol-2-amine.

M+H$^+$=478.

22.6 Synthesis of 4-[4-(5-benzyl[1.3.4]thiadiazol-2-ylcarbamoyl)phenyl]cyclohexanecarboxylic acid 85 mg of tert-butyl 4-[4-(5-benzyl[1.3.4]thiadiazol-2-ylcarbamoyl)phenyl]cyclohexanecarboxylate (0.18 mmol, 1 eq.) are placed in 1 mL of dichloromethane. 1 mL of trifluoroacetic acid (13.46 mmol, 76 eq.) is added and the reaction medium is stirred for 3 hours at room temperature. The solvents are evaporated off and the residue is taken up in ethyl acetate and ethanol to give, after filtration, 30 mg of 4-[4-(5-benzyl[1.3.4]-thiadiazol-2-ylcarbamoyl)phenyl]cyclohexanecarboxylic acid.

M+H$^+$=422.

$^1$H NMR (400 MHz, DMSO-d6) δ ppm 13.01 to 11.86 (m, 2H), 8.02 (m, 2H), 7.46 to 7.25 (m, 7H), 4.39 (s, 2H), 2.72 to 2.56 (m, 2H), 2.39 to 1.95 (m, 3H), 1.91 to 1.40 (m, 5H).

EXAMPLE 23

(4-{4-[5-(3-hydroxy-3-phenylpropyl)[1.3.4]thiadiazol-2-ylcarbamoyl]-phenyl}cyclohexyl)acetic acid (Compound 84 of Table V)

23.1 Synthesis of tert-butyl trans-(4-{4-[5-(3-hydroxy-3-phenylpropyl)[1.3.4]thiadiazol-2-ylcarbamoyl] phenyl}cyclohexyl)acetate 0.159 g of tert-butyl trans-(4-{4-[5-(3-oxo-3-phenylpropyl)[1.3.4]thiadiazol-2-ylcarbamoyl]phenyl}cyclohexyl)acetate (0.3 mmol, 1 eq.) is placed in 5 mL of methanol with stirring. The reaction medium is cooled on an ice bath and 0.012 g of sodium borohydride (0.33 mmol, 1.1 eq.) is added. 3 mL of DMF are added. After stirring for 16 hours, the reaction medium is cooled on an ice bath and 0.023 g of sodium borohydride (0.6 mmol, 2 eq.) and 3 mL of DMF are added. After stirring for 2 hours, the reaction medium is poured into water and extracted twice with ethyl acetate. The organic phase is washed three times with water, dried over magnesium sulfate and evaporated to give 0.146 g of tert-butyl trans-(4-{4-[5-(3-hydroxy-3-phenylpropyl)-[1.3.4]thiadiazol-2-ylcarbamoyl]phenyl}cyclohexyl)acetate,
M+H+=536.

23.2 Synthesis of trans-(4-{4-[5-(3-hydroxy-3-phenylpropyl)[1.3.4]thiadiazol-2-ylcarbamoyl]phenyl}cyclohexyl)acetic acid 0.146 g of tert-butyl trans-(4-{4-[5-(3-hydroxy-3-phenylpropyl)[1.3.4]thiadiazol-2-ylcarbamoyl]phenyl}cyclohexyl)acetate (0.27 mmol, 1 eq.) is placed in 2 mL of dichloromethane with stirring. 0.4 mL of TFA (5.45 mmol, 20 eq.) is added. After stirring for 4 hours, the reaction medium is evaporated and the residue is chromatographed on silica gel, eluting with a gradient of methanol in dichloromethane ranging from 1% to 10%. The fractions of interest are concentrated, and triturated with ethyl acetate and methanol. 0.020 g of trans-(4-{4-[5-(3-hydroxy-3-phenylpropyl)[1.3.4]thiadiazol-2-ylcarbamoyl]phenyl}cyclohexyl)acetic acid is obtained.
M+H+=480.
$^1$H NMR (400 MHz, DMSO-d6) δ ppm 12.97 to 11.74 (m, 2H), 8.04 (m, 2H), 7.45 to 7.32 (m, 6H), 7.25 (m, 1H), 5.39 (d, J=4.5 Hz, 1H), 4.66 (m, 1H), 3.06 (m, 2H), 2.58 (tt, J=12 Hz and 3 Hz, 1H), 2.17 (d, J=7 Hz, 2H), 2.06 (m, 2H), 1.90 to 1.70 (m, 5H), 1.52 (m, 2H), 1.15 (m, 2H).

EXAMPLE 24 trans-{4-[4-(5-phenylmethanesulfinylmethyl[1.3.4]thiadiazol-2-ylcarbamoyl)phenyl]cyclohexyl}acetic acid (Compound 95 of Table V)

24.1 Synthesis of tert-butyl trans-{4-[4-(5-phenylmethanesulfinylmethyl[1.3.4]thiadiazol-2-ylcarbamoyl)phenyl]cyclohexyl}acetate 0.1 g of tert-butyl trans-{4-[4-(5-benzylsulfanylmethyl[1.3.4]thiadiazol-2-ylcarbamoyl)-phenyl]cyclohexyl}acetate (0.11 mmol, 1 eq.) is placed in 10 mL of dichloromethane with stirring. 0.027 g of 70% meta-chloroperbenzoic acid (0.11 mmol, 1 eq.) is added. After 2 hours, 0.01 g of 70% meta-chloroperbenzoic acid (0.41 mmol, 0.37 eq.) is added. After 16 hours, the reaction medium is diluted with dichloromethane and washed with saturated aqueous sodium hydrogen carbonate solution. The organic phase is dried and evaporated. The residue is triturated in ethyl acetate to give 0.072 g of tert-butyl trans-{4-[4-(5-phenylmethanesulfinylmethyl[1.3.4]thiadiazol-2-ylcarbamoyl)-phenyl]cyclohexyl}acetate.
M+H+=554.

24.2 Synthesis of trans-{4-[4-(5-phenylmethanesulfinylmethyl[1.3.4]thiadiazol-2-ylcarbamoyl)phenyl]cyclohexyl}acetic acid 0.072 g of tert-butyl trans-{4-[4-(5-phenylmethanesulfinylmethyl[1.3.4]thiadiazol-2-ylcarbamoyl)phenyl]cyclohexyl}acetate (0.13 mmol, 1 eq.) is placed in 2 mL of dichloromethane with stirring. 1 mL of TFA (13.46 mmol, 104 eq.) is added. After 1 hour, the reaction medium is evaporated and the residue is triturated in ethanol to give 0.055 g of trans-{4-[4-(5-phenylmethanesulfinylmethyl[1.3.4]thiadiazol-2-ylcarbamoyl)phenyl]cyclohexyl}acetic acid.
M+H+=498.

$^1$H NMR (400 MHz, DMSO-d6) δ ppm 12.99 (m, 1H), 12.02 (m, 1H), 8.07 (m, 2H), 7.49 to 7.33 (m, 7H), 4.70 (m, 1H), 4.45 (m, 1H), 4.29 (m, 1H), 4.02 (m, 1H), 2.59 (m, 1H), 2.17 (d, J=6.8 Hz, 2H), 1.90 to 1.71 (m, 5H), 1.53 (m, 2H), 1.15 (m, 2H).

EXAMPLE 25 cis-4-[4-(5-cyclopentylamino[1.3.4]thiadiazol-2-ylcarbamoyl)-phenoxy]cyclohexanecarboxylic acid (Compound 101 of Table V)

25.1 Synthesis of methyl cis-4-[4-(5-cyclopentylamino[1.3.4]thiadiazol-2-ylcarbamoyl)-phenoxy]cyclohexanecarboxylate 0.350 g of cis-4-(4-methoxycarbonylcyclohexyloxy)benzoic acid (1.26 mmol, 1 eq.) is placed in 13 mL of dichloromethane with stirring, at room temperature, under a nitrogen atmosphere. 0.16 mL of oxalyl chloride (1.89 mmol, 1.5 eq.) and 2 drops of dimethylformamide are successively added. The reaction medium is stirred for 1.5 hours and concentrated under vacuum. The methyl cis-4-(4-chlorocarbonylphenoxy)cyclohexanecarboxylate formed is dissolved in 13 mL of acetonitrile and placed under nitrogen. 0.255 g N-cyclopentyl[1.3.4]thiadiazole-2,5-diamine (1.39 mmol, 1.1 eq.) and 0.12 mL of pyridine (1.51 mmol, 1.2 eq.) are successively added. After 3 days, the medium is filtered and rinsed with acetonitrile to give 0.33 g of methyl cis-4-[4-(5-cyclopentylamino[1.3.4]thiadiazol-2-ylcarbamoyl)phenoxy]cyclohexanecarboxylate.
M+H+=445.

25.2 Synthesis of cis-4-[4-(5-cyclopentylamino[1.3.4]thiadiazol-2-ylcarbamoyl)-phenoxy]cyclohexanecarboxylic acid 0.310 g of methyl cis-4-[4-(5-cyclopentylamino[1.3.4]thiadiazol-2-ylcarbamoyl)-phenoxy]cyclohexanecarboxylate (0.70 mmol, 1 eq.) is placed in 8 mL of a tetrahydrofuran/methanol mixture. 112 mg of sodium hydroxide (2.79 mmol, 4 eq.) dissolved in 6 mL of water are added and stirring is continued for 18 hours. The reaction medium is evaporated. The residue is taken up in water and washed twice with diethyl ether. The aqueous phase is partially concentrated and acidified with an aqueous 6% sulfur dioxide solution. The aqueous phase is partially concentrated, drained and washed successively with water and with diethyl ether. 0.19 mg of cis-4-[4-(5-cyclopentylamino[1.3.4]thiadiazol-2-ylcarbamoyl)phenoxy]cyclohexanecarboxylic acid is obtained.
M+H+=431.
$^1$H NMR (400 MHz, DMSO-d6) δ ppm 12.15 (m, 2H), 8.04 (m, 2H), 7.31 (m, 1H), 7.06 (m, 2H), 4.68 (m, 1H), 3.98 (m, 1H), 2.40 (m, 1H), 2.00 to 1.45 (m, 16H).

EXAMPLE 26

N-(5-benzyl[1.3.4]thiadiazol-2-yl)-4-{4-[(2.3-dihydroxypropylcarbamoyl)methyl]cyclohexyl}benzamide (Compound 88 of Table V)

0.25 g of trans-(4-{4-benzyl[1.3.4]thiadiazol-2-ylcarbamoyl}phenyl}cyclohexyl)acetic acid (0.57 mmol, 1 eq.) is placed in 4 mL of DMF at room temperature with stirring. 0.294 g of bromotris-pyrrolidinophosphonium hexafluorophosphonate (0.63 mmol, 1.1 eq.), 0.20 mL of diisopropylethylamine (1.15 mmol, 2 eq.) and 0.09 mL of 3-amino-1,2-propanediol (1.15 mmol, 2 eq.) are added. The reaction mixture is stirred for 18 hours at room temperature, diluted in ethyl acetate and washed with water. The aqueous phase is extracted with ethyl acetate. The organic phases are concentrated and the residue is chromatographed on silica gel, eluting with a gradient of methanol in dichloromethane ranging from 1% to 10%. The fractions of interest are evaporated and the residue is triturated with ethanol to give 0.171 g of N-(5-benzyl[1.3.4]thiadiazol-2-yl)-4-{4-[(2.3-dihydroxypropylcarbamoyl)methyl]cyclohexyl}benzamide.

M+H$^+$=509.

$^1$H NMR (400 MHz, DMSO-d6) δ ppm 12.82 (m, 2H), 8.02 (m, 2H), 7.79 (t, J=5.8 Hz, 1H), 7.41 (m, 2H), 7.37 (m, 4H), 7.30 (m, 1H), 4.70 (d, J=4.8 Hz, 1H), 4.50 (t, J=5.8 Hz, 1H), 4.38 (s, 2H), 3.49 (m, 1H), 3.30 (m, 1H), 3.21 (m, 1H), 3.01 (m, 1H), 2.56 (m, 1H), 2.05 (d, J=6.6 Hz, 2H), 1.86 to 1.70 m, 5H), 1.49 (m, 2H), 1.11 (m, 2H).

EXAMPLE 27 cis-4-{4-[5-(3,5-difluorobenzyl)[1.3.4]thiadiazol-2-ylcarbamoyl]-phenoxy}cyclohexanecarboxylic acid
(Compound 94 of Table V)

27.1 Synthesis of [(3,5-difluorophenyl)acetyl]hydrazinecarbothioamide 2.5 g of 3,5-difluorophenylacetic acid (14.52 mmol, 1 eq.) are placed in 70 mL of dichloromethane with stirring. 1.46 g of thiosemicarbazide (15.98 mmol, 1.1 eq.), 2.22 g of hydroxybenzotriazole (14.52 mmol, 1 eq.) and 2.78 g of 1-ethyl-3-(3-dimethylaminopropyl)carbodiimide hydrochloride (14.52 mmol, 1 eq.) are successively added with continued stirring at room temperature. After 18 hours at room temperature, the dichloromethane is evaporated off. The residue is taken up in ethyl acetate and 1N hydrochloric acid. The precipitate is filtered off and dried to give 1.67 g of [(3,5-difluorophenyl)acetyl]hydrazinecarbothioamide.

M+H$^+$=246.

27.2 Synthesis of 5-(3,5-difluorobenzyl)[1.3.4]thiadiazol-2-ylamine 20 mL of sulfuric acid are placed in a round-bottomed flask, which is cooled to 0° C. 1.67 g of 5-(3,5-difluorobenzyl)[1.3.4]thiadiazol-2-ylamine (1.67 mmol) are added portionwise with stirring. After stirring for 3 hours, ice is added and the mixture is returned to basic pH with sodium hydroxide. The precipitate is filtered off, washed with water and dried. 1.6 g of 5-(3,5-difluorobenzyl)[1.3.4]thiadiazol-2-ylamine are obtained.

M+H$^+$=228.

27.3 Synthesis of methyl cis-4-{4-[5-(3,5-difluorobenzyl)[1.3.4]thiadiazol-2-ylcarbamoyl]-phenoxy}cyclohexanecarboxylate 2.2 g of cis-4-(4-methoxycarbonylcyclohexyloxy)benzoic acid (7.91 mmol, 1 eq.) are placed in 30 mL of dimethylformamide at room temperature. 1.98 g of 5-(3,5-difluorobenzyl)[1.3.4]thiadiazol-2-ylamine (8.70 mmol, 1.1 eq.), 4.42 g of bromotris-pyrrolidinophosphonium hexafluorophosphonate (9.49 mmol, 1.2 eq.) and 2.76 mL of diisopropylethylamine (15.81 mmol, 2 eq.) are successively added. The reaction mixture is stirred for 6 days at room temperature, poured into water and extracted with ethyl acetate. The organic phase is washed three times with water and once with brine. The organic phase is concentrated and the residue is chromatographed on silica gel, eluting with a gradient of ethyl acetate in heptane ranging from 7% to 30%. 1.5 g of methyl cis-4-{4-[5-(3,5-difluorobenzyl)[1.3.4]thiadiazol-2-ylcarbamoyl]phenoxy}cyclohexanecarboxylate are obtained.

M+H$^+$=488.

27.4 Synthesis of cis-4-{4-[5-(3,5-difluorobenzyl)[1.3.4]thiadiazol-2-ylcarbamoyl]-phenoxy}cyclohexanecarboxylic acid 1.5 g of methyl 4-{4-[5-(3,5-difluorobenzyl)[1.3.4]thiadiazol-2-ylcarbamoyl]phenoxy}-cyclohexanecarboxylate (3.08 mmol, 1 eq.) are dissolved in 20 mL of a 1/1 mixture of THF/methanol. 0.258 g of lithium hydroxide monohydrate (6.15 mmol; 2 eq.) is added with stirring. After 16 hours at room temperature, the reaction medium is evaporated, diluted with water, and aqueous 6% sulfur dioxide solution is added. The precipitate is filtered off and washed with water. The residue is then triturated and filtered in ethyl acetate and ethanol. 1.14 g of cis-4-{4-[5-(3,5-difluorobenzyl)[1.3.4]thiadiazol-2-ylcarbamoyl]phenoxy}cyclohexanecarboxylic acid are obtained.

M+H$^+$=472.

$^1$H NMR (400 MHz, DMSO-d6) δ ppm 12.44 (m, 2H), 8.12 (m, 2H), 7.24 to 7.07 (m, 5H), 4.72 (m, 1H), 4.45 (s, 2H), 2.45 (m, 1H), 1.93 to 1.67 (m, 8H).

Tables I to V that follow illustrate the chemical structures and physical properties of a few compounds according to the invention, corresponding to formula (I).

Table I illustrates compounds of formula (I) according to the invention for which W is a carbon atom, D is a bond, p=0, R is a hydrogen atom, U is an oxygen atom and thus R5 is absent, Z4 is a hydrogen atom and Z2 is absent; these compounds are referred to hereinbelow as compounds of formula (A).

Table II illustrates compounds of formula (I) according to the invention for which D is an oxygen atom, Z1. Z2 and Z3 are absent, Z4 represents a hydrogen atom, X represents a sulfur atom and p=0; these compounds are referred to hereinbelow as compounds of formula (B).

Table III illustrates compounds of formula (I) according to the invention for which Y represents Ph, Z4, R, R1 and R2 represent hydrogen atoms, n=1, Z1, Z2 and Z3 are absent. X represents a sulfur atom, p=0 and W represents a carbon atom; these compounds are referred to hereinbelow as compounds of formula (C).

Table IV illustrates compounds of formula (I) according to the invention for which R1. R2 and Z4 each represents a hydrogen atom, n=1 and Z1 is absent, W represents a carbon atom. D represents a bond and p=0; these compounds are referred to hereinbelow as compounds of formula (D).

Table V illustrates compounds of formula (I).

In these tables;
  the compounds of Table I are mainly in trans form or exclusively in trans form, unless otherwise indicated;
  in Tables II, III, IV and V, the cis/trans stereochemistry of the compounds is indicated;
  "-" in the "Z1, Z3" column or the "R1" column or the "R2" column indicates that the corresponding group is absent;
  "*" indicates the bonding atom,
  Me, Et, n-Pr, i-Pr, t-Bu and i-Bu represents, respectively, methyl, ethyl, n-propyl, isopropyl, tert-butyl and isobutyl group is,
  "m.p." represents the melting point of the compound, expressed in degrees Celsius (° C.). <<then dec.>> means <<then the composition of the compound>>
  "MH$^+$" represents the mass M+H of the compound, obtained by LC-MS (abbreviation for Liquid Chromatography-Mass Spectroscopy).
  "¤" in the "MH+" or "m.p." columns indicates that the measurement was not taken.

TABLE I (A)

| No. | n | R1 | R2 | X | Y | Z1/Z3 | NH+ | m.p. |
|---|---|---|---|---|---|---|---|---|
| 1 | 1 | H | H | S | phenyl | —/CH₂ | 436 | 279° C. |
| 2 | 1 | H | H | S | 4-methylphenyl | —/CH₂ | 450 | >250° C. |
| 3 | 1 | H | H | S | 2-fluorophenyl | —/CH₂ | 454 | 271 |
| 4 | 1 | H | H | S | 3-fluorophenyl | —/CH₂ | 454 | 277 |
| 5 | 1 | H | H | S | 4-fluorophenyl | —/CH₂ | 454 | >250° C. |
| 6 | 1 | H | H | S | 3,4,5-trifluorophenyl | —/CH₂ | 490 | 242 |
| 7 | 1 | cyclopropyl | | S | phenyl | —/CH₂ | 462 | >250° C. |
| 8 | 1 | cyclopropyl | | S | 4-fluorophenyl | —/CH₂ | 480 | >250° C. |
| 9 | 1 | cyclobutyl | | S | 4-fluorophenyl | —/CH₂ | 494 | 275 |

TABLE I-continued
(A)
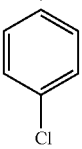
| No. | n | R1 | R2 | X | Y | Z1/Z3 | NH+ | m.p. |
|---|---|---|---|---|---|---|---|---|
| 10 | 1 | H | H | S | 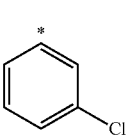 | —/CH$_2$ | 470 | >250° C. |
| 11 | 1 | H | H | S | 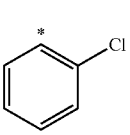 | —/CH$_2$ | 470 | 255-260 |
| 12 | 1 | H | H | S | 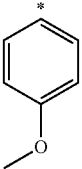 | —/CH$_2$ | 470 | 245-250 |
| 13 | 1 | H | H | S | 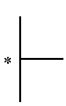 | —/CH$_2$ | 466 | 254 |
| 14 | 0 | — | — | S | 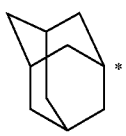 | —/CH$_2$ | 402 | 298 |
| 15 | 0 | — | — | S | 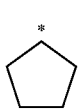 | —/CH$_2$ | 480 | 320 |
| 16 | 0 | — | — | S | 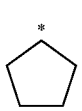 | —/CH$_2$ | 414 | 274 |
| 17 | 1 | — | — | S | 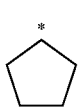 | —/CH$_2$ | 428 | 268 |
| 18 | 2 | H | H | S | 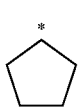 | —/CH$_2$ | 442 | 235 then dec. |
| 19 | 0 | — | — | S | —iBu | —/CH$_2$ | 402 | 263 |

TABLE I-continued
(A)
| No. | n | R1 | R2 | X | Y | Z1/Z3 | NH+ | m.p. |
|---|---|---|---|---|---|---|---|---|
| 20 | 2 | H | H | S | 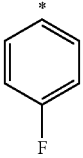 | —/CH$_2$ | 450 | 270 |
| 21 | 2 | H | H | S | 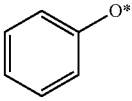 | —/CH$_2$ | 468 | 270 |
| 22 | 1 | H | H | S | 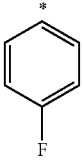 | —/CH$_2$ | 452 | 261 |
| 23 | 3 | H | H | S | 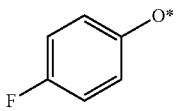 | —/CH$_2$ | 482 | 229 |
| 24 | 1 | H | H | S |  | —/CH$_2$ | 470 | 275 |
| 25 | 0 | — | — | S | 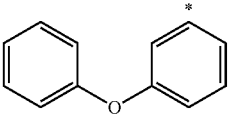 | —/CH$_2$ | 422 | 240 then dec. |
| 26 | 0 | — | — | S |  | —/CH$_2$ | 514 | 240 then dec. |
| 27 | 0 | — | — | S | 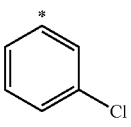 | —/CH$_2$ | 423 | >250 |
| 28 | 0 | — | — | S |  | —/CH$_2$ | 456 | >250 |

TABLE I-continued
(A)
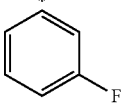
| No. | n | R1 | R2 | X | Y | Z1/Z3 | NH+ | m.p. |
|---|---|---|---|---|---|---|---|---|
| 29 | 0 | — | — | S | 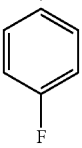 | —/CH$_2$ | 440 | >250 |
| 30 | 0 | — | — | S | 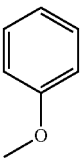 | —/CH$_2$ | 440 | >250 |
| 31 | 0 | — | — | S | 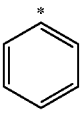 | —/CH$_2$ | 452 | >250 |
| 32 | 1 | H | H | O | 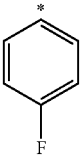 | —/CH$_2$ | 420 | ¤ |
| 33 | 1 | H | H | O | 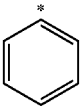 | —/CH$_2$ | 438 | 215 |
| 34 cis | 1 | H | H | S | 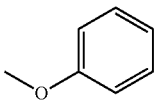 | —/CH$_2$ | 436 | 277 |
| 35 | 0 | — | — | S | 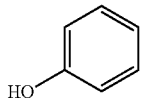 | —/CH$_2$ | 452 | 264-282 |
| 36 | 0 | — | — | S | 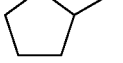 | —/CH$_2$ | 438 | 286 then dec. |
| 37 | 1 | H | H | S |  | —/CH$_2$ | 444 | >250 |

TABLE I-continued
(A)
| No. | n | R1 | R2 | X | Y | Z1/Z3 | NH+ | m.p. |
|---|---|---|---|---|---|---|---|---|
| 38 | 2 | H | H | S |  | —/CH$_2$ | 444 | 249 |
| 39 | 2 | H | H | S | 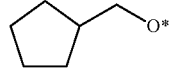 | —/CH$_2$ | 456 | >260 |
| 40 | 1 | H | H | S |  | CH$_2$/CH$_2$ | 458 | 241 |
| 41 | 1 | H | H | S | 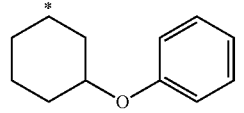 | S/CH$_2$ | 468 | ¤ |
| 44 | 1 | H | H | S | 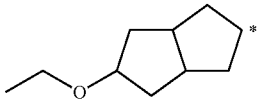 | —/CH$_2$ | 520 | 245 |
| 45 | 1 | H | H | S | 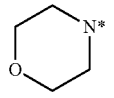 | —/CH$_2$ | 511 | 201 then dec. |
| 47 | 0 | — | — | S | Br | —/CH$_2$ | 424 | ¤ |
| 48 | 2 | H | H | S | 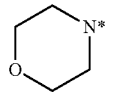 | —/CH$_2$ | 459 | 213 |
| 49 | 0 | — | — | S | 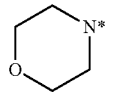 | —/CH$_2$ | 431 | >250 |
| 50 | 0 | — | — | S | COOH | —/CH$_2$ | ¤ | 275-280 |
| 51 | 1 | H | H | S | 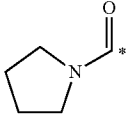 | —/CH$_2$ | 457 | >260 |

TABLE II
(B)
| No. | n | R | R1 | R2 | W | Y | MH+ | m.p. |
|---|---|---|---|---|---|---|---|---|
| 52 cis | 1 | H | H | H | C |  | 438 | 266 |
| 53 trans | 1 | H | H | H | C |  | 438 | 270 |
| 54 trans | 0 | H | — | — | C |  | 424 | 306 |
| 55 cis | 1 | F | H | H | C |  | 456 | 290 |
| 56 cis | 1 | Cl | H | H | C |  | 472 | 263 |
| 57 cis | 2 | H | H | H | C |  | 444 | 270 |
| 58 cis | 0 | H | — | — | C | 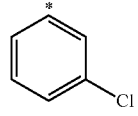 | 424 | 291 |
| 59 cis | 0 | H | — | — | C | 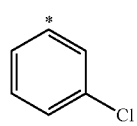 | 458 | 296 |
| 60 cis | 0 | H | — | — | C |  | 476 | 288 |
| 61 cis | 0 | H | — | — | C | H | 348 | 277 |
| 62 cis | 1 | H | H | H | N | * | 439 | 252-257 |

TABLE II-continued (B)

[Structure: R1R2Y-(CH)n-[1,3,4-thiadiazole]-NH-C(=O)-[benzene with W-R]-O-cyclohexyl-COOH]

| No. | n | R | R1 | R2 | W | Y | MH+ | m.p. |
|---|---|---|---|---|---|---|---|---|
| 63 cis | 1 | H | H | H | N | *-C6H4-Cl | 473 | 256 |
| 64 cis | 2 | H | H | H | N | *-C6H5 | 453 | 255-260 |
| 65 cis | 0 | H | — | — | N | *-C6H5 | 425 | >265 |
| 66 cis | 0 | H | — | — | N | *-C6H4-Cl | 459 | 277-280 |
| 67 cis | 1 | H | H | H | C | cyclopentyl-O* | 445 | 272 |

TABLE III (C)

[Structure: benzyl-[1,3,4-thiadiazole]-NH-C(=O)-[benzene]-D-cyclohexyl-COOH]

| No. | D | MH+ | m.p. |
|---|---|---|---|
| 68 cis | NH | 437 | 248 |
| 69 trans | NH | 437 | 265 |
| 70 trans | bond | 422 | 247 then dec. |

TABLE IV
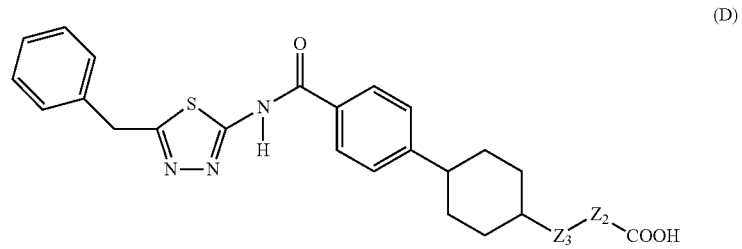
(D)
| No. | Z2 | Z3 | Unit formed between Z2 and Z3 | MH+ | m.p. |
|---|---|---|---|---|---|
| 71 | —CH= | =CH— | double bond | 448 | >250 |
| 72 | —CH< | —CH< | △ | 462 | >250 |
| 73 trans | —CH2— | —CH2— | single bond | 450 | 275-280 |
TABLE V
| No. | Molecules (I) | MH+ | m.p. |
|---|---|---|---|
| 74 | | 444 | >260 |
| 75 | | 476 | 258 |
| 76 | | 479 | 291 |
| 78 | | 472 | 294 |
| 79 | | 458 | >250 |

TABLE V-continued

| No. | Molecules (I) | MH+ | m.p. |
|---|---|---|---|
| 80 | | 460 | 220 then dec. |
| 81 | | 452 | 230-250 |
| 82 | | 462 | 217-223 |
| 83 | | 478 | 240-268 |
| 84 | | 480 | 239-242 |
| 85 | | 482 | >250 |
| 86 | | 507 | 260 |
| 87 | | 435 | 280 |

| No. | Molecules (I) | MH+ | m.p. |
|---|---|---|---|
| 88 | | 509 | 224 |
| 89 | | 548 | 227 |
| 90 | | 506 | 256 |
| 91 | | 493 | 268 |
| 92 | | 429 | 335 |
| 93 | | 535 | 281 |
| 94 | | 474 | 235-237 |
| 95 | | 498 | 241 |

TABLE V-continued

| No. | Molecules (I) | MH+ | m.p. |
|---|---|---|---|
| 96 | | 482 | 234 |
| 97 | | 476 | 247 |
| 98 | | 447 | ¤ |
| 101 | | 431 | 294 |
| 102 | | 480 | 220-260 |
| 42 | | 434 | 255 |
| 43 | | 448 | 255 |
| 46 | | 452 | 250-255 |

The compounds according to the invention underwent pharmacological trials for determining their inhibitory effect on triglyceride biosynthesis.

These trials consisted in measuring the in vitro inhibitory activity of the compounds of the invention on a cell test.

Chang liver cells at 80% confluence are detached with trypsin-EDTA, 4 ml per 175 cm$^2$ flask. After centrifugation at 1300×g for 5 minutes, the cell pellet is washed once with PBS and then resuspended in whole medium. The number of cells and their viability are determined on Mallassez cells via the exclusion method with trypan blue.

150 000 cells are inoculated per well into a 24-well plate for a minimum of 3 hours in DMEM medium 4.5 g/l of glucose supplemented with 10% FCS and with antibiotics, and are maintained at 37° C. in an incubator with $CO_2$ (5%).

After 3 hours, the cells have adhered, the medium is removed and replaced overnight with DMEM medium 4.5 g/l of glucose with 2% of BSA/oleate.

After culturing for 18 hours without serum, the test compounds are incubated for 30 minutes (1.3, 10, 30, 100, 300 and 1000 nM) with the cells, followed by addition of [$^{14}$C] glycerol (0.4 µCi/ml/well) for an incorporation time of 6 hours.

The supernatant is drawn off and the cells are recovered by treatment with trypsin-EDTA, 100 µl/well, for 5 minutes at 37° C. This cell suspension is then recovered in an Eppendorf tube and is washed with twice 500 µl of PBS. The centrifugation at 1300×g for 5 minutes allows recovery of the cell pellets, which may be frozen at −20° C. In order to extract the lipids from the cell pellet, 400 µl of a methanol/dichloromethane/trifluoroacetic acid mixture (50/50/0.1%) is used to resuspend the cells. Next, the cell membranes are destroyed by sonication on a water bath, for 30 minutes. The samples are filtered through a 0.45 µm filtered and then injected onto a C18 HPLC column of 4.6×75 mm, 3 µm with a mobile phase of 5% ($H_2O$+0.1% TFA), 70% methanol, 25% dichloromethane, with a flow rate of 1.5 ml/minute. The radioactivity is measured using a Flo One C625TR machine (Perkin-Elmer).

The inhibitory activity on triglyceride biosynthesis is given by the concentration that inhibits 50% of the activity.

The activities of the compounds according to the invention are generally between 0.01 µM and 10 µM and more particularly between 0.01 and 1 µM.

For example, the activities of compounds 1; 4; 23; 25; 37; 40; 63 and 68 are, respectively, 0.029; 0.046; 0.181; 0.590; 0.018; 0.051; 0.085 and 0.271 µM.

It is thus seen that the compounds according to the invention have inhibitory activity on triglyceride biosynthesis.

The compounds according to the invention may thus be used for the preparation of medicaments, in particular medicaments for inhibiting triglyceride biosynthesis.

Thus, according to another of its aspects, a subject of the invention is medicaments comprising a compound of formula (I), or an addition salt thereof with a pharmaceutically acceptable acid or base of the compound of formula (I).

These medicaments find their use in therapy, especially in the treatment and/or prevention of obesity, dyslipidaemia, impaired fasting glucose conditions, metabolic acidosis, ketosis, hepatic steatosis, insulin resistance, type 2 diabetes and complications arising from this pathology, lipotoxicity, the accumulation and an excess of triacylglycerides in adipose tissue (WAT), metabolic syndrome, coronary diseases, hypertension, skin diseases. Alzheimer's disease, immunomodulatory diseases, infection with HIV, irritable bowel syndrome and certain cancers, and advantageously for the preparation of a medicament for treating or preventing obesity, dyslipidaemia, fasted glucose impairment conditions, metabolic acidosis, ketosis, hepatic steatosis, insulin resistance, type 2 diabetes and complications arising from this pathology, lipotoxicity, the accumulation and an excess of triacylglycerides in adipose tissue (WAT), and metabolic syndrome.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt of the said compound, and also at least one pharmaceutically acceptable excipient. The said excipients are chosen, according to the desired pharmaceutical form and mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt thereof, may be administered in unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages do not depart from the scope of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration to patient of an effective dose of a compound according to the invention, or a pharmaceutically acceptable salt thereof.

The invention claimed is:
1. A compound corresponding to formula (I)

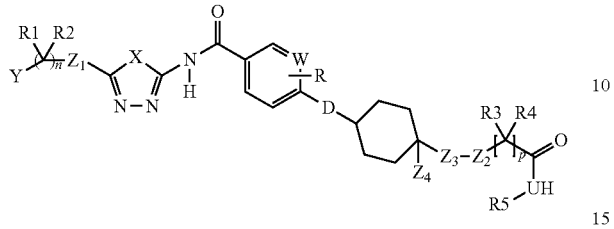

wherein
U represents an oxygen atom or a nitrogen atom, wherein if U represents an oxygen atom, then R5 is absent;
n is equal to 0, 1, 2 or 3;
p is equal to 0, 1 or 2;
D represents an oxygen atom, —NH— or a bond;
W represents a carbon or nitrogen atom;
X represents a heteroatom selected from the group consisting of an oxygen atom and a sulfur atom;
R1, R2, R3 and R4 represent, independently of each other, a hydrogen atom,
—(C1-C6)alkyl, or alternatively,
(i) R1 and R2 optionally form, together with the carbon atom to which they are attached, —(C3-C10)cycloalkyl- and/or (ii) R3 and R4 optionally form, together with the carbon atom to which they are attached, —(C3-C10)cycloalkyl-;
Y represents a hydrogen atom, —(C1-C6)alkyl, (C3-C10)cycloalkyl-, (C3-C10)cycloalkyloxy-, (C3-C10)cycloalkyl-(C1-C6)alkyloxy-, heterocycloalkyl-(C1-C6)alkyloxy-, —COOR1, aryl, arylalkyl, heteroaryl, heterocycloalkyl, aryloxy, —C(O)-heterocycloalkyl, —C(O)aryl, —CH(OH)aryl or —NH-cycloalkyl, wherein said Y is optionally substituted with one or more substituents selected from the group consisting of a halogen atom, a hydroxyl, (C1-C6)alkyl, (C1-C6)alkoxy, heterocycloalkyl and aryloxy;
R represents a hydrogen or halogen atom;
$Z_1$ is absent or represents a sulfur atom, —NH—, —NHC(O)—, —S(O)—CH$_2$—, —SCH$_2$—, methylene or ethylene;
$Z_2$ is absent or represents a methylene,

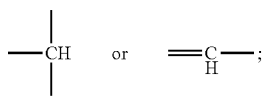

$Z_3$ is absent or represents an oxygen atom, methylene,

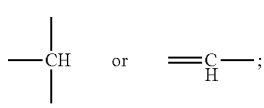

wherein $Z_2$ represents

only when $Z_3$ represents

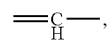

and $Z_3$ represents

only when $Z_2$ represents

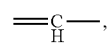

$Z_2$ and $Z_3$ thus forming a double bond;
$Z_4$ is
a hydrogen atom,
a carbon atom optionally forming with $Z_3$ —(C3-C10)cycloalkyl- when $Z_3$ is

or
absent, and $Z_3$ is

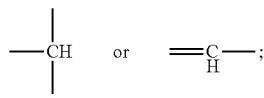

forming a double bond with the adjacent cyclohexyl carbon and;
R5 represents a hydrogen atom or alkyl optionally substituted with at least one hydroxyl, heterocycloalkyl(C1-C6)alkyl, amine or alkyloxy,
in the form of an acid or base or of an addition salt with an acid or with a base.

2. The compound according to claim 1, wherein n is equal to 1, 2 or 3.

3. The compound according to claim 1, corresponding to formula (I'):

(I')

4. The compound according to claim 1, corresponding to formula (I"):

(I")

5. The compound according to claim 1, Wherein D represents a bond.
6. The compound according to claim 1, wherein D represents an oxygen atom.
7. The compound according to claim 1, wherein p is equal to 0.
8. The compound according to claim 1, wherein:
   $Z_3$ and $Z_2$ each represents a methylene, or
   $Z_3$ represents a methylene and $Z_2$ is absent, or
   $Z_3$ and $Z_2$ are absent.
9. The compound according to claim 1, wherein:
   $Z_3$ and $Z_2$ together form cycloalkyl, or
   $Z_3$ and $Z_2$ together form a double bond.
10. The compound according to claim 1, wherein W represents a carbon atom.
11. The compound according to claim 1, wherein X represents a sulfur atom.
12. The compound according to claim 1, wherein said compound is:
    {4-[4-(5-benzyl[1,3,4]thiadiazol-2-ylcarbamoyl)phenyl]cyclohexyl}acetic acid,
    (4-{4-[5-(4-methylbenzyl)[1,3,4]thiadiazol-2-ylcarbamoyl]phenyl}cyclohexyl)acetic acid,
    (4-{4-[5-(2-fluorobenzyl)[1,3,4]thiadiazol-2-ylcarbamoyl]phenyl}cyclohexyl)acetic acid,
    (4-{4-[5-(3-fluorobenzyl)[1,3,4]thiadiazol-2-ylcarbamoyl]phenyl}cyclohexyl)acetic acid,
    (4-{4-[5-(4-fluorobenzyl)[1,3,4]thiadiazol-2-ylcarbamoyl]phenyl}cyclohexyl)acetic acid,
    (4-{4-[5-(2,4,5-trifluorobenzyl)[1,3,4]thiadiazol-2-ylcarbamoyl]phenyl}cyclohexyl)acetic acid,
    [4-(4-{5-[1-(phenyl)cyclopropyl][1,3,4]thiadiazol-2-ylcarbamoyl}phenyl)cyclohexyl]acetic acid,
    [4-(4-{5-[1-(4-fluorophenyl)cyclopropyl][1,3,4]thiadiazol-2-ylcarbamoyl}phenyl)cyclohexyl]acetic acid,
    [4-(4-{5-[1-(3-fluorophenyl)cyclobutyl][1,3,4]thiadiazol-2-ylcarbamoyl}phenyl)cyclohexyl]acetic acid,
    (4-{4-[5-(4-chlorobenzyl)[1,3,4]thiadiazol-2-ylcarbamoyl]phenyl}cyclohexyl)acetic acid,
    (4-{4-[5-(3-chlorobenzyl)[1,3,4]thiadiazol-2-ylcarbamoyl]phenyl}cyclohexyl)acetic acid,
    (4-{4-[5-(2-chlorobenzyl)[1,3,4]thiadiazol-2-ylcarbamoyl]phenyl}cyclohexyl)acetic acid,
    (4-{4-[5-(4-methoxybenzyl)[1,3,4]thiadiazol-2-ylcarbamoyl]phenyl}cyclohexyl)acetic acid,
    {4-[4-(5-tert-butyl[1,3,4]thiadiazol-2-ylcarbamoyl)phenyl]cyclohexyl}acetic acid,
    {4-[4-(5-adamantan-1-yl[1,3,4]thiadiazol-2-ylcarbamoyl)phenyl]cyclohexyl}acetic acid,
    {4-[4-(5-cyclopentyl[1,3,4]thiadiazol-2-ylcarbamoyl)phenyl]cyclohexyl}acetic acid,
    {4-[4-(5-cyclopentylmethyl[1,3,4]thiadiazol-2-ylcarbamoyl)phenyl]cyclohexyl}acetic acid,
    (4-{4-[5-(2-cyclopentylethyl)[1,3,4]thiadiazol-2-ylcarbamoyl]phenyl}cyclohexyl)acetic acid,
    {4-[4-(5-isobutyl[1,3,4]thiadiazol-2-ylcarbamoyl)phenyl]cyclohexyl}acetic acid,
    {4-[4-(5-phenethyl[1,3,4]thiadiazol-2-ylcarbamoyl)phenyl]cyclohexyl}acetic acid,
    [4-(4-{5-[2-(4-fluorophenyl)ethyl][1,3,4]thiadiazol-2-ylcarbamoyl}phenyl)cyclohexyl]acetic acid,
    {4-[4-(5-phenoxymethyl[1,3,4]thiadiazol-2-ylcarbamoyl)phenyl]cyclohexyl}acetic acid,
    [4-(4-{5-[3-(4-fluorophenyl)propyl][1,3,4]thiadiazol-2-ylcarbamoyl}phenyl)cyclohexyl]-acetic acid,
    (4-{4-[5-(4-fluorophenoxymethyl)[1,3,4]thiadiazol-2-ylcarbamoyl]phenyl}cyclohexyl)acetic acid,
    {4-[4-(5-phenyl[1,3,4]thiadiazol-2-ylcarbamoyl)phenyl]cyclohexyl}acetic acid,
    (4-{4-[5-(3-phenoxyphenyl)[1,3,4]thiadiazol-2-ylcarbamoyl]phenyl}cyclohexyl)acetic acid, {4-[4-(5-pyridin-4-yl[1,3,4]thiadiazol-2-ylcarbamoyl)
phenyl]cyclohexyl}acetic acid,
(4-{4-[5-(3-chlorophenyl)[1,3,4]thiadiazol-2-ylcarbamoyl]phenyl}cyclohexyl)acetic acid,
(4-{4-[5-(3-fluorophenyl)[1,3,4]thiadiazol-2-ylcarbamoyl]phenyl}cyclohexyl)acetic acid,
(4-{4-[5-(4-fluorophenyl)[1,3,4]thiadiazol-2-ylcarbamoyl]phenyl}cyclohexyl)acetic acid,
(4-{4-[5-(4-methoxyphenyl)[1,3,4]thiadiazol-2-ylcarbamoyl]phenyl}cyclohexyl)acetic acid,
(4-{4-[5-(benzyl)[1,3,4]oxadiazol-2-ylcarbamoyl]phenyl}cyclohexyl)acetic acid,
(4-{4-[5-(4-fluorobenzyl)[1,3,4]oxadiazol-2-ylcarbamoyl]phenyl}cyclohexyl)acetic acid,
cis-4-[4-(5-benzyl[1,3,4]thiadiazol-2-ylcarbamoyl)phenoxy]cyclohexanecarboxylic acid,
trans-4-[4-(5-benzyl[1,3,4]thiadiazol-2-ylcarbamoyl)phenoxy]cyclohexanecarboxylic acid,
trans-4-[4-(5-phenyl[1,3,4]thiadiazol-2-ylcarbamoyl)phenoxy]cyclohexanecarboxylic acid,
cis-4-[4-(5-benzyl[1,3,4]thiadiazol-2-ylcarbamoyl)-2-fluorophenoxy]cyclohexanecarboxylic acid,
cis-4-[4-(5-benzyl[1,3,4]thiadiazol-2-ylcarbamoyl)-2-chlorophenoxy]cyclohexanecarboxylic acid,
cis-4-{4-[5-(2-cyclopentylethyl)[1,3,4]thiadiazol-2-ylcarbamoyl]phenoxy}cyclohexanecarboxylic acid,
cis-4-(5-phenyl[1,3,4]thiadiazol-2-ylcarbamoyl)phenoxy]cyclohexanecarboxylic acid,
cis-4-{4-[5-(3-chlorophenyl)[1,3,4]thiadiazol-2-ylcarbamoyl]phenoxy}cyclohexanecarboxylic acid,
cis-4-{4-[5-(3-chlorophenyl)[1,3,4]thiadiazol-2-ylcarbamoyl]-2-fluorophenoxy}cyclohexanecarboxylic acid,
cis-4-[4-([1,3,4]thiadiazol-2-ylcarbamoyl)phenoxy]cyclohexanecarboxylic acid,
cis-4-[5-(5-benzyl[1,3,4]thiadiazol-2-ylcarbamoyl)pyridin-2-yloxy]cyclohexanecarboxylic acid,
cis-4-{5-[5-(3-chlorobenzyl)[1,3,4]thiadiazol-2-ylcarbamoyl]pyridin-2-yloxy}cyclohexanecarboxylic acid,
cis-4-[5-(5-phenethyl[1,3,4]thiadiazol-2-ylcarbamoyl)pyridin-2-yloxy]cyclohexanecarboxylic acid,
cis-4-[5-(5-phenyl[1,3,4]thiadiazol-2-ylcarbamoyl)pyridin-2-yloxy]cyclohexanecarboxylic acid,
cis-4-{5-[5-(3-chlorophenyl)[1,3,4]thiadiazol-2-ylcarbamoyl]pyridin-2-yloxy}cyclohexanecarboxylic acid,
cis-4-[4-(5-benzyl[1,3,4]thiadiazol-2-ylcarbamoyl)phenylamino]cyclohexanecarboxylic acid,
trans-4-[4-(5-benzyl[1,3,4]thiadiazol-2-ylcarbamoyl)phenylamino]cyclohexanecarboxylic acid,
trans-{4-[4-(5-benzyl[1,3,4]thiadiazol-2-ylcarbamoyl)phenyl]cyclohexyl}acetic acid,
trans-4-[4-(5-benzyl[1,3,4]thiadiazol-2-ylcarbamoyl)phenyl]cyclohexanecarboxylic acid,
trans-(4-{4-[5-(3-methoxyphenyl)[1,3,4]thiadiazol-2-ylcarbamoyl]phenyl}cyclohexyl)acetic acid,
trans-(4-{4-[5-(3-hydroxyphenyl)[1,3,4]thiadiazol-2-ylcarbamoyl]phenyl}cyclohexyl)acetic acid,
trans-{4-[4-(5-cyclopentyloxymethyl[1,3,4]thiadiazol-2-ylcarbamoyl)phenyl]cyclohexyl}-acetic acid,
trans-[4-(4-{5-[2-(tetrahydrofuran-2-yl)ethyl][1,3,4]thiadiazol-2-ylcarbamoyl}phenyl)cyclohexyl]acetic acid,
trans-(4-{4-[5-(2-cyclohexylethyl)[1,3,4]thiadiazol-2-ylcarbamoyl]phenyl}cyclohexyl)acetic acid,
trans-{4-[4-(5-cyclopentylmethoxymethyl[1,3,4]thiadiazol-2-ylcarbamoyl)phenyl]cyclohexyl}acetic acid,
trans-{4-[4-(5-benzylsulfanyl[1,3,4]thiadiazol-2-ylcarbamoyl)phenyl]cyclohexyl}acetic acid,
{4-[4-(5-benzyl[1,3,4]thiadiazol-2-ylcarbamoyl)phenyl]cyclohexylidene}acetic acid,
6-[4-(5-benzyl[1,3,4]thiadiazol-2-ylcarbamoyl)phenyl]spiro[2.5]octane-1-carboxylic acid,
(E)-3-{4-[4-(5-benzyl[1,3,4]thiadiazol-2-ylcarbamoyl)phenyl]cyclohexyl}acrylic acid,
trans-(1R,2S/1S,2R)-2-{4-[4-(5-benzyl[1,3,4]thiadiazol-2-ylcarbamoyl)phenyl]cyclohexyl}-cyclopropanecarboxylic acid,
trans-3-{4-[4-(5-benzyl[1,3,4]thiadiazol-2-ylcarbamoyl)phenyl]cyclohexyl}propionic acid,
(4-{4-[5-((1S,3S/1R,3R)-3-phenoxycyclohexyl)[1,3,4]thiadiazol-2-ylcarbamoyl]phenyl}-cyclohexyl)acetic acid,
trans-(4-{4-[(5-{[(3R,6S/3S,6R)-5-ethoxyoctahydropentalen-2-yl]methyl}-1,3,4-thiadiazol-2-yl)carbamoyl]phenyl}cyclohexyl)acetic acid,
trans-{4-[4-(5-benzyl[1,3,4]thiadiazol-2-ylcarbamoyl)phenyl]cyclohexyloxy}acetic acid,
trans-{4-[4-(5-bromo-[1,3,4]thiadiazol-2-ylcarbamoyl)phenyl]cyclohexyl}acetic acid,
trans-(4-{4-[5-(2-morpholin-4-ylethyl)[1,3,4]thiadiazol-2-ylcarbamoyl]phenyl}cyclohexyl)-acetic acid,
trans-{4-[4-(5-morpholin-4-yl[1,3,4]thiadiazol-2-ylcarbamoyl)phenyl]cyclohexyl}acetic acid,
trans-5-[4-(4-carboxymethylcyclohexyl)benzoylamino][1,3,4]thiadiazole-2-carboxylic acid,
trans-(4-{4-[5-(2-oxo-2-pyrrolidin-1-ylethyl)[1,3,4]thiadiazol-2-ylcarbamoyl]phenyl}cyclohexyl)acetic acid,
cis-4-[4-(5-cyclopentyloxymethyl[1,3,4]thiadiazol-2-ylcarbamoyl)phenoxy]cyclohexanecarboxylic acid,
trans-[4-(4-{5-[2-(tetrahydrofuran-3-yl)ethyl][1,3,4]thiadiazol-2-ylcarbamoyl}phenyl)-cyclohexyl]acetic acid,
trans-(4-{4-[5-(3-phenylcyclobutyl)[1,3,4]thiadiazol-2-ylcarbamoyl]phenyl}cyclohexyl)-acetic acid,
{4-[4-(5-phenylacetylamino[1,3,4]thiadiazol-2-ylcarbamoyl)phenyl]cyclohexyl}acetic acid,
trans-{4-[4-(5-cyclopentyloxymethyl[1,3,4]thiadiazol-2-ylcarbamoyl)phenyl]cyclohexyl}-acetic acid,
trans-(4-{4-[5-(3,5-difluorobenzyl)[1,3,4]thiadiazol-2-ylcarbamoyl]phenyl}cyclohexyl)-acetic acid,
trans-(4-{4-[5-(4-hydroxycyclohexylmethyl)[1,3,4]thiadiazol-2-ylcarbamoyl]phenyl}cyclohexyl)acetic acid,
trans-(4-{4-[5-(tetrahydrofuran-2-ylmethoxymethyl)[1,3,4]thiadiazol-2-ylcarbamoyl]-phenyl}cyclohexyl)acetic acid,
trans-{4-[4-(5-benzyl[1,3,4]thiadiazol-2-ylcarbamoyl)phenoxy]cyclohexyl}acetic acid,
trans-4-{4-[5-(tetrahydrofuran-2-ylmethoxymethyl)[1,3,4]thiadiazol-2-ylcarbamoyl]-phenoxy}cyclohexanecarboxylic acid,
trans-(4-{4-[5-(3-oxo-3-phenylpropyl)[1,3,4]thiadiazol-2-ylcarbamoyl]phenyl}cyclohexyl)-acetic acid,
trans-(4-{4-[5-(3-hydroxy-3-phenylpropyl)[1,3,4]thiadiazol-2-ylcarbamoyl]phenyl}cyclohexyl)acetic acid,
trans-(1S,2R)-2-(4-{4-[5-(3-chlorophenyl)[1,3,4]thiadiazol-2-ylcarbamoyl]phenyl}cyclohexyl)cyclopropanecarboxylic acid,
trans-N-(5-benzyl[1,3,4]thiadiazol-2-yl)-4-{4-[(2-hydroxy-2-methylpropylcarbamoyl)-methyl]cyclohexyl}benzamide,
trans-N-(5-benzyl[1,3,4]thiadiazol-2-yl)-4-(4-carbamoylmethylcyclohexyl)benzamide,
trans-N-(5-benzyl[1,3,4]thiadiazol-2-yl)-4-{4-[(2,3-dihydroxypropylcarbamoyl)methyl]-cyclohexyl}benzamide, trans-N-(5-benzyl[1,3,4]thiadiazol-2-yl)-4-{4-[(2-morpholin-4-ylethylcarbamoyl)methyl]-cyclohexyl}benzamide, trans-N-(5-benzyl[1,3,4]thiadiazol-2-yl)-4-{4-[(2-dimethylaminoethylcarbamoyl)methyl]-cyclohexyl}benzamide, trans-N-(5-benzyl[1,3,4]thiadiazol-2-yl)-4-{4-[(2-methoxyethylcarbamoyl)methyl]cyclohexyl}benzamide, trans-{4-[4-(5-cyclopentylamino[1,3,4]thiadiazol-2-ylcarbamoyl)phenyl]cyclohexyl}acetic acid, trans-N-(5-benzyl[1,3,4]thiadiazol-2-yl)-4-(4-{[([1,4]dioxan-2-ylmethyl)carbamoyl]-methyl}cyclohexyl)benzamide, trans-4-{4-[5-(3,5-difluorobenzyl)[1,3,4]thiadiazol-2-ylcarbamoyl]phenoxy}cyclohexanecarboxylic acid, trans-{4-[4-(5-phenylmethanesulfinylmethyl[1,3,4]thiadiazol-2-ylcarbamoyl)phenyl]cyclohexyl}acetic acid, trans-{4-[4-(5-benzylsulfanylmethyl[1,3,4]thiadiazol-2-ylcarbamoyl)phenyl]cyclohexyl}-acetic acid, trans-(4-{4-[5-(3-phenylcyclobutyl)[1,3,4]thiadiazol-2-ylcarbamoyl]phenyl}cyclohexyl)-acetic acid, cis-4-[5-(5-cyclopentyloxymethyl[1,3,4]thiadiazol-2-ylcarbamoyl)pyridin-2-yloxy]cyclohexanecarboxylic acid, trans-(4-{4-[5-(2-cyclopentylaminoethyl)[1,3,4]thiadiazol-2-ylcarbamoyl]phenyl}cyclohexyl)acetic acid, cis-4-(4-{5-[2-(3-morpholin-4-ylcyclopentyl)ethyl][1,3,4]thiadiazol-2-ylcarbamoyl}-phenoxy)cyclohexanecarboxylic acid, cis-4-[4-(5-cyclopentylamino[1,3,4]thiadiazol-2-ylcarbamoyl)phenoxy]cyclohexanecarboxylic acid, cis-4-{4-[5-(3-oxo-3-phenylpropyl)[1,3,4]thiadiazol-2-ylcarbamoyl]phenoxy}cyclohexanecarboxylic acid or cis-4-{4-[5-(3,5-difluoro-benzyl)-[1,3,4]thiadiazol-2-ylcarbamoyl]-phenoxy}-cyclohexanecarboxylic acid.

13. A process for preparing the compound according to claim 1 wherein $Z_1$ is absent, W is a carbon atom, R is a hydrogen atom, D is a bond, $Z_4$ is a hydrogen atom, $Z_2$ and $Z_3$ are each absent, p is 1, R3 and R4 are each a hydrogen atom, and U is an oxygen atom, comprising deprotecting the ester function of a compound of formula (V)

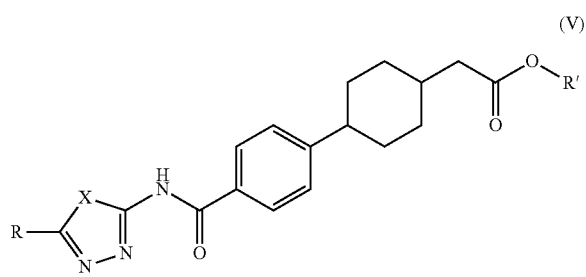

(V)

in the presence of an acid or a base wherein R represents a group —C(R1R2)n-Y and X, Y, R1, R2 and n are as defined in claim 1 and R' represents the protecting group, wherein the protecting group is (C1-C6)-alkyl or benzyl.

14. The process according to claim 13, wherein the preparation of the compound of formula (V), is performed by reacting (i) a compound of formula (II):

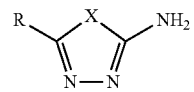

(II)

wherein R represents a group —C(R1R2)n-Y and X, Y, R1, R2 and n are as defined in claim 13, with (ii) a compound of formula (III)

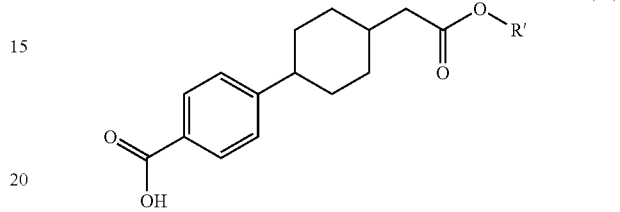

(III)

wherein R' represents the protecting group, wherein the protecting group is (C1-C6)-alkyl or benzyl.

15. The process according to claim 13, wherein the preparation of the compound of formula (XXIII), is performed by reacting (i) a compound of formula (II):

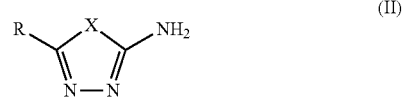

(II)

wherein R represents a group —C(R1R2)n-Y and X, Y, R1, R2 and n are as defined in claim 13, with (ii) a compound of formula (XXI)

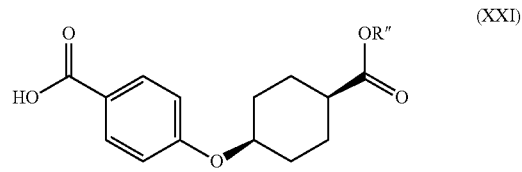

(XXI)

wherein R" represents the protecting group, wherein the protecting group is (C1-C6)-alkyl or benzyl.

16. A compound of formula (III):

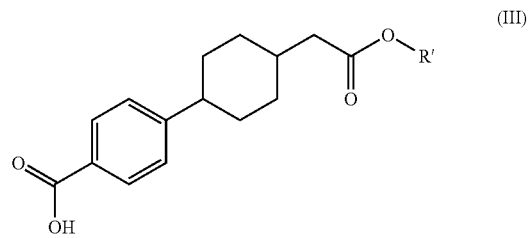

(III)

wherein R' represents a protecting group, wherein the protecting group is (C1-C6)-alkyl or benzyl.

17. A compound of formula (V):

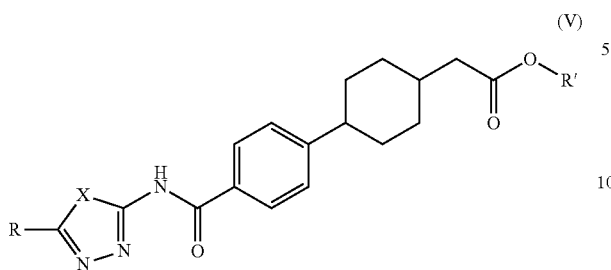

(V)

wherein R represents a group —C(R1R2)n-Y with Y, R1, R2, n and X as defined in claim 1 and R' represents a protecting group, wherein the protecting group is (C1-C6)-alkyl or benzyl.

18. A compound of formula (XXIII):

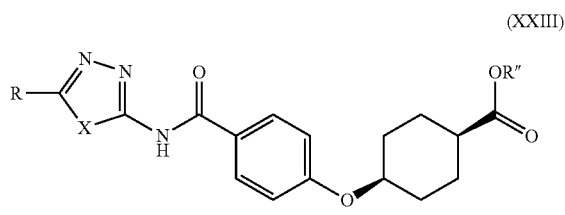

(XXIII)

wherein R represents a group —C(R1R2)n-Y with Y, R1, R2, n and X as defined in claim 1 and R' represents a protecting group, wherein the protecting group is (C1-C6)-alkyl or benzyl.

19. A compound of formula (XXI):

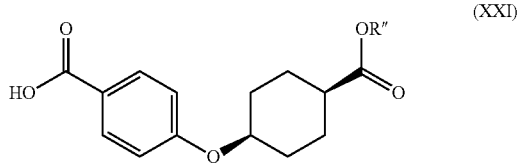

(XXI)

wherein R" represents a protecting group, wherein the protecting group is (C1-C6)alkyl or benzyl, with the exclusion of the compound 4-(4-ethoxycarbonylcyclohexyloxy)benzoic acid.

20. A pharmaceutical composition comprising the compound of claim 1, or an addition salt of said compound with a pharmaceutically acceptable acid or base.

21. The pharmaceutical composition according to claim 20, further comprising at least one pharmaceutically acceptable excipient.

22. A method of treating a disorder selected from the group consisting of obesity, dyslipidaemia, and the accumulation and an excess of triacylglycerides in adipose tissue (WAT) in a patient in need thereof comprising administering to said patient a therapeutically effective amount of the pharmaceutical composition of claim 20.

23. A process for preparing the compound according to claim 1 wherein $Z_1$ is absent, W is a carbon atom, R is a hydrogen atom, D is an oxygen atom, p is 0, $Z_2$ and $Z_3$ are each absent, $Z_4$ is a hydrogen atom, and U is an oxygen atom, comprising deprotecting the ester function of a compound of formula (XXIII):

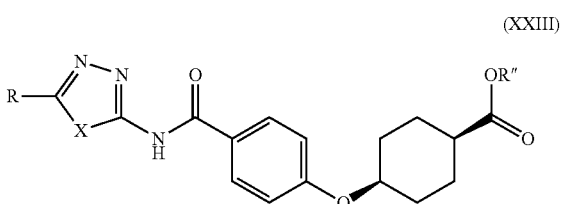

(XXIII)

in the presence of an acid or a base wherein R represents a group —C(R1R2)n-Y and X, Y, R1, R2 and n are as defined in claim 1, and R" represents the protecting group, wherein the protecting group is (C1-C6)-alkyl or benzyl.

24. The compound according to claim 1, wherein $Z_2$ and $Z_3$ together form cycloalkyl.

25. The compound according to claim 9, wherein $Z_2$ and $Z_3$ together form cyclopropyl.

* * * * *

UNITED STATES PATENT AND TRADEMARK OFFICE
CERTIFICATE OF CORRECTION

PATENT NO. : 8,546,391 B2
APPLICATION NO. : 13/145665
DATED : October 1, 2013
INVENTOR(S) : Fett et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this
Fifteenth Day of September, 2015

Michelle K. Lee
*Director of the United States Patent and Trademark Office*